US006004959A

United States Patent [19]
Jones et al.

[11] Patent Number: 6,004,959
[45] Date of Patent: Dec. 21, 1999

[54] ALKYLOXYAMINO SUBSTITUTED FLUORENONES AND THEIR USE AS PROTEIN KINASE-C INHIBITORS

[75] Inventors: Winton D. Jones; Fred L. Ciske; Robert J. Dinerstein, all of Cincinnati; Keith A. Diekema, West Chester, all of Ohio

[73] Assignee: Hoechst Marion Roussel, Inc., Bridgewater, N.J.

[21] Appl. No.: 08/844,209

[22] Filed: Apr. 18, 1997

Related U.S. Application Data

[60] Provisional application No. 60/109,603, May 30, 1996.

[51] Int. Cl.$^6$ .................. A61K 31/40; A61K 31/535; C07D 295/116
[52] U.S. Cl. .................. 514/238.8; 514/651; 544/155; 546/204; 548/528; 564/322; 564/352
[58] Field of Search .................. 544/155; 548/528; 564/352; 514/238.8

[56] References Cited

U.S. PATENT DOCUMENTS

| | | |
|---|---|---|
| 3,592,819 | 7/1971 | Fleming et al. . |
| 3,671,587 | 6/1972 | Trexler et al. . |
| 3,814,770 | 6/1974 | Andrews et al. . |
| 4,064,347 | 12/1977 | Fleming et al. . |
| 4,816,450 | 3/1989 | Bell et al. . |
| 5,189,046 | 2/1993 | Burch et al. . |
| 5,340,931 | 8/1994 | Yamada et al. . |
| 5,459,262 | 10/1995 | Schmitz . |
| 5,514,719 | 5/1996 | LaTorse et al. . |

FOREIGN PATENT DOCUMENTS

| | | |
|---|---|---|
| 0578586 | 1/1994 | European Pat. Off. . |
| 94219 | 11/1964 | Netherlands . |
| 1244348 | 8/1971 | United Kingdom . |
| 1392313 | 4/1975 | United Kingdom . |
| 1392314 | 4/1975 | United Kingdom . |
| 9221660 | 12/1992 | WIPO . |
| 9303060 | 2/1993 | WIPO . |
| 9311758 | 6/1993 | WIPO . |
| 9500468 | 1/1995 | WIPO . |

OTHER PUBLICATIONS

Fu et al, J. Org. Chem., 56, pp. 1683–1685 (1991).
de Silva et al, Tetrahedron, vol. 48, No. 23, pp. 4863–4878 (1992).
Ladd, D., et al, J. Med. Chem. 29, pp. 1904–1912 (1986).
Sill, A., et al, J. Medicinal Chem., vol. 16, No. 3, pp. 240–245 (1973).
Miller, M., et al, J. Am. Chem. Soc., 102, pp. 7026–7032 (1980).
Bradshaw, D., et al, Agents Actions 38, pp. 135–147 (1993).
Davis, P., et al, FEBS Letters, vol. 259, No. 1, pp. 6–63 (1989).
Chemical Abstracts, vol. 62 (1965).
Chemical Abstracts, vol. 65 (1966).
Sala, T. et al, J. Chem. Soc. Perkin Trans. I, pp. 2593–2598 (1979).
Andrews, E.R., et al, J. Medicinal Chem. vol. 17, No. 8, pp. 882–886 (1974).
Sargent, M.V., J. Chem. Soc. Perkin Trans., 1, pp. 2553–2563 (1987).
Fu, J.–M., et al, Can. J. Chem., vol. 72, pp. 227–236 (1994).
Wang, W. et al, J. Org. Chem., 57, pp. 424–426 (1992).
Meyers, A., et al, J. Org. Chem., vol. 39, No. 18, pp. 2787–2793 (1974).
Meyers, A., et al, J. Am. Chem. Soc. Comm., 97:25, pp. 7383–7385 (1975).
Morgan, G., et al, J. Chem. Soc. Perkin Trans. I, pp. 2691–2696 (1926).
Mohindra, H., et al, Indian J. of Chem., vol. 26B, pp. 992–993, (Oct. 1987).
Gant, T., et al, Tetrahedron, vol. 30, No. 8, pp. 2297–2360 (1994).
Reuman, M., et al, Tetrahedron, vol. 40, No. 5, pp. 837–860 (1985).
Hannun, Y., et al, J. of Biological Chem., vol. 262, No. 28, pp. 13620–13626, (Oct. 5, 1987).
Wilson, E., et al, J. of Biological Chem., vol 261, No. 27, pp. 12616–12623 (Sep. 25, 1986).
Castagna, M., et al, J. of Biological Chem., vol. 262, No. 13, pp. 7847–7851, (Jul. 10, 1982).
Pittet, D. et al, J. Biological Chem.,vol. 262, pp. 10072–10076 (Jul. 25, 1987).
Fujita, I., et al, Biochemical Pharmacology, vol. 35, No. 24, pp. 4555–4562 (1886).
Gaudry, M., et al, Immunology, 63, pp. 715–719 (1988).
Yamada, K., et al, Biochemical Pharmacology, vol. 37, No. 6, pp. 1161–1166 (1988).
Berkow, R., et al, J. of Leukocyte Biology, 41, pp. 441–446 (1987).
Schächtele, C., et al, Biochemical and Biophysical Research Comm., vol. 151, No. 1, pp. 542–547 (Jan. 29, 1988).
Salzer, W., et al, Biochem. Biophys. Res. Comm., vol. 148, No. 2, pp. 747–754 (Oct. 29, 1987).
Dewald, B., et al, Biochem. J., 264, pp. 879–884 (1989).
Kramer, I., et al, J. Biological Chem., vol. 264, No. 8, pp. 3818–3822 (Mar. 15, 1988).
Lambeth, J., et al, J. of Biological Chem., vol. 263, No. 8, pp. 3818–3822 (Mar. 15, 1988).
McIntyre, T., et al, J. Biological Chem., vol. 262, No. 32, pp. 15370–15376 (Nov. 15, 1987).
Dodd, J., Synthetic Communications, 23(7), pp. 1003–1008 (1993).

(List continued on next page.)

Primary Examiner—Robert W. Ramsuer
Attorney, Agent, or Firm—T. Helen Payne

[57] ABSTRACT

The present invention describes certain alkyloxyamino-substituted fluorenones which inhibit protein kinase C, as well as pharmaceutical compositions including these compounds and methods of using these compounds to control protein kinase C activity in mammals, including humans. More specifically, the present compounds are useful for the treatment of neoplastic disease states, disorders associated with abnormal blood flow (including hypertension, ischemia, atherosclerosis, coagulation disorders), and inflammatory diseases (including immune disorders, asthma, lung fibrosis, and psoriasis).

26 Claims, No Drawings

OTHER PUBLICATIONS

Barker, A., et al, J. Chem. Soc. 870 (1954).

Colste, J. et al, Tetrahedron Letters, vol. 31, No. 2, pp. 205–208 (1990).

Martinez, J. et al, J. Med. Chem., 28, pp. 1874–1879 (1985).

Frerot E., et al, Tetrahedron Letters, vol. 47, No. 2, pp. 259–270 (1991).

Hoeg–Jensen, T. et al, Tetrahedron Letters, vol. 32, No. 51, pp. 7617–7620 (1991).

Calbiochem–Novabiochem. Corp. Catalog pp. 162–165.

Jones, Winton et al, J. Org. Chem., vol. 61, No. 11, pp. 3920–3922.

ALKYLOXYAMINO SUBSTITUTED FLUORENONES AND THEIR USE AS PROTEIN KINASE-C INHIBITORS

This application claims the benefit of U.S. Provisional Application No. 06/109,803, Filed May 30, 1996, which is hereby incorporated by reference.

BACKGROUND OF THE INVENTION

The present invention relates to compounds having protein Kinase C inhibitory activity. More particularly, the present invention relates to alkyloxyamino-substituted fluorenones which inhibit protein kinase C, pharmaceutical compositions including these compounds and methods of using these compounds to control protein kinase C activity in mammals, including humans. More specifically, the present compounds are useful for the treatment of neoplastic disease states, disorders associated with abnormal blood flow (including hypertension, ischemia, atherosclerosis, coaggulation disorders), and inflammatory diseases (including immune disorders, asthma, lung fibrosis, psoriasis).

Protein kinase C (PKC) constitutes a family of enzymes called protein kinases. Activation of a protein kinase catalyzes the transfer of the γ-phosphate of MqATP to either a serine, threonine residue of a particular protein substrate. Protein kinases regulate virtually all cell functions through the phosphorylation of proteins that are responsible for signal transduction and the regulation of cellular processes. Inhibitors of protein kinases could thus alter cell activities and thus can serve as pharmacological agents. Protein kinase C is a phospholipid-dependent, calcium activated serine/threonine protein kinase which was first characterized in the brain by Y. Nishizuka, *Science* 233:305–312 (1986). Subsequently, PKC was further characterized as a family of at least 11 enzymes. A. Azzi et al., *Eur.J.Biochem.* 208:547–557 (1992); D. S. Lester and R. M. Epand, *Current Concepts and Future Perspectives*, Ellis Horward, New York (1992); H. Hug and T. F. Sarre, *Biochem. J.* 291:329–343 (1993); C. Tanaka and Y. Nishizuka, *Annu. Rev. Neurosci.* 17:551–67 (1994); S. E. Wilkinson, T. J. Hallam, *Trends Pharm. Sci.* 15:53–57 (1994); E.O Harrington and A. J. Ware, *Trends Cardiovas. Med.* 5:193–199 (1995); A. C. Newton, *J. Biol. Chem.* 270:28495–28498 (1995); all of which are herein incorporated by reference.

Members of the Protein Kinase C family consist of a single polypeptide with a N-terminal regulatory end and a C-terminal catalytic end. The regulatory domain for all of the isozymes requires phospholipid for enzymatic activity, but only some of them require calcium for activation and some of them are not activated by phorbol myristate acetate (PMA), and agent long associated with PKC activation. On the other hand, the catalytic portion of the PKC enzymes are quite similar, but they share limited homology with other classes of kinases. For example, there is only 40% homology in this region with another well characterized protein kinase, protein kinase A (PKA). Analysis, of the catalytic site also uncovered a cluster of acidic residues unique to the protein kinase C family of enzymes J. W. Orr, A. C. Newton, *J. Biol. Chem.* 269:8383–8367 (1994). Thus, inhibitors or pharmaceutical agents directed at the catalytic site of this enzyme would be expected to be specific for the protein kinase C family of enzymes. Because of the potential therapeutic value of inhibitors of PKC, there is considerable effort being made to identify such substances. H. H Grunick, F. Ueberall, *Sem. in Cancer Biol.* 3:351–360 (1992); D. Bradshaw et al., *Agents Actions* 38:135–147 (1993); W. Harris et al., *Drugs Future* 18:727–735 (1993); A. Levitzi, *Eur. J. Biochem.* 226:1–13 (1994); K. J. Murray and W. J. Coates, *Annu. Reports Med. Chem.* 29:255–264 (1994); P. C. Gordge and W. J. Ryves, *Cell. Signal* 6:871–882 (1994); P. M. Blumberg et al., *Agents Action Suppl.* 47:87–100 (1995); J. C. Lee and J. L. Adams, *Curr. Opp. Biotech.* 6:657–661 (1995); all of which are herein incorporated by reference.

PKC regulates key steps in cell proliferation and cell growth. Potent activators of PKC, such as the phorbol esters, are well-known carcinogens. Thus, inhibitors of PKC would also be expected to be anticancer agents. The anticancer activity of several PKC inhibitors is well known, Grunick, supra., Levitzi, supra., Lee et al., supra, T. Meyer et al., *Int. J. Cancer* 43:851–856 (1989); S. Akinagaka et al., *Cancer Res.* 51:4888–4992 (1991), including activity against tumors expressing the multi-drug resistance phenotype I. Utz et al, *Int. J. Cancer* 57:104–110 (1994); all of which are herein incorporated by reference. A PKC inhibitor showed specificity in suppressing CDC2 kinase activity and in arresting cell cycling J. Hoffman et al., *Biochem. Biophys. Res. Commun.* 199:937–943 (1994), herein incorporated by reference. Inhibition of protein kinase C has been demonstrated to suppress tumor metastasis, J. A. Dumont et al., *Cancer Res.* 52:1195–1200 (1992), J. A. Dumont et al., *Biochem. Biophys. Res. Comm.* 204:264–272 (1994); all of which are herein incorporated by reference. Angiogenesis, the formation of new blood vessels, when associated with tumor formation and growth, fosters such formation and growth and in such instances is a pathological event.

Protein kinase C activation has been linked to mechanisms that set the rate of flow in blood vessels. Excessive PKC activity is likely implicated in hypertension, ischemia, and athersclerosis; all of these processes contribute to impaired blood flow, and can lead to ischemic heart disease, myocardial infarction, or stroke. Phorbol esters will produce increased contractility in the arteries from hypertensive rats, along with elevated PKC activity intrinsic to their vasculature and platelets, E. O. Harrington and A. J. Ware, supra; D. Bradshaw, et al., supra. Platelet aggregation is accompanied by PKC activation, contributing to abnormal clot formation and blood flow obstruction. M. A. Evans, et al., *Br. Heart J.* 68:109, herein incorporated by reference. Hyperplasia and proliferation of vascular smooth muscle plays a central role in the formation of atherosclerotic plaques. Activation of PKC is involved in smooth muscle proliferation E. O. Harrington and A. J. Ware, supra.

Tissues and organs become inflamed as a result of infiltration by certain activated white blood cells. The long term consequences can be tissue damage resulting in fibrosis. Both inflammatory cell activation and fibrotic processes have been associated with the excessive activity of protein kinase C. The T lymphocyte (T-cell) is the coordinator of immune responses. PKC plays a central role in the activation of these cells and PKC inhibitors will inhibit their activation and growth. D. Bradshaw et al., supra, W. Harris et al., supra, S. S. Alkkan et al., *Cell. Immunol.* 150:137–148 (1993), herein incorporated by reference. Not surprisingly, PKC inhibitors have been demonstrated to have activity in diseases where T-cells play a major role, such as transplant rejection J. P. Demers et al, *Bioorg. Med. Chem. Lett.* 4:2451–56, and psoriasis. L. Hegemann et al., Arch. Dermatol. Res. 284:179–183 (1992); J. J. Tegeler et al., *Bioorg. Med. Chem. Lett.* 5:2477–2482 (1995); all of which are herein incorporated by reference. White blood cells, such as monocytes (macrophages), neutrophils, and eosinophils can be activated by phorbol esters and their activities, such as free radical generation, phagocytosis, chemotaxis, and secretion can be suppressed by inhibitors of PKC. C-K Huang and R. I. Sha'afi, *Protein kinases in blood cell function*, CRC press, Boca Raton, Ch. 3,4,5; herein incorporated by reference. These granulocytes participate in and are largely responsible for the acute inflammatory processes that occur in such diseases as asthma, allergies and gouty arthritis. Thus, it is expected that inhibitors of PKC would have general antiinflammatory activity. A consequence of chronic inflammation is fibrosis. It is particularly notable that the class of compounds (fluorenones) described in this patent, and which we have identified as inhibitors of PKC, suppress alveolar macrophage activation and fibroblast proliferation and thus would be expected to have antiinflammatory and anti-fibrotic activity in the lung, J. Y. C. Ma et al., *Exp. Lung Res.* 21:771–790 (1995); herein incorporated by reference.

As related above, the implication of PKC in several human disease processes, including neoplastic disease states, vascular perfusion disorders, and inflammation, the inhibition of this enzyme would be expected to be of great value in treating these disorders. Furthermore, PKC inhibitors which are highly specific for the PKC class of protein kinases, which have minimal effects on other metabolic pathways such as those associated with stimulation of protein kinase A by cAMP are greatly desired. Neoplastic disease states, vascular perfusion disorders, and inflammation are common conditions for which there still exists a great need for novel and more definitive treatments.

SUMMARY OF THE INVENTION

The present invention describes compounds, their pharmaceutically acceptable salts and pharmaceutical compositions of the formula:

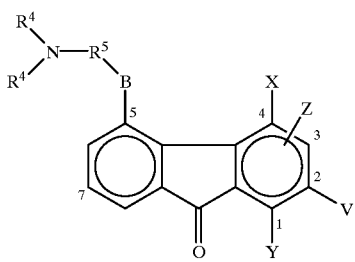

(1)

wherein:
B is O, S or NH;
$R^4$ is methyl, ethyl, n-propyl, or both $R^4$'s can be combined to give pyrrolidinyl, piperidinyl or morpholino;
$R^5$ is $C_{1-5}$ alkylene;
V is hydrogen, methoxy, ethoxy, n-propoxy, n-butoxy;
X is hydrogen, methoxy, ethoxy, n-propoxy, fluoro or chloro;
Y is hydrogen or $NH_2$, NHR, NHCOR, wherein R is $C_{1-5}$ alkyl or phenyl;
Z is H, $C_{1-5}$ alkyl, fluoro, chloro, $BR^5N(R^4)_2$, wherein $R^4$, $R^5$ and B are as above defined;
with the proviso that:
Z may be present at the 1, 2, 3 or 4 position, and when present at the 1, 2 or 4 position, replaces Y, V, or X, respectively;
with the further proviso that when:
Z is $BR^5N(R^4)_2$ then at least one of Y, V or X is not hydrogen nor replaced by Z.

The present invention also relates to the use of compounds and their pharmaceutically acceptable salts of the formula:

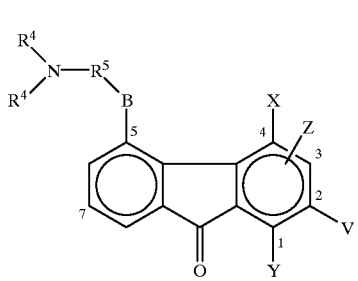

(2)

wherein:
B is O, S or NH;
$R^4$ is methyl, ethyl, n-propyl, or both $R^4$'s can be combined to give pyrrolidinyl, piperidinyl or morpholino;
$R^5$ is $C_{1-5}$ alkylene;
V is hydrogen, methoxy, ethoxy, n-propoxy, butoxy;
X is hydrogen, methoxy, ethoxy, n-propoxy, fluoro, or chloro;
Y is H or $NH_2$, NHR, NHCOR, wherein R is $C_{1-5}$ alkyl or phenyl;
Z is H, $C_{1-5}$ alkyl, fluoro, chloro, $BR^5N(R^4)_2$, wherein $R^4$, $R^5$ and B are as above defined;
wherein further,
Z may be present at the 1, 2, 3 or 4 position, except that when present at the 1, 2 or 4 position, replaces Y, V or X, respectively;

for the treatment of disorders mediated by PKC. These disorders include, for example, neoplastic disease states, abnormal blood flow disorders (including hypertension, ischemia, atherosclerosis, coagulation disorders), and inflammatory diseases (including immune disorders, asthma, lung fibrosis and psoriasis). The compounds of this invention are also useful in the therapeutic inhibition of angiogensis and in the inhibition of alveolar macrophage activation.

Moreover, the present invention also relates to a process for the preparation of a compound of the formula:

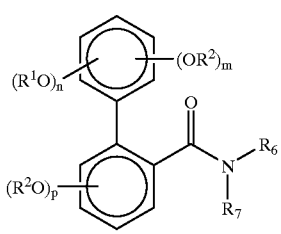

wherein $R^1$ and $R^2$ are each independently methyl, ethyl, n-propyl, isopropyl, n-butyl or allyl; $R_6$ and $R_7$ are each independently ethyl or propyl; and m, n and p are each independently 0 or 1; comprising reacting a compound of the formula:

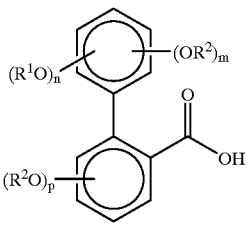

wherein $R^1$, $R^2$, m, n and p are as defined above; with thionyl chloride followed by in situ reaction with an amine of the formula $(R_6)(R_7)NH$, wherein $R_6$ and $P_7$ are as defined above.

Furthermore, the present invention also relates to a process for the preparation of a compound of the formula:

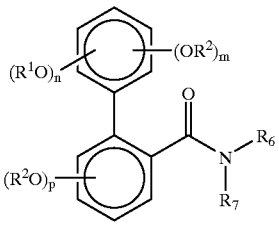

wherein $R^1$ and $R^2$ are each independently methyl, ethyl, n-propyl, isopropyl, n-butyl or allyl; $R_6$ and $R_7$ are each independently ethyl or propyl; and m, n and p are each independently 0 or 1; comprising reacting a compound of the formula:

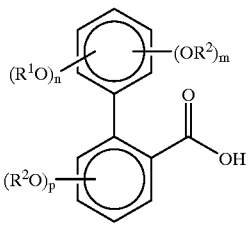

wherein $R^1$, $R^2$, m, n and p are as defined above; with benzotriazole-1-yl-oxy-tris(pyrolidino)phosphonium hexafluorophosphate in the presence of an amine of the formula $(R_6)(R_7)NH$ and a tri-($C_{1-5}$ alkyl)amine, wherein $R_6$ and $R_7$ are as defined above.

Further, the present invention relates to a process for the preparation of a compound of the formula:

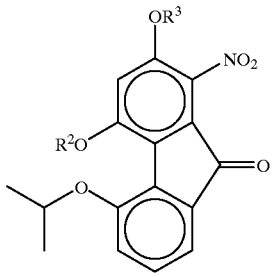

wherein $R^2$ and $R^3$ are each independently methyl, ethyl, n-propyl, isopropyl, n-butyl or allyl;

comprising reacting a compound of the formula:

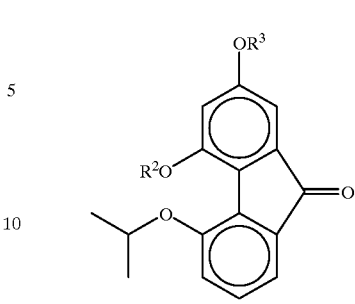

wherein $R^2$ and $R^3$ are as defined above, with nitronium tetrafluoroborate.

Finally, the present invention relates novel compounds of the formula

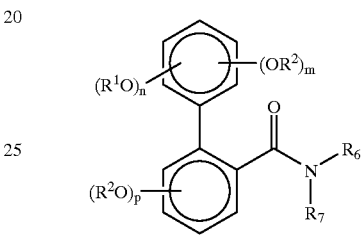

wherein $R^1$ and $R^2$ are each independently methyl, ethyl, n-propyl, isopropyl, n-butyl or allyl; $R_6$ and $R_7$ are each independently ethyl or propyl; and m, n and p are each independently 0 or 1; with the proviso that at least one of $R^1$ and $R^2$ is allyl; which are useful as intermediates to make the compounds of formulae (1) and (2).

DETAILED DESCRIPTION OF THE INVENTION

As used herein, the term "pharmaceutically acceptable salt" is intended to mean any organic or inorganic acid salt which is capable of forming a non-toxic acid addition salt which is suitable for use as a pharmaceutical. Illustrative inorganic acids which form suitable salts include hydrochloric, hydrobromic, sulphuric, and phosphoric acid and acid metal salts such as sodium monohydrogen orthophosphate, and potasssium hydrogen sulfate. Illustrative organic acids which form suitable salts include the mono-, di- and tri-carboxylic acids. For example, acetic, glycolic, lactic, pyruvic, malonic, succinic, glutaric, fumaric, malic, tartaric, citric, ascorbic, maleic, hydroxymaleic, hydroxybenzoic, phenylacetic, cinnamic, salicylic, glutamic, gluconic, formic and sulfonic acids such as methane sulfonic acid and 2-hydroxyethane sulfonic acid. Further examples of suitable pharmaceutically-acceptable salts are recited in Berge, S. M et al, *J. Pharm. Sci.* 66:1, 1 (1977). Such salts can exist in either a hydrated or substantially anhydrous form.

As used herein, the term "patient" refers to a warm blooded animal such as a mammal which is afflicted with a particular disease. It is explicitly understood that guinea pigs, dogs, cats, rats, mice, horses, cattle, sheep and humans are examples of animals within the scope of the term.

As used herein, the term "effective protein Kinase C inhibitory amount", is such an amount wherein an enzyme inhibitory effect is achieved, upon single or multiple dose administration to a patient, sufficient to cause a therapeutic effect in the patient. The exact amount of a compound of formulae (1) or (2) to be administered can be readily determined by the attending diagnostician, as one ordinarily skilled in the art, by the use of conventional techniques and by observing results obtained under analogous circumstances. Factors significant in determining the dose include: the dose; the species of animal, its size, age and general health; the specific disease involved, the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective protein Kinase C inhibitory amount of a compound of formulae (1) or (2) will generally vary from about 0.5 milligram per kilogram (mg/kg) of body weight to about 200 mg/kg of body weight per day. A daily dose of from about 0.625 mg to 100 mg/kg of body weight per day is preferred.

The compounds of this invention are inhibitors of protein Kinase C. It is believed that the compounds of this invention exert their inhibitory effect through inhibition of protein Kinase C and thereby prevent or provide relief of symptoms for neoplastic disease states, abonormal blood flow disorders, inflammatory diseases, and the like. However, it is understood that the present invention is not limited by any particular theory or proposed mechanism to explain its effectiveness in an end-use application.

The term "neoplastic disease state" as used herein refers to an abnormal state or condition characterized by rapidly proliferating cell growth or neoplasm. Neoplastic disease states for which treatment with a compound of formulae (1) or (2) will be particularly useful include: Leukemias such as, but not limited to, acute lymphoblastic, chronic lymphocytic, acute myeloblastic and chronic myelocytic; Carcinomas and adenocarcinomas, such as, but not limited to, those of the cervix, oesophagus, stomach, small intestines, colon, lungs (both small cell and large cell), breast and prostate; Sarcomas, such as, but not limited to, oesteroma, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, follicullar reticulum, cell sarcoma and Hodgkins Disease. Neoplastic disease states for which treatment with a compound of formulae (1) or (2) will be particularly preferred include carcinomas and adenocarcinomas, particularly of the breast, prostate and lung. An effective protein Kinase C inhibitory amount of a compound of formulae (1) or (2), refers to an amount which is effective, upon single or multiple dose administration to the patient, in controlling the growth of the neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm.

As used herein, the term "$C_{1-5}$ alkylene" refers to a saturated hydrocarbyldiyl radical of straight or branched configuration made up of from one to five carbon atoms. Included within the scope of this term are methylene, ethylene, n-propylene, isopropylene, n-butylene, sec-butylene, n-pentylene and the like.

As used herein, the term "$C_{1-5}$ alkyl" refers to a saturated hydrocarbyl radical of straight or branched configuration, made up of from one to five carbon atoms. Included within the scope of this term are methyl, ethyl, propyl, isopropyl, n-butyl, s-butyl, n-pentyl and the like.

As used herein, the term "$C_{1-4}$ alkyl" refers to a saturated hydrocarbyl radical of straight or branched configuration, made up of from one to four carbon atoms. Included within the scope of this term are methyl, ethyl, propyl, isopropyl, n-butyl, s-butyl and the like.

As used herein, the term "PyBOP" or benzotriazole-1-yl-oxy-tris(pyrolidino)phosphonium hexafluorophosphate refers to a benzotriazole-1-yl-oxy-tris(pyrolidino) phosphonium hexafluorophosphate of the formula

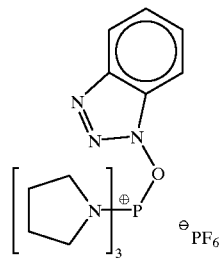

FORMULATIONS

A compound of formulae (1) or (2) can be administered in the form of pharmaceutical compositions or medicaments which are made by combining a compound of formulae (1) or (2) with pharmaceutically acceptable carriers or excipients, the proportion and nature of which are determined by the chosen route of administration, and standard pharmaceutical practice.

The pharmaceutical compositions of the invention are prepared in a manner well known in the pharmaceutical art. The carrier or excipient may be a solid, semisolid, or liquid material which can serve as a vehicle or medium for the active ingredient. Suitable carriers or excipients are well known in the art. The pharmaceutical compositions may be adapted for oral, inhalation, parenteral, or topical use and may be administered to the patient in the form of tablets, capsules, aerosols, inhalants, suppositories, solution, suspensions, powders, syrups, and the like. As used herein, the term "pharmaceutical carrier" may encompass one or more excipients.

In preparing formulations of the compounds of the invention, care should be taken to ensure bioavailability of an effective inhibitory amount, including oral, parental and subcutaneous routes. For example, effective routes of administration may include, subcutaneously, intramuscularly, transdermally, intranasally, rectally and the like including release from implants as well as direct injection of the active ingredient and/or composition directly into the tissue or tumor sites. Suitable pharmaceutical carriers and formulation techniques are found in standard texts, such as *Remington's Pharmaceutical Sciences*, Mack Publishing Co., Easton, Pa.

For oral administration, the compounds can be formulated into solid or liquid preparations, with or without inert diluents or edible carrier(s), such as capsules, pills, tablets, troches, powders, solutions, suspensions or emulsions. The tablets, pills, capsules, troches and the like may also contain one or more of the following adjuvants: binders such as microcrystalline celluose, gum tragacanth or gelatin; excipients such as starch or lactose; disintegrating agents such as alsinic acid, Primogel®, corn starch and the like; lubricants such as stearic acid, magnesium stearate or Sterotex®;

glidants such as colloidal silicon dioxide; sweetening agents such as sucrose or saccharin; and flavoring agents such as peppermint, methyl salicylate or fruit flavoring. When the dosage unit form is a capsule, it may also contain a liquid carrier such as polyethylene glycol or fatty oil. Materials used should be pharmaceutically pure and non-toxic in the amounts used. These preparations should contain at least 0.05% by weight of a compound of formulae (1) or (2), the active ingredient, but may be varied depending upon the particular form and may conveniently be between 0.05% to about 90% or the weight of the unit. The amount of active ingredient present in compositions is such that a unit dosage form suitable for administration will be obtained.

For the purpose of parenteral administration, a compound of formulae (1) or (2) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants depending on the solubility and other properties of a compound of formulae (1) or (2): sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The compounds can be administered in the form of a cutaneous patch, a depot injection, or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones. Further information on suitable pharmaceutical carriers and formulation techniques are found in standard texts such as *Remington's Pharmaceutical Sciences*.

Chemical Syntheses

In the synthesis of the bis-basic fluorenone compounds of the invention, the starting compounds are known or may be prepared by known techniques, such as given in Meyers et al., *J. Org. Chem.*, 39(18), 2787 (1974) in combination with Meyers & Mihelich, *J. Amer. Chem. Soc.*, 97(25), 7383 (1975).

The following examples describe particular syntheses which have been adapted in part from the available literature.

Scheme 1

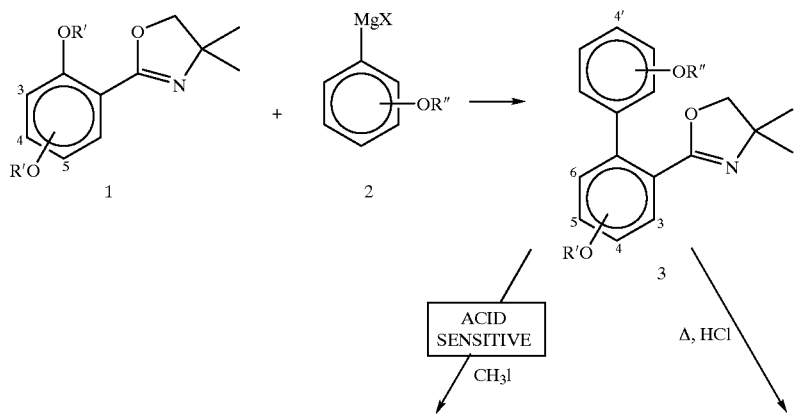

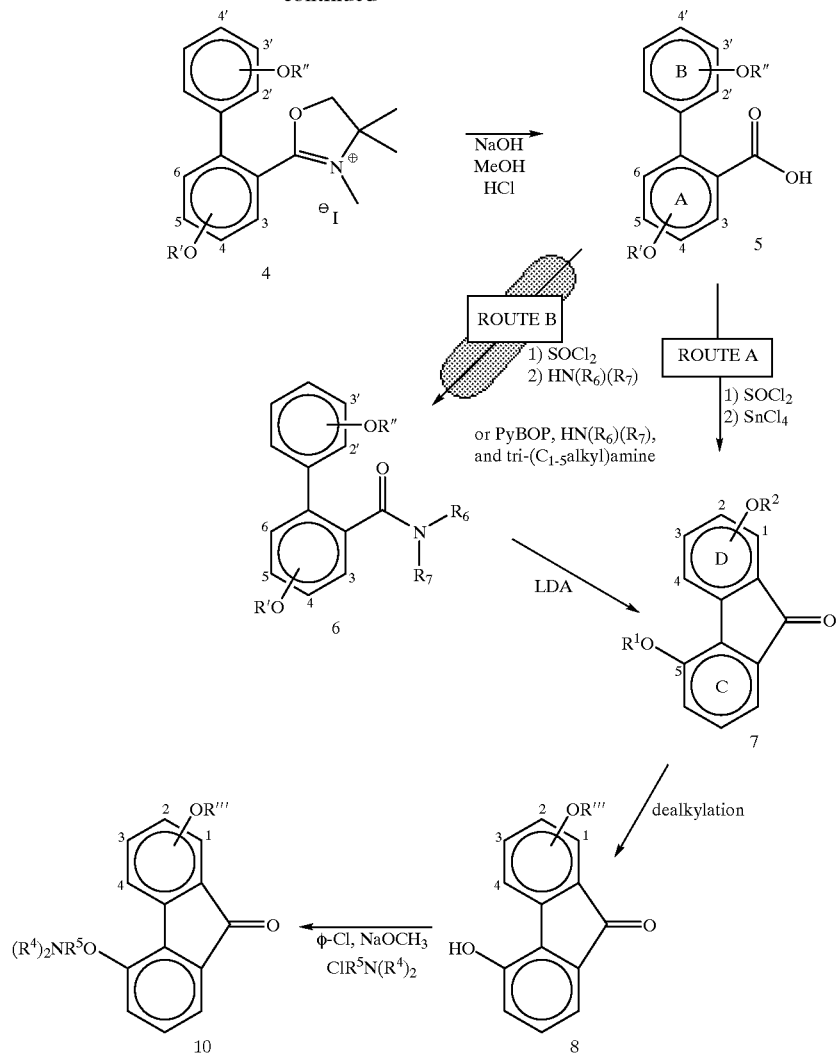

In Scheme 1 there is illustrated the synthesis of several compounds of the invention, including all of the bis-basic and certain mono-basic compounds, starting from the dialkoxy oxazoline [1]. In the dialkoxy oxazoline [1], OR' is present at either the 3, 4, or 5 positions as indicated in Scheme 1 and R' can represent any straight or branched chain $C_{1-4}$ alkyl radical. For example, methyl, ethyl, n-propyl, isopropyl, n-butyl, s-butyl, t-tutyl and the like, while methyl and isopropyl are preferred. R' is chosen so as to be easily eliminated upon reaction with the Grignard reagent of the halo-phenyl ether [2], to form the biphenyl oxazoline [3]. The reaction may be carried out in a manner consistent with the reaction shown in Meyers and Mihelich in *J. Amer. Chem. Soc.*, supra. In the halo-phenyl ether [2], X represents typical grignard halogens, such as bromo, chloro, iodo and the like, while bromo is preferred. OR" is present ortho, meta or para to the magnesium substituent and represents a similar scope of radicals as described by OR', wherein R' is methyl and n-propyl are preferred. Compounds [1] and [2] are reacted under typical Grignard conditions (anhydrous solvent) in a solvent in which the reactants and product biphenyl oxazoline are both soluable as well as non-reactive. For example, diethyl ether, tetrahydrofuran (THF), glyme, diglyme, etc.

The biphenyl oxazoline [3] is then converted into the biphenyl acid [5] in either one of two ways. Firstly, the conversion may occur in one step by application of acid and heat, which is the preferred method of choice in making the bis-basic compounds. The acid hydrolysis conversion may equally be employed when the ether linkages in OR' and OR" are relatively immune to acid hydrolysis, such as is the case when R' and R" are both methyl. Alternatively, the conversion may proceed via base hydrolysis, as reported by Ladd et al, *J. Med. Chem.* 29(10), 1904 (1986). This may be accomplished first by methylation and formation of the quaternary ammonium salt [4], such as with methyl iodide, and subsequently base hydrolysed under conditions suitable to obtain the corresponding biphenyl acid [5]. For example, sodium hydroxide and methanol may be used, followed by acidification.

The biphenyl acid [5] is then treated depending upon the location of the OR' and OR" alkoxy substituents. When ring A of [5] corresponds to ring C of [7] and B to D, respectively, the 1,5 (minor product), 2,5 or 3,5 fluorenone [7] is made by following Route A, while the 4,5 and 1,5 (major product) fluorenone [7] is made by following Route B. By way of example, Route A corresponds to those biphenyl acids [5] wherein OR" is present at either the 4' or 3' position, wherein Route B is used when OR" is a substituent at either the 2' or 3' position. R'O may be present at the 3, 4, 5 or 6 positions. The placement of one substituent, R'O and R"O, will affect the location of the other, as is described below.

It will be further realized that compound [7] is designated by $R^1$ and $R^2$ instead of R' and R", respectively. This occurs because, although the 6 position of compound [5] may correspond to the 5 position of compound [7], it need not necessarily, since the 2' position may also result as the 5 substituent of [7]. As a result, $R^1$ may be either R' or R" while $R^2$ may be either R" or R', meaning that ring B of [5] may also correspond to ring C of [7], while ring A corresponds to ring D, respectively. To illustrate, the 1,5 fluorenone [7] may be formed from either the 3',6 or 2',3 substituted biphenyl acid [5]. However, it will be appreciated that since the 5 position of compound [7] must contain an alkoxy substitution, whenever $R^1O$ is substituted at other than position 6 of the A ring of the biphenyl acid [5], then $R^2O$ will always be at the 2' position, and Route B must be followed. For example, the 2,5-fluorenone may be formed either via Route A from the 4',6 biphenyl acid [5], or via Route B from the 2',4 biphenyl acid [5].

Continuing, para or 4'-substituted B ring biphenyls [5] will cyclize under any suitable Friedel-Crafts conditions, for example, thionyl chloride, oxalyl chloride, $PCl_5$ followed by tin tetrachloride (preferred), TFAA, etc., to form para or 2-substituted fluorenones [7]. The exact choice and reaction parameters of suitable Friedlel-Crafts conditions are readily determinable by one of ordinary skill in the art. These suitable Friedel-Crafts conditions applied to meta or 3'-substituted B ring biphenyls will yield mixtures of both the 1 and 3-substituted fluorenones [7], with the 3-substituted product in quantitative excess.

As reported by J. Fu et al., *J. Org. Chem.,* 56(5), 1983 (1991), the carboxamide [6] cyclizes regiospecifically to form the 1-substituted fluorenone [7] from equivalent 3' substituted biphenyl acids [5]. Moreover, 2'-substituted biphenyl acids must be cyclized to the fluorenone via LDA condensation of the carboxamide [Route B], since typical Freidel-Crafts conditions will form a biphenylpyran instead of the desired fluorenone. T. Sala & M. V. Sargent, *J. Chem. Soc., Perkin Trans.* 1, 2593 (1979); M. V. Sargent, *J. Chem. Soc., Perkin Trans.* 1, 2553 (1987).

We have discovered that the carboxamide intermediate [6] can be prepared by immediately reacting the acid chloride (prepared from the biphenyl acid [5] by application of thionyl chloride) with an excess of an amine of the formula $HN(R_6)(R_7)$, wherein $R_6$ and $R_7$ are as defined above, preferably where $R_6$ and $R_7$ are ethyl, without significant formation of the biphenylpyran as is reported by Sargent, above. The acid chloride and subsequently the carboxamide may be formed in situ, whereupon the carboxamide is isolated and then reacted with LDA to get the fluorenone [7].

We have also discovered that the carboxaminde intermediate [6] can be prepared by immediately reacting the biphenyl acid [5] with PyBOP (Nova Biochem, San Diego, Calif.) in the presence of an amine of the formula $HN(R_6)(R_7)$, wherein $R_6$ and $R_7$ are as defined above, and a tri-$(C_{1-5}$ alkyl)amine, which acts as an acid scavenger. The reaction is typically carried out in a suitable organic solvent, for example, a chlorinated hydrocarbon, such as methylene chloride or carbon tetrachloride; a chlorinated aromatic, such as 1,2,4-trichlorobenzene; tetrahydrofuran; or an aromatic solvent, such as benzene; with methylene chloride being the preferred solvent. Examples of appropriate tri-$(C_{1-5}$ alkyl)amines include triethylamine, N,N-diisopropylethylamine, and the like, with N,N-diisopropylethylamine being preferred. The reaction is typically carried out over a period of time ranging from 6 to 25 hours. The carboxamide intermediate [6] is isolated and purified according to any appropriate technique, such as filtration, evaporation and flash chromatography.

The fluorenone [7] can then be dealkyated giving the 5-phenol [8], either completely as is the case when making the bis-basic compounds of the invention, or selectively as when mono-basic fluorenone compounds are desired. R'" is defined as $R^2$ or H. R'" would be hydrogen in the event of complete dealkylation, such as the case for the bis-basic fluorenones. The dealkylation conditions will vary depending upon $R^1$ and $R^2$ and are readily known to one of skill in the art. For example, complete dealkylation may be effected by the application of hydrogen bromide and heat in glacial acetic acid. Methoxy groups may be selectively dealkylated by diphenyl phosphine and n-butyl lithium, while isopropoxy groups can by dealkylated by boron trichloride. R. E. Ireland & D. M. Walba, *Organic Synthesis,* 56, p.44 (1977); T. Sala & M. V. Sargent, *J. Chem. Soc., Perkin Trans.* I, 2593 (1979). The 5-phenol [8] may then be alkylated with a reagent of the formula $X—R^5—N(R^4)_2$, as is disclosed in U.S. Pat. No. 3,592,819 to Fleming et al., and Andrews et al., *J. Med. Chem.* 17(8), 882 (1974). In the previous formula, X is halogen, $R^5$ is $C_{1-5}$ alkylene and $R^4$ is $C_{1-3}$ alkyl, or the $R^4$'s are combined to give pyrrolidinyl, piperidinyl or morpholino. Typically, the alkylation reaction is done in the presence of sodium methoxide in chloro-benzene and methanol in order to give the product fluorenones [10].

Alternatively, the carboxamide intermediate [6] may be prepared according to Scheme 1A, wherein the substituents, unless otherwise indicated, are defined as above.

Scheme 1A

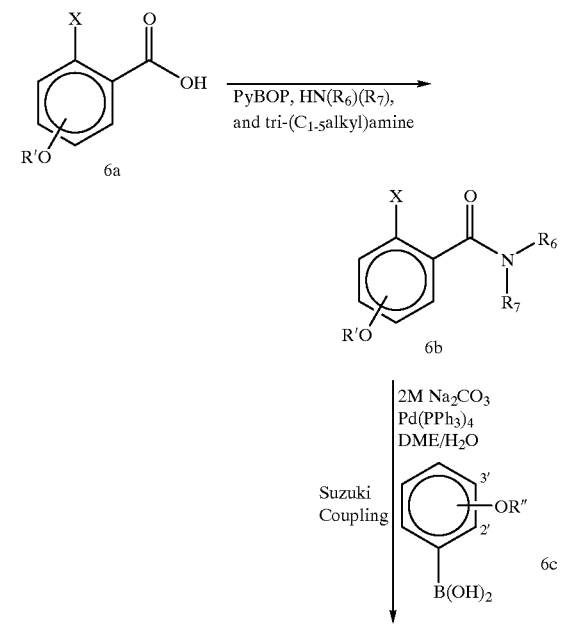

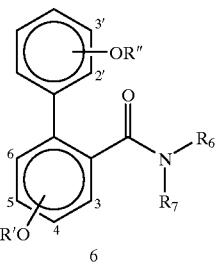

In Scheme 1A, the acid [6a] is condensed an amine of the formula $HN(R_6)(R_7)$, wherein $R_6$ and $R_7$ are as defined above at ambient temperature using PYBOP and an appropriate tri-$(C_{1-5}$ alkyl)amine, particularly N,N-diisopropylethyl-amine (DIEA), according to the procedure described in Scheme 1, Route B to give the amide [6b]. The reaction is preferably carried out in the presence of a suitable organic solvent, such as described above, peferably methylene chloride. The amide [6b] is then coupled with the aryl boronic acid [6c] utilizing a Suzuki coupling to provide the carboxamide intermediate [6]. N. Miyarura et al., *J. Org. Chem.* 51, 5467–5471 (1986); Y. Hoshino et al., *Bull. Chem. Soc. Japan* 61, 3008–3010; N. Miyaura et al., *J. Am. Chem. Soc.* 111, 314–321 (1989); W. J. Thompson et al., *J. Org. Chem.* 53, 2052–2055 (1988); and T. I. Wallow and B. M. Novak, *J. Org. Chem.* 59, 5034–5037 (1994).

For example, the amide [6b] is contacted with an appropriate aryl boronic acid [6c]. The Suzuki coupling reaction is performed in a suitable solvent, such as 1,2-dimethoxyethane (glyme). The reaction is performed using from about 1.1 to about 3 molar equivalents of an appropriate arylboronic acid. The reaction is carried out in the presence of from about 1 to about 3 molar equivalents of a suitable base, such as potassium carbonate or sodium carbonate. The coupling is performed using a suitable palladium catalyst, such as tetrakis(triphenyl-phosphine) palladium $[Pd(PPh_3)_4]$. The coupling is performed at a temperature ranging from 0° C. to the refluxing temperature of the solvent. The coupling reaction depicted in Scheme 1A may require from 6 hours to 14 days for reaction. The carboxamide intermediate [6] can be isolated and purified using techniques well known in the art. These techniques include extraction, evaporation, chromatography and recrystallization.

The approriate arylboronic acid [6c] is prepared by techniques and procedures well known and appreciated in the art. W. J. Thompson and J. Gaudino, *J. Org. Chem.*, 49, 5237–5243 (1984). Arylboronic acids are frequently contaminated with their corresponding anhydrides which do not perform well in the Suzuki coupling. Material contaminated by detrimental amounts of anhydride can be converted to the corresponding acid by hydrolysis. The hydrolysis is performed, if required, by briefly boiling in water and the arylboronic acid is recovered by filtration.

Scheme 2

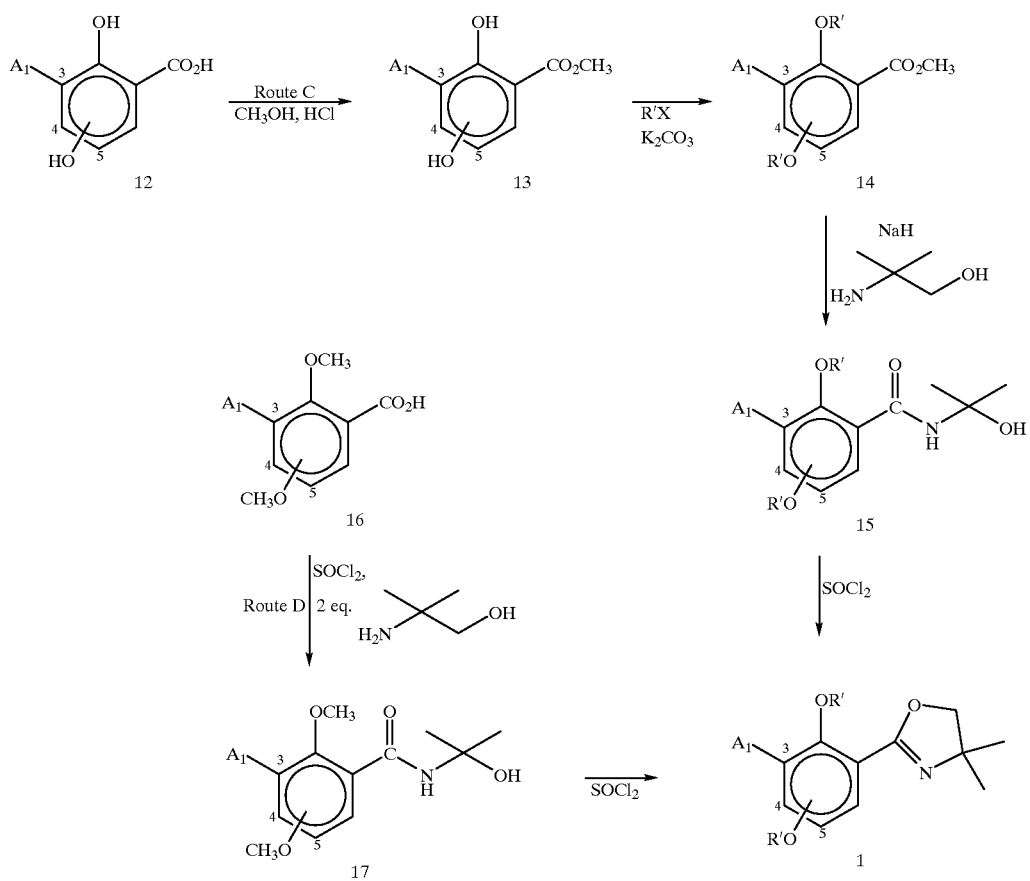

In Scheme 2, there is illustrated possible preparations of the starting dialkoxy oxazoline [1]. $A^1$ is as defined in Scheme 6A. Route C shows a diphenolic acid [12], available at the time this application was prepared from general chemical suppliers such as the Aldrich Chemical Co., Milwaukee, Wis. which is converted to the diphenolic methyl ester [13] in methanolic hydrogen chloride. Any known technique may be carried out such as, for example saturating a boiling methanol solution of the diphenol [12] with hydrogen chloride, King et al., *J. Chem. Soc.*, 4206 (1955). The diphenolic methyl ester [13] is then alkylated to the dialkyl methyl ester [14] such as by reaction with an haloalkane, wherein the alkyl portion is represented by R' as previously defined, and under typical conditions and solvents known in the art. The halogen may also be any of those typically used in alkyl substitution reactions, for example, bromo, chloro, iodo. While the above alkylation technique may be employed for the entire range of R', we have found it to be particularly preferable when R' is acid sensitive, such as isopropyl. The dialkyl methyl ester [14] is reacted with 2-amino-2-methylpropan-1-ol in the presence of sodium hydride in a suitable non-reactive solvent to obtain the hydroxy amide [15]. For example, Dodd et al., *Synthetic Communications*, 23(7), 1003 (1993) discloses an alkylation (corresponding to the conversion of [13] to [14] in Scheme 2) in the presence of potassium carbonate in toluene, followed by amidization with the amino-alcohol in tetrahydrofuran. The hydroxy amide [15] can then be converted into the dialkoxy oxazoline [1] by any known means. For example, by application of thionyl chloride as disclosed in Sargent, or through 2 molar equivalents each of triphenyl phosphine and N-(1,1-dimethyl-2-hydroxyethyl)-4'-dimethoxymethylbenzamide (DEAD) as described in Dodd et al.

Route D of Scheme 2 illustrates a simplified procedure for preparation of the dialkoxy oxazoline [1] when R' is methyl. As illustrated, when dimethoxy benzoic acids [16] are already readily available (also from Aldrich Chemical Co.), it is not necessary to synthesize them by creation of the methyl ether from the biphenolic acid [12]. The dimethoxy benzoic acid [16] is converted to the acid chloride by reaction with thionyl chloride, then reacted with at least two molar equivalents of 2-amino-2-methylpropan-1-ol to give the dimethoxycarboxamide [17]. The dimethoxycarboxamide [17] can then be converted into the dialkoxy oxazoline [1] by reaction with thionyl chloride. The formation of the oxazoline [1] can also by mediated by oxalyl chloride, phosphoryl chloride as well as other condensing reagants, such as for example Friedel-Crafts, etc.

Scheme 3

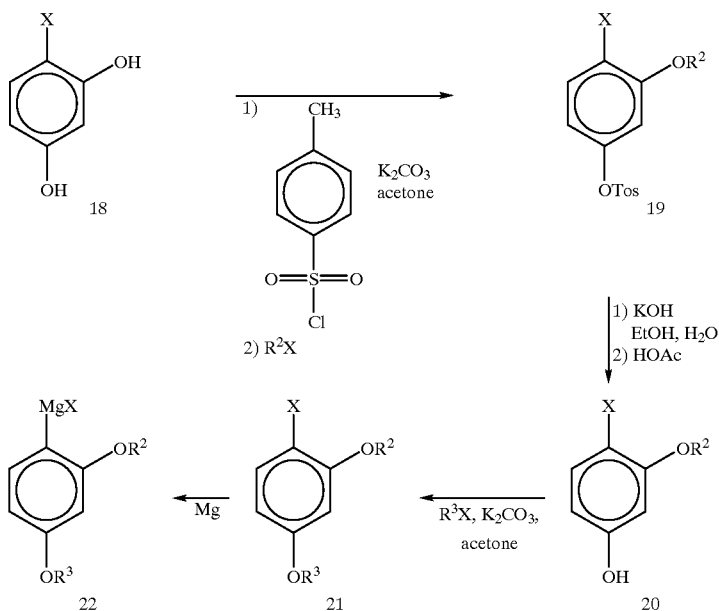

In Scheme 3, there is illustrated the preparation of the halo-dialkyl phenyl ether [21], and the corresponding Grignard [22] which is the starting compound used to make the dialkoxy substituted mono-basic fluorenone compounds of the invention. X is as defined under Scheme 1. The mono-alkyl substituted ether [2], which is used in Scheme 1, can be prepared by alkylation of the corresponding halo-phenol, as is known. In the preparation of the dialkyl ether [21], the reaction conditions for the conversion of the halo-biphenol [18] into the halo-dialkoxy phenyl ether [21] by selective alkylation of the hydroxy groups is also known in the art. For example, as described in Bose et al., *J. Am. Chem. Soc.*, 1991, 113, 9293, the halo-diphenol [18] is protected by alkylation with para-toluene sulfonyl chloride in the presence of potassium carbonate, carried out in an inert solvent such as acetone, 2-butanone, etc. The protected phenol is then reacted with an appropriate halo-alkyl compound, where the halogen portion is defined as before and the alkyl portion is defined by $R^2$, to form the protected halo-phenyl alkoxy ether [19]. The protected ether [19] is then deprotected first by basic and then acidic conditions to obtain the alkoxy phenol [20]. For example, potassium hydroxide in aqueous ethanol followed by acetic acid. The alkoxy phenol [20] may then by alkylated under analogous conditions as in the alkylation of Scheme 1, with alkyl being defined by $R^3$, in order to obtain the halo-dialkoxy phenyl ether [21]. $R^3$ is defined similarly to $R^1$ and $R^2$. The halo-dialkoxy phenyl ether [21] can be converted into the equivalent Grignard [22] by reaction with magnesium, in a suitable non-reactive solvent such as diethyl ether, tetrahydrofuran, etc., as is known.

Scheme 4

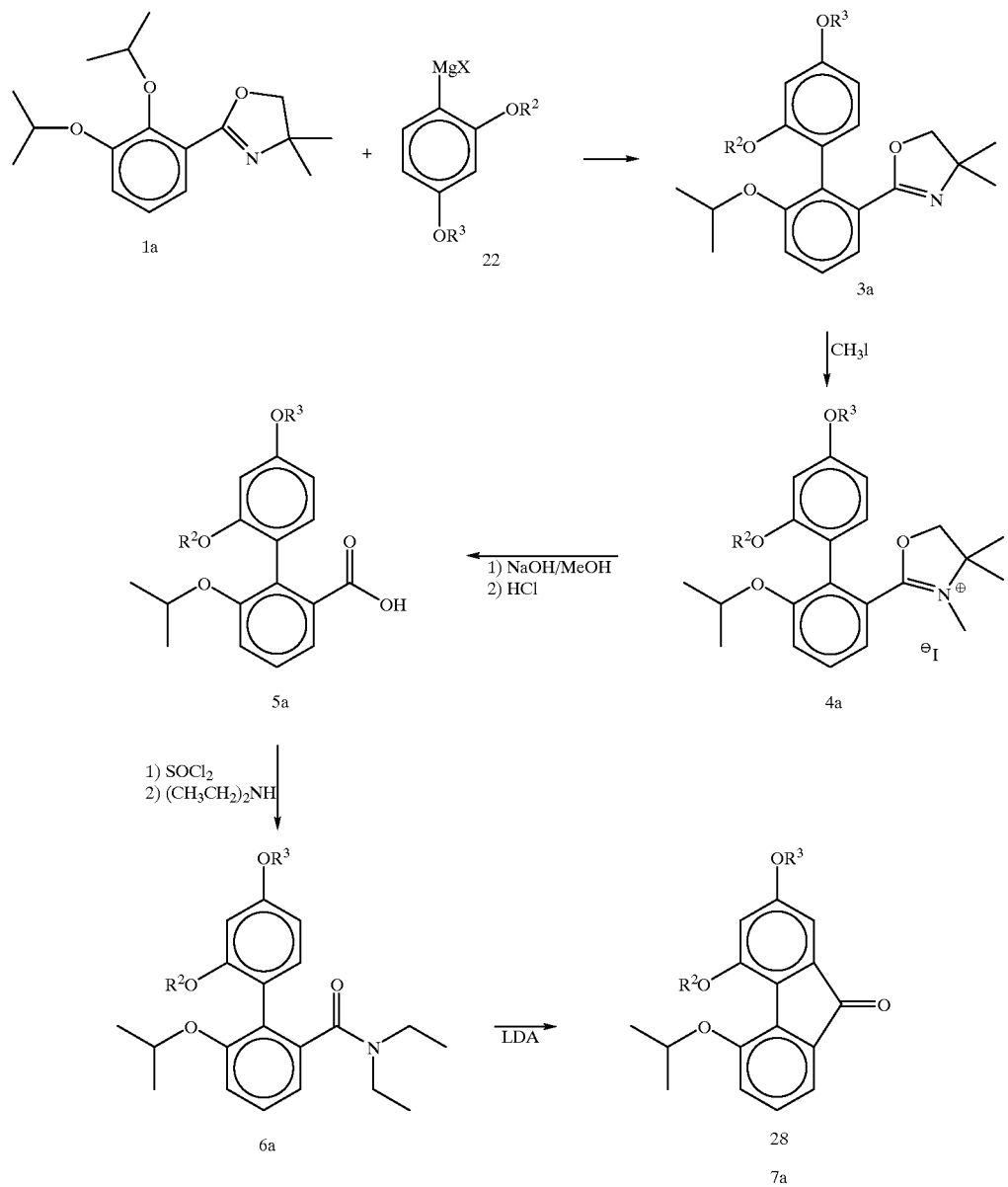

Scheme 4 illustrates the first part of the preferred synthesis of the trialkoxy-substituted 5-fluorenones of the invention. It is similar to Scheme 1, Route B Utilizing many of the same reagents as the former and differs from it principally in the use of the halo-dialkoxy phenyl ether grignard [22] prepared in Scheme 3 (as opposed to the monoalkoxy grignard [2]), as well as the limitation of R' to isopropyl. $R^2$ and $R^3$ are defined as before, as are the reaction conditions. The compounds in Scheme 4 are designated similarly (with an "a") as in Scheme 1 in order to indicate corresponding reaction conditions.

Scheme 5
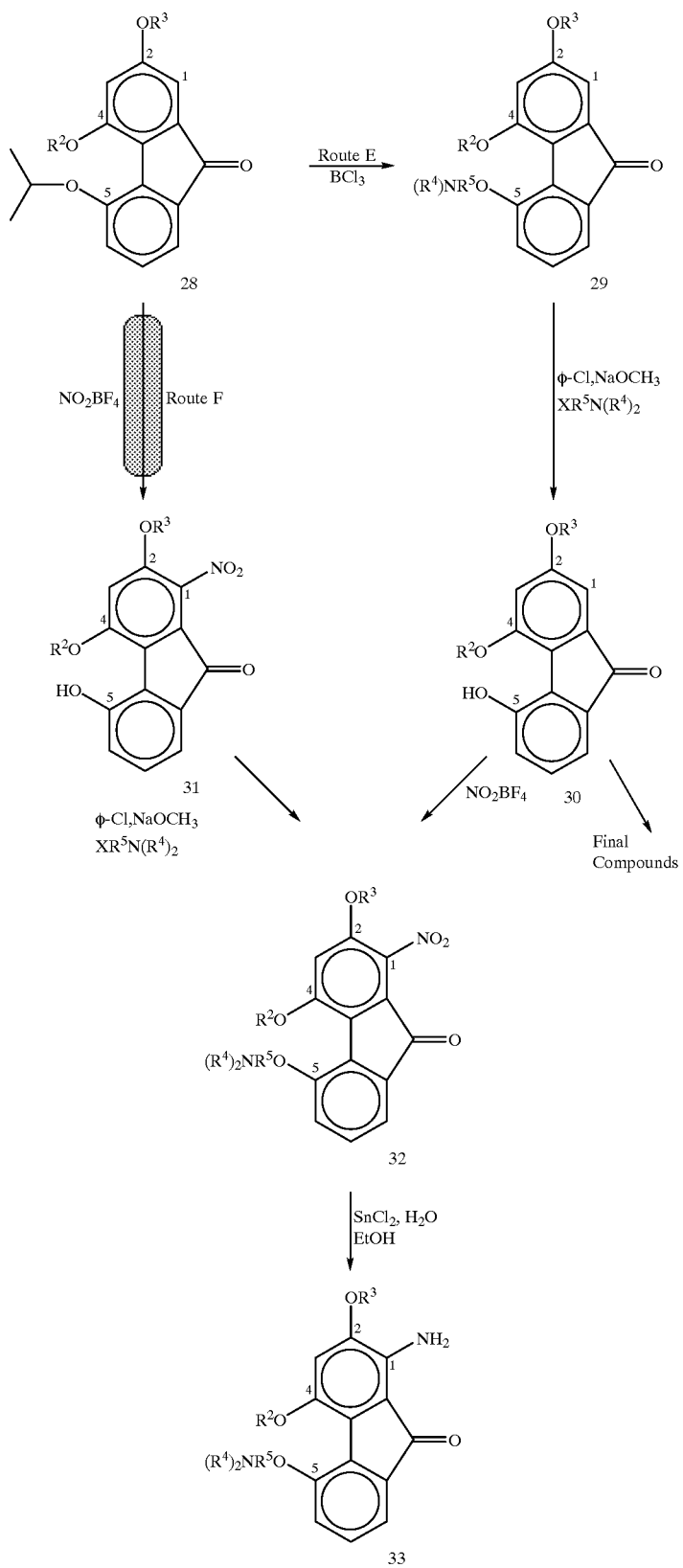

Scheme 5 illustrates the second part of the synthesis of the trialkoxy-substituted 5-fluorenones of the invention. The tri-ether [28] may be modified in two ways to obtain the compounds of the invention. Route E of Scheme 5 illustrates selective dealkylation of the 5-isopropoxy group to form the 5-phenol [29], by treatment with boron trichloride, in a suitable non-reactive solvent such as methylene chloride, as is described in Sargent, above. The 5-phenol [29] is then alkylated, by a compound of the formula X—$R^5$—$N(R^4)_2$ wherein X, $R^5$ and $R^4$ are as defined in Scheme 1, in the presence of chlorobenzene and sodium methoxide to obtain the 2,4-dialkoxy-5-alkoxy-dialkylamine [30], which can be both a final compound as well as an intermediate for the 1-nitro compound [32]. Compound 30, upon nitration with nitronium tetrafluoroborate in methylene chloride at −70° C. (allow warming to ambient temperature) gives the 1-nitro compound [32]. The 1-nitro compound [32] is then reduced into the 1-amine [33] by any effective means known in the art, while stannous chloride in ethanol is preferred. Additional reductive systems include for example, chemically by 1) zinc metal in acetic acid, 2) zinc metal in methanol either in the presence or absence of ammonium chloride, and 3) iron and acetic acid in ethanol.

Route F of Scheme 5 illustrates a novel synthesis of the 1-amine. We have discovered that when the nitrating step is applied first, the application of nitronium tetrafluoroborate to the tri-ether [28] has the effect of both nitrating as well as selectively dealkylating the 5-isopropoxy group to form the nitro-phenol [31]. The conditions of this reaction are similar to those used in Route E. Since the result is the elimination of a synthetic step vis-a-vis Route E, Route F is preferred. The nitro-phenol [31] is then alkylated with the appropriate 2-chloroethyl-dialkyl amine, under similar conditions to those explained previously, to give the 1-nitro compound [32]. As illustrated, the 1-nitro compound represents the convergence of Schemes E and F and is then reduced into the 1-amine as explained under Route E.

Alternatively, the 2,5-bis-basic fluorenone compounds of the invention may be obtained by the method described in U.S. Pat. No. 3,592,819 to Fleming et al. as well as by Andrews et al., *J. Med. Chem.*, 17:8, 882 (1974), wherein these compound were obtained by reduction, diazonation and hydrolytic displacement of the corresponding 2,5-dinitro-compound. The di-nitro compound can be obtained by nitrating fluorenone as is known.

Additionally, an appropriate 2,5-dimethoxyfluorene-9-one can be made according to Scheme 1A to obtain the appropriate intermediate of structure [6] and then according to Scheme 1 to obtain the desired final product.

Scheme 6A describes a synthesis of the bis-basic alkoxy compounds of the invention starting from either the dialkoxy oxazoline [1] or trialkoxyoxazoline [34]. Scheme 6A is analogous to Scheme 1, describing the synthesis of compounds 3–7, and similar reaction conditions may be employed here. $R^1$, $R^2$, $R_6$, $R_7$, R' and R" are as defined in Scheme 1. $R^8$ is methyl, ethyl, n-propyl, isopropyl, n-butyl, sec-butyl. $A^1$ and $A^2$ represent alternative routes for obtaining $R_6O$ in compound 40. That is, $R^8O$ may hie obtained from the alkoxy subsitutent ortho to the eliminated R'O substituent ($A_1$), or it may be obtained from an alkoxy substituent ortho to the phenyl-magnesium bond ($A_2$). $A_1$ and $A_2$ are mutually exclusive. That is when $A_1$ is present, $A_2$ is absent and vice versa.

Scheme 6B is the continuation of the synthesis started in Scheme 6A

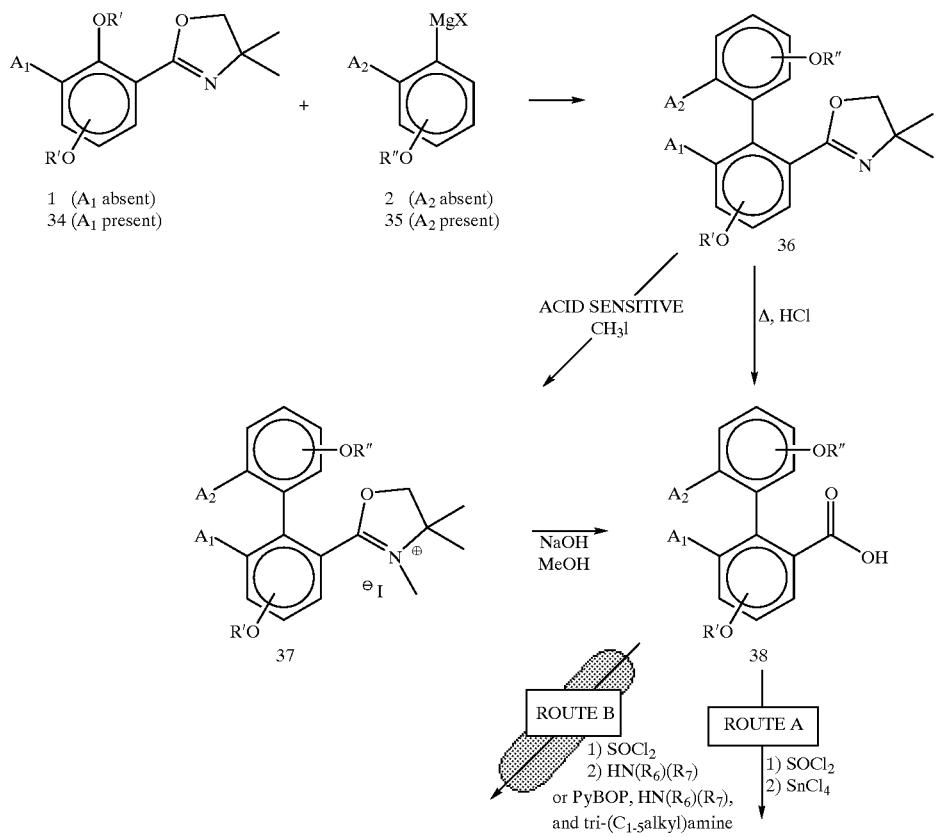

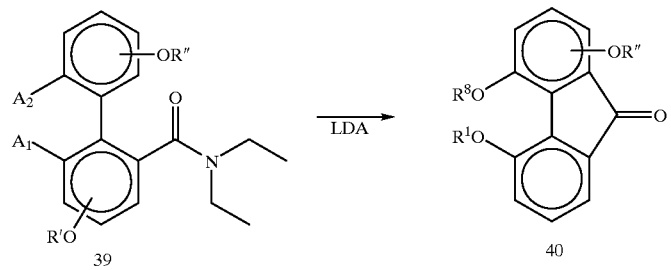

Scheme 6A starting from the tri-alkoxy fluorenone [40]. The reagents and reaction conditions are similar to those employed in Scheme 5. Route F of Scheme 5 is similar to Route G of Scheme 6B and employs similar reagents and reaction conditions. Route E of Scheme 5 is similar to and employs the corresponding reagents and reaction conditions as those described in Route G of Scheme 6B. Analogous compounds to those of Scheme 5 are identified with an "a", which follows the Scheme 5 compound. The compounds of Scheme 6B also have their own new numerical identification. Throughout Scheme 6A and 6B, variable definitions are as defined before.

Scheme 6B

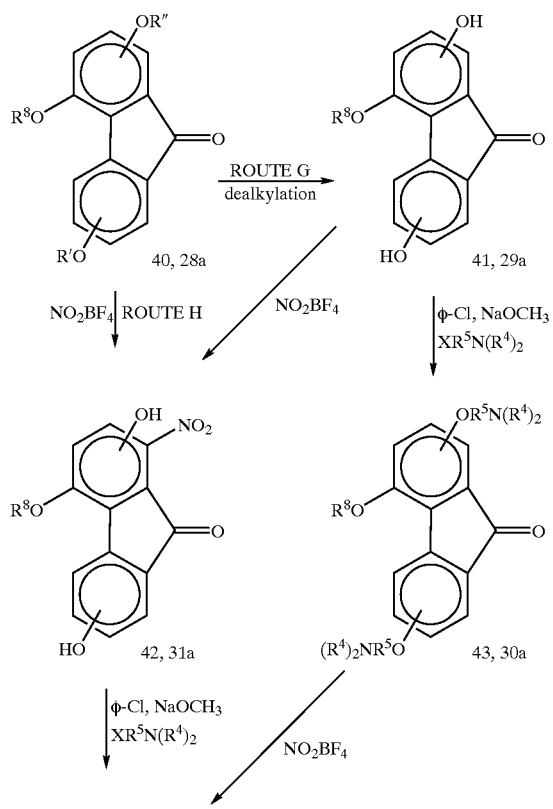

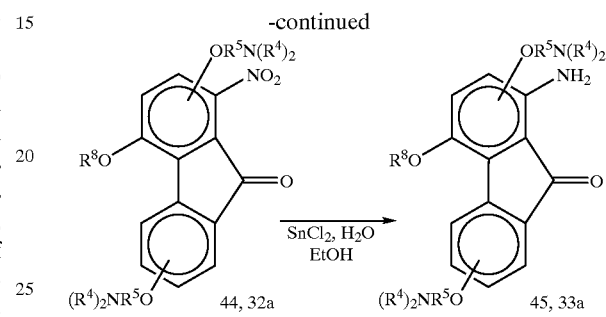

Examples of compounds of the present invention include the following 3,5-Bis-(2-diethylamino-ethoxy)-fluoren-9-one
1,5-Bis-(2-diethylamino-ethoxy)-fluoren-9-one
3,5-Bis-(2-dimethylamino-ethoxy)-fluoren-9-one
1,5-Bis-(2-dimethylamino-ethoxy)-fluoren-9-one
3,5-Bis-(3-diethylamino-propoxy)-fluoren-9-one
1,5-Bis-(3-diethylamino-propoxy)-fluoren-9-one
3,5-Bis-(4-diethylamino-n-butoxy)-fluoren-9-one
1,5-Bis-(4-diethylamino-n-butoxy)-fluoren-9-one
3,5-Bis-(2-pyrrolidinyl-ethoxy)-fluoren-9-one
1,5-Bis-(2-pyrrolidinyl-ethoxy)-fluoren-9-one
3,5-Bis-(pyrrolidinyl-methoxy)-fluoren-9-one
1,5-Bis-(pyrrolidinyl-methoxy)-fluoren-9-one
3,5-Bis-(3-pyrrolidinyl-propoxy)-fluoren-9-one
1,5-Bis-(2-pyrrolidinyl-propoxy)-fluoren-9-one
3,5-Bis-(4-pyrrolidinyl-n-butoxy)-fluoren-9-one
1,5-Bis-(4-pyrrolidinyl-n-butoxy)-fluoren-9-one
3,5-Bis-(2-piperidinyl-ethoxy)-fluoren-9-one
1,5-Bis-(2-piperidinyl-ethoxy)-fluoren-9-one
3,5-Bis-(piperidinyl-methoxy)-fluoren-9-one
1,5-Bis-(piperidinyl-methoxy)-fluoren-9-one
3,5-Bis-(3-piperidinyl-propoxy)-fluoren-9-one
1,5-Bis-(3-piperidinyl-propoxy)-fluoren-9-one
3,5-Bis-(4-piperidinyl-n-butoxy)-fluoren-9-one
1,5-Bis-(4-piperidinyl-n-butoxy)-fluoren-9-one
3,5-Bis-[2-(morpholino-4-yl)-ethoxy]-fluoren-9-one
1,5-Bis-[2-(morpholino-4-yl)-ethoxy]-fluoren-9-one
3,5-Bis-[(morpholino-4-yl)-methoxy]-fluoren-9-one
1,5-Bis-[(morpholino-4-yl)-methoxy]-fluoren-9-one
3,5-Bis-[3-(morpholino-4-yl)-propoxy]-fluoren-9-one
1,5-Bis-[3-(morpholino-4-yl)-propoxy]-fluoren-9-one
3,5-Bis-[4-(morpholino-4-yl)-n-butoxy]-fluoren-9-one
1,5-Bis-[4-(morpholino-4-yl)-n-butoxy]-fluoren-9-one
1,5-Bis-(2-diethylamino-ethoxy)-4-methoxy-fluoren-9-one
1,5-Bis-(2-diethylamino-ethoxy)-4-ethoxy-fluoren-9-one 1,5-Bis-(2-diethylamino-ethoxy)-4-propoxy-fluoren-9-one
1,5-Bis-(2-diethylamino-ethoxy)-4-n-butoxy-fluoren-9-one
1,5-Bis-(3-diethylamino-propoxy)-4-methoxy-fluoren-9-one
1,5-Bis-(3-diethylamino-propoxy)-4-ethoxy-fluoren-9-one
1,5-Bis-(3-diethylamino-propoxy)-4-propoxy-fluoren-9-one
1,5-Bis-(3-diethylamino-propoxy)-4-n-butoxy-fluoren-9-one
1,5-Bis-(2-pyrrolidinyl-ethoxy)-4-methoxy-fluoren-9-one
1,5-Bis-(2-pyrrolidinyl-ethoxy)-4-ethoxy-fluoren-9-one
1,5-Bis-(2-pyrrolidinyl-ethoxy)-4-propoxy-fluoren-9-one
1,5-Bis-(2-pyrrolidinyl-ethoxy)-4-n-butoxy-fluoren-9-one
1,5-Bis-(3-pyrrolidinyl-propoxy)-4-methoxy-fluoren-9-one
1,5-Bis-(3-pyrrolidinyl-propoxy)-4-ethoxy-fluoren-9-one
1,5-Bis-(3-pyrrolidinyl-propoxy)-4-propoxy-fluoren-9-one
1,5-Bis-(3-pyrrolidinyl-propoxy)-4-n-butoxy-fluoren-9-one
1,5-Bis-(2-piperidinyl-ethoxy)-4-methoxy-fluoren-9-one
1,5-Bis-(2-piperidinyl-ethoxy)-4-ethoxy-fluoren-9-one
1,5-Bis-(2-piperidinyl-ethoxy)-4-propoxy-fluoren-9-one
1,5-Bis-(2-piperidinyl-ethoxy)-4-n-butoxy-fluoren-9-one
1,5-Bis-(3-piperidinyl-propoxy)-4-methoxy-fluoren-9-one
1,5-Bis-(3-piperidinyl-propoxy)-4-ethoxy-fluoren-9-one
1,5-Bis-(3-piperidinyl-propoxy)-4-propoxy-fluoren-9-one
1,5-Bis-(3-piperidinyl-propoxy)-4-n-butoxy-fluoren-9-one
1,5-Bis-(3-piperidinyl-propoxy)-4-methoxy-fluoren-9-one
1,5-Bis-[2-(morpholino-4-yl)-ethoxy]-4-methoxy-fluoren-9-one
1,5-Bis-[2-(morpholino-4-yl)-ethoxy]-4-ethoxy-fluoren-9-one
1,5-Bis-[2-(morpholino-4-yl)-ethoxy]-4-propoxy-fluoren-9-one
1,5-Bis-[2-(morpholino-4-yl)-ethoxy]-4-n-butoxy-fluoren-9-one
1,5-Bis-[3-(morpholino-4-yl)-propoxy]-4-methoxy-fluoren-9-one
1,5-Bis-[3-(morpholino-4-yl)-propoxy]-4-ethoxy-fluoren-9-one
1,5-Bis-[3-(morpholino-4-yl)-propoxy]-4-propoxy-fluoren-9-one
1,5-Bis-[3-(morpholino-4-yl)-propoxy]-4-n-butoxy-fluoren-9-one
2,5-Bis-(2-diethylamino-ethoxy)-4-methoxy-fluoren-9-one
2,5-Bis-(2-diethylamino-ethoxy)-4-ethoxy-fluoren-9-one
2,5-Bis-(2-diethylamino-ethoxy)-4-propoxy-fluoren-9-one
2,5-Bis-(2-diethylamino-ethoxy)-4-n-butoxy-fluoren-9-one
2,5-Bis-(3-diethylamino-propoxy)-4-methoxy-fluoren-9-one
2,5-Bis-(3-diethylamino-propoxy)-4-ethoxy-fluoren-9-one
2,5-Bis-(3-diethylamino-propoxy)-4-propoxy-fluoren-9-one
2,5-Bis-(3-diethylamino-propoxy)-4-n-butoxy-fluoren-9-one
2,5-Bis-(2-pyrrolidinyl-ethoxy)-4-methoxy-fluoren-9-one
2,5-Bis-(2-pyrrolidinyl-ethoxy)-4-ethoxy-fluoren-9-one
2,5-Bis-(2-pyrrolidinyl-ethoxy)-4-propoxy-fluoren-9-one
2,5-Bis-(2-pyrrolidinyl-ethoxy)-4-n-butoxy-fluoren-9-one
2,5-Bis-(3-pyrrolidinyl-propoxy)-4-methoxy-fluoren-9-one
2,5-Bis-(3-pyrrolidinyl-propoxy)-4-ethoxy-fluoren-9-one
2,5-Bis-(3-pyrrolidinyl-propoxy)-4-propoxy-fluoren-9-one
2,5-Bis-(3-pyrrolidinyl-propoxy)-4-n-butoxy-fluoren-9-one
2,5-Bis-(2-piperidinyl-ethoxy)-4-methoxy-fluoren-9-one
2,5-Bis-(2-piperidinyl-ethoxy)-4-ethoxy-fluoren-9-one
2,5-Bis-(2-piperidinyl-ethoxy)-4-propoxy-fluoren-9-one
2,5-Bis-(2-piperidinyl-ethoxy)-4-n-butoxy-fluoren-9-one
2,5-Bis-(3-piperidinyl-propoxy)-4-methoxy-fluoren-9-one
2,5-Bis-(3-piperidinyl-propoxy)-4-ethoxy-fluoren-9-one
2,5-Bis-(3-piperidinyl-propoxy)-4-propoxy-fluoren-9-one
2,5-Bis-(3-piperidinyl-propoxy)-4-n-butoxy-fluoren-9-one
2,5-Bis-[2-(morpholino-4-yl)-ethoxy]-4-methoxy-fluoren-9-one
2,5-Bis-[2-(morpholino-4-yl)-ethoxy]-4-ethoxy-fluoren-9-one
2,5-Bis-[2-(morpholino-4-yl)-ethoxy]-4-propoxy-fluoren-9-one
2,5-Bis-[2-(morpholino-4-yl)-ethoxy]-4-n-butoxy-fluoren-9-one
2,5-Bis-[3-(morpholino-4-yl)-propoxy]-4-methoxy-fluoren-9-one
2,5-Bis-[3-(morpholino-4-yl)-propoxy]-4-ethoxy-fluoren-9-one
2,5-Bis-[3-(morpholino-4-yl)-propoxy]-4-propoxy-fluoren-9-one
2,5-Bis-[3-(morpholino-4-yl)-propoxy]-4-n-butoxy-fluoren-9-one
1-Amino-2,5-bis-(2-diethylamino-ethoxy)-4-methoxy-fluoren-9-one
1-Amino-2,5-bis-(2-diethylamino-ethoxy)-4-ethoxy-fluoren-9-one
1-Amino-2,5-bis-(2-diethylamino-ethoxy)-4-propoxy-fluoren-9-one
1-Amino-2,5-bis-(2-diethylamino-ethoxy)-4-n-butoxy-fluoren-9-one
1-Amino-2,5-bis-(3-diethylamino-propoxy)-4-methoxy-fluoren-9-one
1-Amino-2,5-bis-(3-diethylamino-propoxy)-4-ethoxy-fluoren-9-one
1-Amino-2,5-bis-(3-diethylamino-propoxy)-4-propoxy-fluoren-9-one
1-Amino-2,5-bis-(3-diethylamino-propoxy)-4-n-butoxy-fluoren-9-one
1-Amino-2,5-bis-(2-pyrrolidinyl-ethoxy)-4-methoxy-fluoren-9-one
1-Amino-2,5-bis-(2-pyrrolidinyl-ethoxy)-4-ethoxy-fluoren-9-one
1-Amino-2,5-bis-(2-pyrrolidinyl-ethoxy)-4-propoxy-fluoren-9-one
1-Amino-2,5-bis-(2-pyrrolidinyl-ethoxy)-4-n-butoxy-fluoren-9-one
1-Amino-2,5-bis-(3-pyrrolidinyl-propoxy)-4-methoxy-fluoren-9-one
1-Amino-2,5-bis-(3-pyrrolidinyl-propoxy)-4-ethoxy-fluoren-9-one
1-Amino-2,5-bis-(3-pyrrolidinyl-propoxy)-4-propoxy-fluoren-9-one
1-Amino-2,5-bis-(3-pyrrolidinyl-propoxy)-4-n-butoxy-fluoren-9-one
1-Amino-2,5-bis-(2-piperidinyl-ethoxy)-4-methoxy-fluoren-9-one
1-Amino-2,5-bis-(2-piperidinyl-ethoxy)-4-ethoxy-fluoren-9-one
1-Amino-2,5-bis-(2-piperidinyl-ethoxy)-4-propoxy-fluoren-9-one
1-Amino-2,5-bis-(2-piperidinyl-ethoxy)-4-n-butoxy-fluoren-9-one
1-Amino-2,5-bis-(3-piperidinyl-propoxy)-4-methoxy-fluoren-9-one
1-Amino-2,5-bis-(3-piperidinyl-propoxy)-4-ethoxy-fluoren-9-one
1-Amino-2,5-bis-(3-piperidinyl-propoxy)-4-propoxy-fluoren-9-one
1-Amino-2,5-bis-(3-piperidinyl-propoxy)-4-n-butoxy-fluoren-9-one
1-Amino-2,5-bis-[2-(morpholino-4-yl)-ethoxy]-4-methoxy-fluoren-9-one
1-Amino-2,5-bis-[2-(morpholino-4-yl)-ethoxy]-4-ethoxy-fluoren-9-one 1-Amino-2,5-bis-[2-(morpholino-4-yl)-ethoxy]-4-propoxy-fluoren-9-one
1-Amino-2,5-bis-[2-(morpholino-4-yl)-ethoxy]-4-n-butoxy-fluoren-9-one
1-Amino-2,5-bis-[3-(morpholino-4-yl)-propoxy]-4-methoxy-fluoren-9-one
1-Amino-2,5-bis-[3-(morpholino-4-yl)-propoxy]-4-ethoxy-fluoren-9-one
1-Amino-2,5-bis-[3-(morpholino-4-yl)-propoxy]-4-propoxy-fluoren-9-one
1-Amino-2,5-bis-[3-(morpholino-4-yl)-propoxy]-4-n-butoxy-fluoren-9-one
5-(2-Diethylamino-ethoxy)-2-methoxy-fluoren-9-one
5-(3-Diethylamino-propoxy)-2-methoxy-fluoren-9-one
5-(2-Pyrrolidinyl-ethoxy)-2-methoxy-fluoren-9-one
5-(3-Pyrrolidinyl-propoxy)-2-methoxy-fluoren-9-one
5-(2-Piperidinyl-ethoxy)-2-methoxy-fluoren-9-one
5-(2-Piperidinyl-propoxy)-2-methoxy-fluoren-9-one
5-[2-(Morpholino-4-yl)-ethoxy]-2-methoxy-fluoren-9-one
5-[2-(Morpholino-4-yl)-propoxy]-2-methoxy-fluoren-9-one
5-(2-Diethylamino-ethoxy)-2-ethoxy-fluoren-9-one
5-(3-Diethylamino-propoxy)-2-ethoxy-fluoren-9-one
5-(2-Pyrrolidinyl-ethoxy)-2-ethoxy-fluoren-9-one
5-(3-Pyrrolidinyl-propoxy)-2-ethoxy-fluoren-9-one
5-(2-Piperidinyl-ethoxy)-2-ethoxy-fluoren-9-one
5-(2-Piperidinyl-propoxy)-2-ethoxy-fluoren-9-one
5-[2-(Morpholino-4-yl)-ethoxy]-2-ethoxy-fluoren-9-one
5-[2-(Morpholino-4-yl)-propoxy]-2-ethoxy-fluoren-9-one
5-(2-Diethylamino-ethoxy)-2-propoxy-fluoren-9-one
5-(3-Diethylamino-propoxy)-2-propoxy-fluoren-9-one
5-(2-Pyrrolidinyl-ethoxy)-2-propoxy-fluoren-9-one
5-(3-Pyrrolidinyl-propoxy)-2-propoxy-fluoren-9-one
5-(2-Piperidinyl-ethoxy)-2-propoxy-fluoren-9-one
5-(2-Piperidinyl-propoxy)-2-propoxy-fluoren-9-one
5-[2-(Morpholino-4-yl)-ethoxy]-2-propoxy-fluoren-9-one
5-[2-(Morpholino-4-yl)-propoxy]-2-propoxy-fluoren-9-one
5-(2-Diethylamino-ethoxy)-2-n-butoxy-fluoren-9-one
5-(3-Diethylamino-propoxy)-2-n-butoxy-fluoren-9-one
5-(2-Pyrrolidinyl-ethoxy)-2-n-butoxy-fluoren-9-one
5-(3-Pyrrolidinyl-propoxy)-2-n-butoxy-fluoren-9-one
5-(2-Piperidinyl-ethoxy)-2-n-butoxy-fluoren-9-one
5-(3-Piperidinyl-propoxy)-2-n-butoxy-fluoren-9-one
5-[2-(Morpholino-4-yl)-ethoxy]-2-n-butoxy-fluoren-9-one
5-[3-(Morpholino-4-yl)-propoxy]-2-n-butoxy-fluoren-9-one
4-(2-Diethylamino-ethoxy)-5-methoxy-fluoren-9-one
4-(3-Diethylamino-propoxy)-5-methoxy-fluoren-9-one
4-(2-Pyrrolidinyl-ethoxy)-5-methoxy-fluoren-9-one
4-(3-Pyrrolidinyl-propoxy)-5-methoxy-fluoren-9-one
4-(2-Piperidinyl-ethoxy)-5-methoxy-fluoren-9-one
4-(3-Piperidinyl-propoxy)-5-methoxy-fluoren-9-one
4-[2-(Morpholino-4-yl)-ethoxy]-5-methoxy-fluoren-9-one
4-[3-(Morpholino-4-yl)-propoxy]-5-methoxy-fluoren-9-one
4-(2-Diethylamino-ethoxy)-5-ethoxy-fluoren-9-one
4-(3-Diethylamino-propoxy)-5-ethoxy-fluoren-9-one
4-(2-Pyrrolidinyl-ethoxy)-5-ethoxy-fluoren-9-one
4-(3-Pyrrolidinyl-propoxy)-5-ethoxy-fluoren-9-one
4-(2-Piperidinyl-ethoxy)-5-ethoxy-fluoren-9-one
4-(3-Piperidinyl-propoxy)-5-ethoxy-fluoren-9-one
4-[2-(Morpholino-4-yl)-ethoxy]-5-ethoxy-fluoren-9-one
4-[3-(Morpholino-4-yl)-propoxy]-5-ethoxy-fluoren-9-one
4-(2-Diethylamino-ethoxy)-5-propoxy-fluoren-9-one
4-(3-Diethylamino-propoxy)-5-propoxy-fluoren-9-one
4-(2-Pyrrolidinyl-ethoxy)-5-propoxy-fluoren-9-one
4-(3-Pyrrolidinyl-propoxy)-5-propoxy-fluoren-9-one
4-(2-Piperidinyl-ethoxy)-5-propoxy-fluoren-9-one
4-(3-Piperidinyl-propoxy)-5-propoxy-fluoren-9-one
4-[2-(Morpholino-4-yl)-ethoxy)-5-propoxy-fluoren-9-one
4-[3-(Morpholino-4-yl)-propoxy]-5-propoxy-fluoren-9-one
4-(2-Diethylamino-ethoxy)-5-n-butoxy-fluoren-9-one
4-(3-Diethylamino-propoxy)-5-n-butoxy-fluoren-9-one
4-(2-Pyrrolidinyl-ethoxy)-5-n-butoxy-fluoren-9-one
4-(3-Pyrrolidinyl-propoxy)-5-n-butoxy-fluoren-9-one
4-(2-Piperidinyl-ethoxy)-5-n-butoxy-fluoren-9-one
4-(2-Piperidinyl-propoxy)-5-n-butoxy-fluoren-9-one
4-[2-Morpholino4yl)-ethoxy]-5-n-butoxy-fluoren-9-one
4-[3-(Morpholino-4-yl)-ethoxy]-5-n-butoxy-fluoren-9-one
5-(2-Diethylamino-ethoxy)-2-ethoxy-4-methoxy-fluoren-9-one
5-(2-Diethylamino-ethoxy)-2-ethoxy-4-propoxy-fluoren-9-one
5-(2-Diethylamino-ethoxy)-2-ethoxy-4-n-butoxy-fluoren-9-one
5-(2-Pyrrolidinyl-ethoxy)-2-ethoxy-4-methoxy-fluoren-9-one
5-(2-Piperidinyl-ethoxy)-2-ethoxy-4-methoxy-fluoren-9-one
5-[2-(Morpholino-4-yl)-ethoxy]-2-ethoxy-4-methoxy-fluoren-9-one
5-(2-Pyrrolidinyl-ethoxy)-2-ethoxy-4-ethoxy-fluoren-9-one
5-(2-Piperidinyl-ethoxy)-2-ethoxy-4-ethoxy-fluoren-9-one
5-[2-(Morpholino-4-yl)-ethoxy]-2-ethoxy-4-ethoxy-fluoren-9-one
5-(2-Pyrrolidinyl-ethoxy)-2-ethoxy-4-propoxy-fluoren-9-one
5-(2-Piperidinyl-ethoxy)-2-ethoxy-4-propoxy-fluoren-9-one
5-[2-(Morpholino-4-yl)-ethoxy]-2-ethoxy-4-propoxy-fluoren-9-one
5-(2-Diethylamino-ethoxy)-2-methoxy-4-ethoxy-fluoren-9-one
5-(2-Diethylamino-ethoxy)-2-methoxy-4-propoxy-fluoren-9-one
5-(2-Diethylamino-ethoxy)-2-methoxy-4-n-butoxy-fluoren-9-one
5-(2-Pyrrolidinyl-ethoxy)-2-methoxy-4-ethoxy-fluoren-9-one
5-(2-Piperidinyl-ethoxy)-2-methoxy-4-ethoxy-fluoren-9-one
5-[2-(Morpholino-4-yl)-ethoxy]-2-methoxy-4-ethoxy-fluoren-9-one
5-(2-Pyrrolidinyl-ethoxy)-2-methoxy-4-propoxy-fluoren-9-one
5-(2-Piperidinyl-ethoxy)-2-methoxy-4-propoxy-fluoren-9-one
5-[2-(Morpholino-4-yl)-ethoxy]-2-methoxy-4-propoxy-fluoren-9-one
5-(2-Diethylamino-ethoxy)-2-propoxy-4-ethoxy-fluoren-9-one
5-(2-Diethylamino-ethoxy)-2-propoxy-4-methoxy-fluoren-9-one
5-(2-Diethylamino-ethoxy)-2-propoxy-4-n-butoxy-fluoren-9-one
5-(2-Pyrrolidinyl-ethoxy)-2-propoxy-4-ethoxy-fluoren-9-one
5-(2-Piperidinyl-ethoxy)-2-propoxy-4-ethoxy-fluoren-9-one
5-[2-(Morpholino-4-yl)-ethoxy]-2-propoxy-4-ethoxy-fluoren-9-one
5-(2-Pyrrolidinyl-ethoxy)-2-propoxy-4-methoxy-fluoren-9-one
5-(2-Piperidinyl-ethoxy)-2-propoxy-4-methoxy-fluoren-9-one
5-[2-(Morpholino-4-yl)-ethoxy]-2-propoxy-4-methoxy-fluoren-9-one
5-(3-Diethylamino-ethoxy)-2,4-dimethoxy-fluoren-9-one
5-(3-Diethylamino-propoxy)-2,4-dimethoxy-fluoren-9-one 5-(2-Pyrrolidinyl-ethoxy)-2,4-dimethoxy-fluoren-9-one
5-(3-Pyrrolidinyl-propoxy)-2,4-dimethoxy-fluoren-9-one
5-(2-Piperidinyl-ethoxy)-2,4-dimethoxy-fluoren-9-one
5-(3-Piperidinyl-propoxy)-2,4-dimethoxy-fluoren-9-one
5-[2-(Morpholino-4-yl)-ethoxy]-2,4-dimethoxy-fluoren-9-one
5-[3-(Morpholino-4-yl)-propoxy]-2,4-dimethoxy-fluoren-9-one
5-(2-Diethylamino-ethoxy)-2,4-diethoxy-fluoren-9-one
5-(3-Diethylamino-propoxy)-2,4-diethoxy-fluoren-9-one
5-(2-Pyrrolidinyl-ethoxy)-2,4-diethoxy-fluoren-9-one
5-(3-Pyrrolidinyl-propoxy)-2,4-diethoxy-fluoren-9-one
5-(3-Piperidinyl-propoxy)-2,4-diethoxy-fluoren-9-one
5-(2-Piperidinyl-ethoxy)-2,4-diethoxy-fluoren-9-one
5-[2-(Morpholino-4-yl)-ethoxy]-2,4-diethoxy-fluoren-9-one
5-[3-(Morpholino-4-yl)-propoxy]-2,4-diethoxy-fluoren-9-one
5-(2-Diethylamino-ethoxy)-2,4-dipropoxy-fluoren-9-one
5-(3-Diethylamino-propoxy)-2,4-dipropoxy-fluoren-9-one
5-(2-Pyrrolidinyl-ethoxy)-2,4-dipropoxy-fluoren-9-one
5-(3-Pyrrolidinyl-propoxy)-2,4-dipropoxy-fluoren-9-one
5-(2-Piperidinyl-ethoxy)-2,4-dipropoxy-fluoren-9-one
5-(3-Piperidinyl-propoxy)-2,4-dipropoxy-fluoren-9-one
5-[2-(Morpholino-4-yl)-ethoxy]-2,4-dipropoxy-fluoren-9-one
5-[3-(Morpholino-4-yl)-propoxy-2,4-dipropoxy-fluoren-9-one 1-Amino-5-(2-diethylamino-ethoxy)-2-ethoxy-4-methoxy-fluoren-9-one
1-Amino-5-(2-diethylamino-ethoxy)-2-ethoxy-4-propoxy-fluoren-9-one
1-Amino-5-(2-diethylamino-ethoxy)-2-ethoxy-4-n-butoxy-fluoren-9-one
1-Amino-5-(2-pyrrolidinyl-ethoxy)-2-ethoxy-4-methoxy-fluoren-9-one
1-Amino-5-(2-pyridinyl-ethoxy)-2-ethoxy-4-methoxy-fluoren-9-one
1-Amino-5-[2-(morpholino-4-yl)-ethoxy]-2-ethoxy-4-methoxy-fluoren-9-one
1-Amino-5-(2-pyrrolidinyl-ethoxy)-2-ethoxy-4-propoxy-fluoren-9-one
1-Amino-5-(2-pyridinyl-ethoxy)-2-ethoxy-4-propoxy-fluoren-9-one
1-Amino-5-[2-(morpholino-4-yl)-ethoxy]-2-ethoxy-4-propoxy-fluoren-9-one
1-Amino-5-(2-diethylamino-ethoxy)-2-methoxy-4-ethoxy-fluoren-9-one
1-Amino-5-(2-diethylamino-ethoxy)-2-methoxy-4-propoxy-fluoren-9-one
1-Amino-5-(2-diethylamino-ethoxy)-2-methoxy-4-n-butoxy-fluoren-9-one
1-Amino-5-(2-pyrrolidinyl-ethoxy)-2-methoxy-4-ethoxy-fluoren-9-one
1-Amino-5-(2-pyridinyl-ethoxy)-2-methoxy-4-ethoxy-fluoren-9-one
1-Amino-5-[2-(morpholino-4-yl)-ethoxy]-2-methoxy-4-ethoxy-fluoren-9-one
1-Amino-5-(2-diethylamino-ethoxy)-2-propoxy-4-ethoxy-fluoren-9-one
1-Amino-5-(2-diethylamino-ethoxy)-2-propoxy-4-methoxy-fluoren-9-one
1-Amino-5-(2-diethylamino-ethoxy)-2-propoxy-4-n-butoxy-fluoren-9-one
1-Amino-5-(2-pyrrolidinyl-ethoxy)-2-propoxy-4-ethoxy-fluoren-9-one
1-Amino-5-(2-pyridinyl-ethoxy)-2-propoxy-4-ethoxy-fluoren-9-one
1-Amino-5-[2-(morpholino-4-yl)-ethoxy]-2-propoxy-4-ethoxy-fluoren-9-one
1-Amino-5-(2-pyrrolidinyl-ethoxy)-2-propoxy-4-methoxy-fluoren-9-one
1-Amino-5-(2-pyridinyl-ethoxy)-2-propoxy-4-methoxy-fluoren-9-one
1-Amino-5-[2-(morpholino-4-yl)-ethoxy]-2-propoxy-4-methoxy-fluoren-9-one
1-Amino-5-(2-diethylamino-ethoxy)-2,4-dimethoxy-fluoren-9-one
1-Amino-5-(3-diethylamino-propoxy)-2,4-dimethoxy-fluoren-9-one
1-Amino-5-(2-pyrrolidinyl-ethoxy)-2,4-dimethoxy-fluoren-9-one
1-Amino-5-(2-pyridinyl-ethoxy)-2,4-dimethoxy-fluoren-9-one
1-Amino-5-[2-(morpholino-4-yl)-ethoxy]-2,4-diemthoxy-fluoren-9-one
1-Amino-5-(2-diethylamino-ethoxy)-2,4-diethoxy-fluoren-9-one
1-Amino-5-(3-diethylamino-propoxy)-2,4-diethoxy-fluoren-9-one
1-Amino-5-(2-pyrrolidinyl-ethoxy)-2,4-diethoxy-fluoren-9-one
1-Amino-5-(2-pyridinyl-ethoxy)-2,4-diethoxy-fluoren-9-one
1-Amino-5-[2-(morpholino-4-yl)-ethoxy]-2,4-diethoxy-fluoren-9-one
1-Amino-5-(2-diethylamino-ethoxy)-2,4-dipropoxy-fluoren-9-one
1-Amino-5-(3-diethylamino-propoxy)-2,4-dipropoxy-fluoren-9-one
1-Amino-5-(2-pyrrolidinyl-ethoxy)-2,4-dipropoxy-fluoren-9-one
1-Amino-5-(2-pyridinyl-ethoxy)-2,4-dipropoxy-fluoren-9-one
1-Amino-5-[2-(morpholino-4-yl)-ethoxy]-2,4-dipropoxy-fluoren-9-one Examples of Compounds of the Method of use of the Invention Include the Following All compounds enumerated previously, and
2,5-Bis-(2-diethylamino-ethoxy)-fluoren-9-one
2,5-Bis-(2-dimethylamino-ethoxy)-fluoren-9-one
2,5-Bis-(2-dipropylamino-ethoxy)-fluoren-9-one
2,5-Bis-(3-dimethylamino-propoxy)-fluoren-9-one
2,5-Bis-(3-diethylamino-propoxy)-fluoren-9-one
2,5-Bis-(3-dipropylamino-propoxy)-fluoren-9-one The following definitions have been employed throughout the experimental examples Room or ambient temperature=18° C.–25° C.
overnight=8–12 hours
brine=a saturated aqueous solution of sodium chloride (NaCl)

THF = tetrahydrofuran
MgSO$_4$ = magnesium sulfate
CH$_2$Cl$_2$ = methylene chloride
NaOH = sodium hydroxide
LDA = Lithium diisopropylamine
EtOAc = Ethyl acetate
NH$_4$Cl = Ammonium chloride Where literature references are specifically identified, it is intended that they are to be construed as being incorporated by reference.

I. Bis-basic Fluorenones

EXAMPLE 1

The following Example 1A–1D syntheses were adapted from Meyers, A. I. and Mihelitch E. D., *J. Am. Chem. Soc.*, 97, 7383 (1975).

EXAMPLE 1A

2-(2,3-Dimethoxy-phenyl)-4,4-dimethyl-4-oxazoline

At room temperature, add dropwise thionyl chloride (66 mL, 107.6 g, 0.9 mole) to 2,3-dimethoxy benzoic acid (54.63 g., 0.3 mole) and stir overnight until formation of the benzoyl chloride is complete. Remove excess thionyl choride and any gas evolved on a rotary evaporator. Add additional toluene to remove any residual thionyl chloride from the reaction vessel. Dissolve the previously formed 2,3-dimethoxy benzoic acid chloride into methylene chloride (150 mL) and add to it a stirred solution of 2-amino-2-methyl-propanol (53.40 g, 57.2 mL, 0.6 mole) in chloroform (150 mL) at 0° C., while keeping the reaction temperature below 10° C. Once the addition is complete, stir overnight and filter off any remaining amino-alcohol as a white solid. Wash and extract the filtrate twice with 300 mL water. Dry over magnesium sulfate, filter and condense to obtain a yellow oil. Place under a near vacuum until the product solidifies (N-(2-hydroxy-1,1-dimethyl-ethyl)-2,3-dimethoxy-benzamide). Add dropwise additional thionyl chloride (64 mL) noting the resulting exothermic reaction and yellow solution. Stir about 1 hour, then add about 500 mL of anhydrous diethyl ether and stir overnight to precipitate to product oxazoline as the hydrochloride salt. Decant the previously added ether from the reaction and add an additional amount (300 mL) and stir vigorously. Take-up remaining solid in a solution of cold ether:NaOH (aq.) (80:20), while ensuring the aqueous phase is basic. Wash the organic phase with brine and dry with MgSO$_4$. Strip off the remaining ether and dry under near vacuum to obtain the title compound. Yield 43.1 g. (61%), m.p. 48–50° C. (off-white crystals). The compound has the following structure:

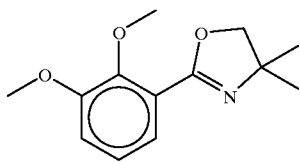

EXAMPLE 1B

2-(6,4'-Dimethoxy-biphenyl-2-yl)-4,4-dimethyl-4-oxazoline

Prepare a solution magnesium (5.5 g, 0.22 moles) in about 45 mL diethyl ether add dropwise 4-bromoanisole (41.1 g, 27.5 mL, 0.22 mole) while stirring. Gently heat and add iodine and/or 1,2-dibromoethane as needed in order to initiate the reaction. Continue addition of 4-bromoanisole at a rate sufficient to maintain reflux. Once addition is complete, add additional ether (100 mL) and heat to reflux for about 1 hour. Cool to room temperature and dropwise add 2-(2,3-dimethoxy-phenyl)-4,4-dimethyl-4-oxazoline (17.6 g, 0.075 mole) dissolved in 90 mL THF, then stir overnight noting the subsequent exotherm and dark brown color of the solution. Quench with 150 mL ammonium chloride. Separate the organic layer and extract the aqueous phase with 100 mL THF. Wash the combined organic phases twice wit-h 200 mL brine. Dry over MgSO$_4$, filter and rotovap to a thick yellow semisolid. Dissolve in 10% HCl (30 mL conc. acid diluted to 120 mL) and wash twice with 100 mL ether. The hydrogen chloride salt of the title compound precipitates in the aqueous layer. Make the aqueous layer and solids basic with 50% NaOH solution. Extract twice with 250 mL ethyl acetate. Dry the organic phases with MgSO$_4$, filter and rotovap to obtain 24.2 g (0.08 moles) of the title compound.

$^1$H-NMR (CDCl$_3$) δ1.43 (s, 6H), 3.89 (s, 3H), 3.86 (s, 3H), 4.66 (s, 2H), 7.05 (d, 2H), 7.22 (d, 2H), 7.48 (dd, 2H), 7.60 (dd, 1H).

This compound has the following structure:

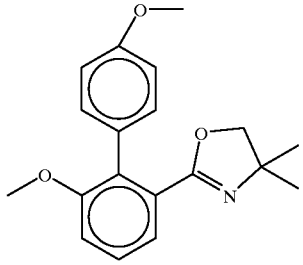

EXAMPLE 1C

2,5-dimethoxy-fluoren-9-one

Combine 2-(6,4'-Dimethoxy-biphenyl-2-yl)-4,4-dimethyl-4-oxazoline (24.2 g, 0.08 mole) and 4.5 N hydrochloric acid (750 mL) and heat while stirring at reflux overnight. Cool to room temperature while stirring. Filter the resulting solidified brown oil through sintered glass and wash three times with 100 mL water and allow to air dry. Transfer into a pestel and grind into a tan powder to obtain 6,4'-dimethoxy-biphenyl-2-carboxylic acid. (16.4 g., 77%).

Prepare a suspension of 6,4'-Dimethoxy-biphenyl-2-carboxylic acid (15.5 g, 0.060 mole) in 300 mL of anhydrous methylene chloride under argon at room temperature. Add dropwise thionyl chloride (6.5 g, 0.078 moles, 4.0 mL) and heat at reflux for about 1 hour, ensuring the conversion to the acid chloride. Cool to 0° C. and add dropwise tin chloride (SnCl$_4$), 20.6 g, 0.079 mole, 9.1 mL ensuring that the temperature remains between 0°–5° C. Once addition is complete, continue stirring for 2 hours at 0° C. Pour the dark reaction mix over ice, observing the change to orange. Separate the organics and extract the aqueous phase twice with 200 mL methylene chloride. Dissolve any solids with additional methylene chloride if necessary. Wash the combined extracts twice with 200 mL NaHCO$_3$. Wash again with brine. Dry over MgSO$_4$, filter and condense in a rotary evaporator. Filter via short path chromatography and elute with methylene chloride to remove the baseline material. Yield 9.0 g, 62%.

Recrystallize from ethyl acetate to obtain a reddish-orange solid which is 2,5-dimethoxy-fluoren-9-one. m.p. 125°–127° C.

EXAMPLE 1D

2,5-dihydroxy-fluoren-9-one

Prepare a solution of 2,5-dimethoxy-fluoren-9-one (7.5 g, 0.031 mmole) in 50 mL glacial acetic acid and warm to 80° C. Once all of the fluorenone goes into solution, add 150 mL hydrogen bromide (48% solution). Continue heating to reflux, redissolving any precipitate formed, and reflux overnight. Cool to room temperature and filter. Wash the filtrate with water. Take-up the solids in ethyl acetate and dissolve by heating in a steam bath. Filter through a short column of silica, eluting with hot ethyl acetate. Condense the ethyl acetate eluent on a rotary evaporatory to obtain a dark red solid. Heat in hot methylene chloride to dissolve undesired solid and filter to obtain 2,5-dihydroxy-fluoren-9-one. m.p. 298–301 dec. (Yield 9.4 g, 97%).

EXAMPLE 2

2,5-Bis[(2-diethylamino)ethoxy]-fluoren-9-one

EXAMPLE 2A

N,N-Diethyl-2-bromo-5-methoxybenzamide

To a stirred suspension of 2-bromo-5-methoxy benzoic acid (2.31 g, 0.010 mol) and PyBOP (5.20 g, 0.010 mol) in $CH_2Cl_2$ (30 mL) add diethylamine (0.951 g, 0.013 mol) at ambient temperature. Warm the solution slightly and observe a brown color change. To the brown solution add diisopropylethylamine (3.83 mL, 0.022 mol) and stir the resulting mixture at ambient temperature overnight. Extract the reaction mixture with $H_2O$ (100 mL), 5% HCl (2×100 mL), $NaHCO_3$ (2×100 mL), wash with brine (100 mL), dry ($MgSO_4$), filter and evaporate the filtrate to give a brown oil. Chromatography of the oil eluting with EtOAc-hexane 4:6 gives 2.45 g (90%) of the title compound as a pale yellow liquid, Rf=0.24 EtOAc-hexane 4:6; 1 H NMR ($CDCl_3$) 7.40 (1 H, d), 6.79 (1H, s), 6.77 (1H, d), 3.78 (4H, m), 3.41–3.28 (1H, m), 3.18–3.15 (2H, m), 1.27 (3H, s), 1.08 (3H, s).

EXAMPLE 2B

N,N-Diethyl-6,4-dimethoxy-biphenyl-2-carboxamide

To a stirred solution of 2-bromo-5-methoxy-diethylbenzamide (2.43 g, 8.2 mmol) in DME (50 mL), add $Pd(PPh_3)_4$ (0.55 g, 0.5 mmol), 2-methoxy phenylboronic acid (1.52 g, 10 mmol) and $Na_2CO_3$ (2M, 7.0 mL) respectively at ambient temperature. Heat the resulting mixture and stir at reflux under an argon atmosphere for 7 h, then overnight at ambient temperature. Evaporate the solvent and partition the residue between $H_2O$-EtOAc. Wash the organic layer with brine, dry (MgSO4) and chromatograph with EtOAc-hexane to give the title compound as an off white solid. Recrystallization (cyclohexane) yields white plates 1.91 g (69%) mp 117–118° C. Anal. Calcd. for: $C_{19}H_{23}NO_3$: C, 72.82; H, 7.40; N, 4.47. Found: C, 72.57; H, 7.34; N, 4.41.

EXAMPLE 2C 2,5-Dimethoxy-fluoren-9-one

To a stirred solution of freshly distilled diisopropylamine (1.90 mL, 13.5 mmol) in anhydrous THF (20 mL ) at −50° C. add n-BuLi (2.5 M, 5.5 mL, 13.5 mmol). Allow the solution to warm to 0° C. then immediately cool to −20° C. and add N,N-diethyl-6,4'-dimethoxy-biphenyl-2-diethylcarboxamide (1.70 g, 5.4 mmol) in THF (20 mL) dropwise. Allow the resulting solution to stir overnight. Quench the red reaction mixture with a saturated solution of $NH_4Cl$, separate and wash the organic layer with brine, dry (MgSO4), filter and evaporate the filtrate. Recrystallization ($CH_3OH$) of the residual solid provides the title compound as red needles mp 125–127° C.

EXAMPLE 2D 2,5-Dihydroxy-fluoren-9-one

Prepare a solution of 2,5-dimethoxy-fluoren-9-one (0.031 mmol) in glacial acetic acid (50 mL) and warm to 80° C. Add hydrogen bromide (150 mL, 48% solution) and prepare according to the procedure set forth in Example 1D to obtain 2,5-dihydroxy-fluoren-9-one.

EXAMPLE 2E 2,5-Bis[(2-diethylamino)ethoxy]-fluoren-9-one

In a procedure similar to that reported by Andrews, Fleming et al., *J. Med. Chem.* 17(8), 882 (1974): A solution of $NaOCH_3$ is prepared by reacting 0.138 g of Na with 5.0 mL of dry $CH_3OH$. To this solution is added 2,5-dimethoxy-fluoren-9-one (dried at 100° C. overnight under high vacuum) dissolved in chlorobenzene (20.0 mL). Heat the stirred reaction mixture under an argon atmosphere until the methanol is evaporated (130° C.). Prepare the free base of 2-chloroethyldiethyamine by basifying 1.8 g (10.4 mmole) of 2-chloroethydiethylamine hydrochloride with aq. NaOH, extracting with chlorobenzene (20.0 mL), drying with MgSO4, and decanting. Heat the resulting dark brown reaction mixture and stir overnight at reflux. Allow the reaction mixture to cool to ambient temperature, pour into 1% NaOH (100 mL) and extract with $CH_2Cl_2$ (100 mL). Dry (MgSO4) the organic layer, filter and evaporate the filtrate on a rotovap. Dissolve the resulting dark brown oil in dry $Et_2O$ (50 mL) and filter. Wash the filter with additional dry $Et_2O$ (100 mL). To this solution add ethereal HCl under an argon blanket. Recrystallize the precipitated hydrochloride salt ($CH_3OH$/EtOAc) to give the title compound as an orange solid, 0.94 g (75%) mp 235–237° C.

The compound has the following structure:

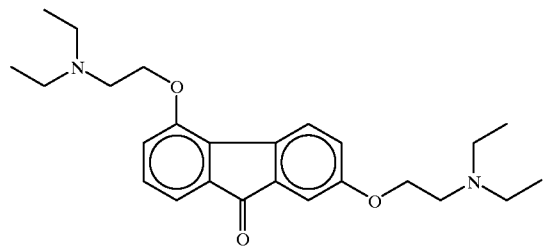

EXAMPLE 3

3,5-Bis-(2-diethylamino-ethoxy)-fluoren-9-one

EXAMPLE 3A 2-(2,3'-dimethoxy-biphenyl-2-yl)-4,4-dimethyl-4-oxazoline

In a manner analogous to Example 1B, prepare a grignard reagent of magnesium (2.7 g, 0.11 moles) in 20 mL anhydrous diethyl ether adding dropwise 3-bromoanisole (20.6 g, 0.11 moles) to obtain 2-(2,3'-dimethoxy-biphenyl-2-yl)-4,4-dimethyl- 4-oxazoline. Yield: 12.5 g (100%). EtOAc-hexane 4:6, $R_f$=0.26

$^1$H-NMR (CDCl3) δ1.20 (6H, s, $CH_3$), 3.70 (2H, s, $CH_2$), 3.77 (3H, s, $OCH_3$), 3.80 (3H, s, $OCH_3$), 6.84–6.93 (2H, m, Ar—H), 6.94 (1H, d, Ar—H), 7.05 (1H, d, Ar—H), 7.26–7.38 (3H, m, Ar—H).

The structure of the compound is the following:

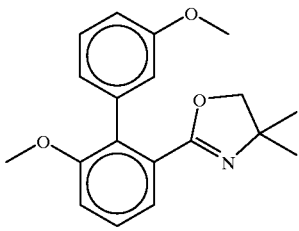

EXAMPLE 3B 3,5-Dimethoxy-fluoren-9-one, 1,5-dimethoxy-fluoren-9-one

In a manner analogous to Example 1C, combine 2-(6,3'-dimethoxy-biphenyl-2-yl)-4,4-dimethyl-4-oxazoline (11 g, 0.035 mole) and 4.5 N hydrochloric acid (117 mL diluted to about 350 mL) to obtain 8.2 g, 91%) of the carboxylic acid (6,3'-dimethoxy-biphenyl-2-carboxylic acid).

In a manner analogous to Example 1C, react 6,3'-dimethoxy-biphenyl-2-carboxylic acid (8.2 g, 0.032 moles) and thionyl chloride (3.3 g, 0.04 moles, 2.1 mL), then react tin chloride (11.2 g, 0.043 mole,). After 3 days, quench the reaction with aqueous HCl . The organic layer is separated and dried over $MgSO_4$, filtered and the solvents evaporated. Fractional crystallization from EtOAc/hexane gives the 3,5-isomer (m.p. 122°–124° C.) as well as the 1,5 isomer (m.p. 118°–121° C.) of dimethoxy-fluoren-9-one.

Yields: (3,5 isomer): 4.24 g, 55%; (1,5 isomer): 0.73 g, 9.5%.

$^1$H-NMR (CDCl$_3$)(3,5-isomer) δ3.74 (3H, s, OCH3), 3.79 (3H, S, OCH3), 6.80–6.89 (3H, m, Ar—H), 7.12 (1H, d, Ar—H), 7.27 (1H, d, Ar—H), 7.37 (1H, 7.48 (1H, d, Ar—H).

The structure of the compounds is the following:

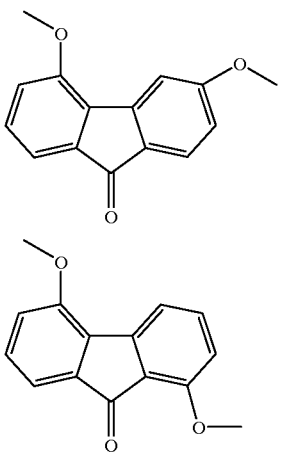

3,5-isomer (major product) 1,5-isomer (minor product)

EXAMPLE 3C1

3,5-dihydroxy-fluoren-9-one

In a manner analogous to Example 1D, prepare a solution of 3,5-dimethoxy-fluoren-9-one (4.0 g, 16.6 mmole) in 25 mL glacial acetic acid and react with 75 mL hydrogen bromide to obtain the title compound. (m.p. 301–3030° C. (dec.) (54%)

EXAMPLE 3C2

1,5-dihydroxy-fluoren-9-one

In a manner analogous to Example 1D, prepare a solution of 1,5-dimethoxy-fluoren-9-one (0.65 g, 2.7 mmole) in 15 mL glacial acetic acid and react with 15 mL hydrogen bromide to obtain the title compound (m.p. 2361°–238° C. (dec.), yield 0.50 g, 2.3 mmole, 87%).

EXAMPLE 3D1

3,5-Bis[(2-diethylamino)ethoxy]-fluoren-9-one

Prepare a solution of 3,5-dihydroxy-fluoren-9-one (1.06 g, 5 mmole) in 8 mL methanol and sodium methoxide (0.59 g, 11 mmole) in 24 mL chlorobenzene. Heat while stirring to evaporate the methanol. Separately prepare the free base of 2-chloroethyldiethyl amine hydrochloride by making 15 mL of an aqueous solution of the amine chloride (2.1 g, 12 mmole) basic with aqueous NaOH, then adding sodium chloride until the solution becomes saturated and the amine precipitates. Extract twice with 20 mL of chlorobenzene, then dry over $MgSO_4$ and filter.

When the temperature of the methanolic fluorenone solution reaches 130° C., cool to 100° C., add the previously prepared free base of 2-chloroethyl-diethyl amine and continue stirring overnight. Pour the mixture into 200 mL of 1% sodium hydroxide and twice extract with 100 mL $CH_2Cl_2$. Dry with $MgSO_4$, filter through celite and remove the solvent. Remove residual solvent by placing under vacuum. Take-up the remaining orange oil in ether and filter through celite. Add ethereal hydrogen chloride until a precipitate forms. Wash with diethyl ether and dry the orange-yellow solid at 80° C. under near vacuum for 24 hours to obtain the title compound. m.p. 198–201° C. (dec.). Yield 1.27 g, 52%).

Analysis calculated for $C_{25}H_{34}N_2O_3 \cdot 2HCl \cdot 3H_2O$: C, 62.10; H, 7.51; N, 5.79; Found: C, 61.06; H: 7.79; N: 5.63. The structure of the compound is the following:

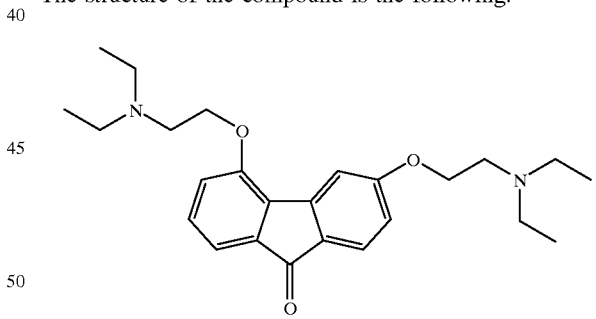

EXAMPLE 3D2

1,5-Bis[(diethylamino)ethoxy]-fluoren-9-one

In a manner analogous to Example 3D1, prepare a solution of 1,5-dihydroxy-fluoren-9-one (0.5 g, 2.3 mmole) in 4 mL of methanol and 12 mL chlorobenzene, then add the sodium methoxide (0.28 g, 5.1 mmole). The free base 2-chloro-ethyl-diethyl amine is added (1.1 g, 6 mmole) in 20 mL chlorobenzene. Work-up the reaction in the usual manner to obtain the title compound. m.p. 180–184° C. (dec.). Yield 0.68 g, 61%.

Analysis calculated for $C_{25}H_{34}N_2Cl_3 \cdot 2HCl \cdot 3H_2O$: C, 62.10; H, 7.51; N, 5.59. Found: C, 61.86; H, 7.53; N, 5.68

The structure of the compound is the following:

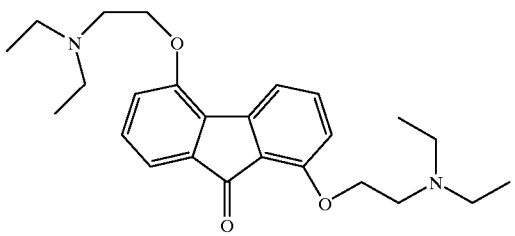

EXAMPLE 4

2,5-bis-(2-diethylamino-ethoxy)-4-methoxy-fluoren-9-one

EXAMPLE 4A 2,5-bis-(2-diethylamino-ethoxy)-4-methoxy-fluoren-9-one 2,5-Dihydroxy-4-methoxy-fluoren-9-one (0.22 g, 0.9 mmole), 2-chloroethylamine hydrochloride (1.7 g, 0.10 mole) and sodium methoxide (0.20 g, 3.6 mmoles) are reacted as described in Example 9b to give the title compound as the hemihydrate. (0.10 g, 22%). m.p. 236–238° C. Analysis calculated for $C_{26}H_{36}N_3O_4 \cdot 2HCl \cdot 1/5 \cdot H_2O$: C, 60.39; H, 7.49; H, 5.42. Found: C, 60.24; H, 7.36; N, 5.39.

The structure is:

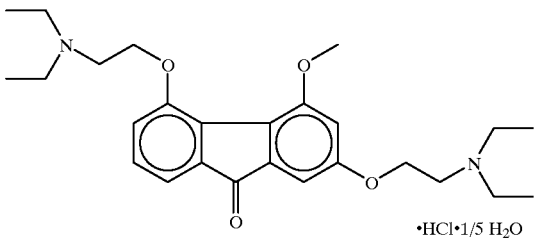

·HCl·1/5 $H_2O$

The following syntheses were adapted from M. V. Sargent, *J Chem. Soc. Perkin Trans.* I, 2553 (1987) and W. Wang, V. Snieckus, *J. Org. Chem.*, 57, 424 (1992).

EXAMPLE 4B 2,5-dihydroxy-4-methoxy-fluoren-9-one (Dengibsin)

6,4'-Diisopropyloxy-2'-methoxy-biphenyl-2-diethylcarboxamide (1.30 g, 3.3 mmole) in THF (15.0 mL) is added dropwise to a stirred solution of LDA (0.013 mole) in THF (30 mL) under argon at −50° C. Warm the resulting pale yellow solution to ambient temperature and stir for 48 hours. Quench with a saturated solution of $NH_4Cl$ (30 mL) and dilute with THF (150 mL). Separate and wash the organic layer, then wash with brine, separate, dry over $MgSO_4$ and filter. Concentrate the filtrate to give a red oil (1.07 g). Flash chromatography eluting with EtOAc/hexane 15:85 gave 0.57 g of the title compound as a red solid. m.p. 71–72° C.

EXAMPLE 4C 6,4'-diisopropyloxy-2'-methoxy-biphenyl-2-diethyl-carboxamide

Thionyl chloride (0.1793 g, 2.1 mmole) is added dropwise to a stirred solution of 6,4'-diisopropyloxy-2'-methoxy-biphenyl-2-carboxylic acid (0.315 g, 0.9 mmole) and 1,2,4-trimethoxybenzene (0.1576 g, 0.9 mmole) in $CH_2Cl_2$ (14.00 mL) under an argon atmosphere. Stir the resulting yellow solution for 15 minutes at ambient temperature then heat at 41° C. for 15 minutes. Cool the resulting light brown solution to 0°–5° C. in an ice bath and add diethylamine (0.848 g, 11.6 mmole) dropwise, ensuring the temperature remains below 15° C. Following completion of the addition, warm the solution to ambient temperature and stir for 4 hours. Dilute with $CH_2Cl_2$ (75 mL), then extract with water (2×50 mL), separate, extract with 5% $NaHCO_3$ (2×50 mL), separate, wash with brine (50 mL), separate and dry over $MgSO_4$. Filter concentrate and chromatograph (EtOAc/hexane 4:6) the resulting residue to obtain the title compound as a white solid. m.p. 74–75° C.

EXAMPLE 4D 6,4'-diisopropyloxy-2'-methoxy-biphenyl-2-carboxylic acid

Prepare a solution of 2-(6,4'-diisopropyloxy-2'-methoxy-biphenyl-2-yl)-3,4,4-trimethyl-oxazolinium iodide (13.20 g, 0.0245 mole) in 20% NaOH (140 mL) and methanol (140 mL) and stir at reflux overnight. Concentrate the resulting colorless solution on the rotovap until precipitation begins. Dilute the resulting suspension to 300 mL with water and acidify with concentrated HCl to pH=1. Extract the precipitate into $CH_2Cl_2$ (400 mL), wash with brine, separate and dry over $MgSO_4$. Filter, concentrate and recrystallize from cyclohexane (~175 mL) to obtain the title compound (7.10 g, 84%). m.p. 117–119° C.

EXAMPLE 4E 2-(6,4'-diisopropyloxy-2'-methoxy-biphenyl-2-yl)-3,4,4-trimethyl-oxazolinium iodide Add iodomethane (12.43 g, 0.0875 mole) to a stirred solution of 2-(6,4'-diisopropyloxy-2'-methoxy-biphenyl-2-yl)-4,4-dimethyloxazoline (5.80 g, 0.0146 mole) in dry DMSO (30 mL). Stir the resulting mixture for about 72 hours, then dilute with ether (600 mL). Collect the precipitated solid by filtration, then triturate with $CHCl_3$ (400 mL) and filter. Discard the insoluble solid and concentrate the filtrate to obtain the title compound as an off-white solid. m.p. 213°–214° C.

EXAMPLE 4F 2-(6,4'-diisopropyloxy-2'-methoxy-biphenyl-2-yl)-4,4-dimethyloxazoline 2-(2,3-Diisopropyloxy-phenyl-2-yl)-4,4-dimethyl-oxazoline (8.74 g, 0.030 mole) in THF (30 mL) is added dropwise at ambient temperature to the Grignard reagent prepared from 1-bromo-2-methoxy-4-isopropoxy-benzene (7.35 g, 0.030 mole) and magnesium (0.7240 g, 0.030 mole) in dry THF (175 mL). Following the completion of the addition, stir overnight at ambient temperature. Quench the reaction with a saturated solution of $NH_4Cl$, separate, wash with brine, separate, dry over $MgSO_4$, filter and concentrate on the rotary evaporator. Chromatograph the residue (EtOAc-hexane; 4:6) to give 6.52 g (64%) as a viscous liquid. $R_f$=0.29. The structure corresponds to the following:

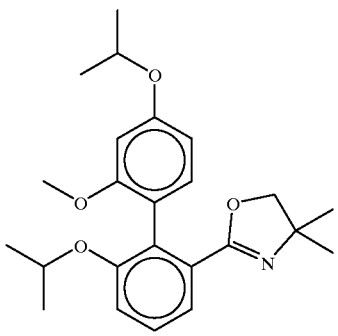

EXAMPLE 4G

3-methoxy-4-bromophenol

4-Bromo-resorcinol (17.75 g, 0.0896 mole) and potassium carbonate ($K_2CO_3$, 80.0 g, 0.58 mole) are stirred in acetone (1 L) under argon. Add para-toluenesulfonyl chloride (17.12 g, 0.0896 mole) and heat to reflux for about 20 hours. Cool the mixture to room temperature, add methyl iodide ($CH_3I$, 34.20 g, 15.00 mL, 0.24 mole). Cool to ambient temperature then dilute with ether (800 mL) and filter through celite. Concentrate to give 31.70 g of a semisolid, transfer to a 3 L flask with ethanol (1 L), and add 8% aqueous potassium hydroxide (1 L), then heat and stir at reflux until all the solids go into solution. Continue heating under argon for 2 hours and stir overnight under argon at ambient temperature. Acidify the reaction mixture with HOAc (100 mL) in an ice bath, then extract with ether (3×400 mL). Wash the ether extracts with brine, separate, dry over $MgSO_4$ and filter. Concentrate the resulting yellow liquid under vacuum overnight to give 18.0 g (99%) of a waxy solid of the title compound.

II. Mono-basic, alkoxy fluorenones

EXAMPLE 5

5-(2-Diethylamino-ethoxy)-2-methoxy-fluoren-9-one

EXAMPLE 5A

5-(2-Diethylamino-ethoxy)-2-methoxy-fluoren-9-one

In a manner analogous to Example 3D1, combine 5-hydroxy-2-methoxy-fluoren-9-one (0.35 g, 1.5 mmole), 3 mL methanol and sodium methoxide (0.12 g, 2.1 mole) in 10 mL chlorobenzene. After cooling, add the specially prepared free base 2-chloroethyldiethyl amine to obtain the hydrochloride salt of the title compound as a yellow-orange powder. m.p. 196°–199° C. (dec.). Yield 0.387 g, 72%.

Anal. Calc'd for $C_{20}H_{23}NO_3 \cdot HCl$: C, 66.38; H, 6.69; N, 3.87. Found: C, 66.16; H, 6.69; N, 3.80.

EXAMPLE 5B

5-hydroxy-2-methoxy-fluoren-9-one

Combine 5-isopropoxy-2-methoxy-fluoren-9-one (0.78 g, 2.9 mmole) with boron trichloride (6.50 mL of 1.0 M in methylene chloride) in 20 mL methylene chloride at a temperature between 0° and −50° C. Stir the reaction for 1 hour at 5° C., then quench with 20 mL of water, ensuring the temperature is kept below 20° C. The solution changes from a dark brown solution to red as a flocculent solid precipitates. m.p 245°–248° C. Filter the precipitate to obtain 0.296 g of a red solid. m.p 245°–248° C.

Analysis calculated for $C_{14}H_2O_3$, C: 74.33, H: 4.46; Found; C: 74.33; H: 4.58.

EXAMPLE 5C

5-isopropoxy-2-methoxy-fluoren-9-one

Combine n-butyl lithium (22.00 mL of 2.5 M, 0.055 mole) and diisopropylamine (6.07 g, 0.060 mole), while stirring, in 150 mL tetrahydrofuran (THF) at −50° C. Wait approximately 5 minutes, then dropwise add N,N-diethyl-2'-isopropoxy-4-methoxy-biphenyl-2-carboxamide (3.80 g, 0.011 mole) dissolved in 50 mL THF. Remove the cooling source and allow the reaction to obtain ambient temperature, then stir while heating at 65° C. for 5 hours. The reaction changes color to orange, then to dark brown. Continue stirring the reaction overnight at ambient temperature overnight, then cool in an ice bath and neutralize with about 100 mL of a saturated solution of ammonium chloride. The reaction changes color to orange. Wash the THF solvent separately with brine (saturated sodium chloride) and dry over magnesium sulfate. Filter and concentrate to give a red liquid. Chromatography purification of this; material (20% ethyl acetate: 80% hexane) results in an orange liquid which solidifies when dried under high vacuum to give an orange solid (1.60 g, 50%). m.p. 89°–90° C.

Anal. calc'd for: $C_{17}H_{16}O_3$: C, 76.10; H, 6.06. Found: C, 76.31; H, 6.0.

EXAMPLE 5D

N,N-diethyl-2'-isopropoxy-4-methoxy-biphenyl-2-carboxamide

Prepare a solution of 2'-isopropoxy-4-methoxy-biphenyl-2-carboxylic acid (4.80 g, 0.0168 mole) in 125 mL methylene chloride (dichloromethane). Under an argon atmosphere, at ambient conditions, add thionyl chloride (2.99 g, 0.0356 mole, 1.835 mL). Continue stirring for about 45 minutes, observing the color change to light brown. Cool the reaction mixture to 0° C. and dropwise add diethylamine (22.00 mL, 15.627 g, 0.21 mole), ensuring the temperature does not exceed 25° C. Continue stirring for 30 minutes after addition of the amine is complete. Dilute the reaction to 150 mL of methylene chloride and wash the organic phase with water, separate and wash twice with 100 mL 5% sodium bicarbonate. Separate and wash with brine (sat'd NaCl) and dry over magnesium sulfate. Filter through celite and evaporate on a rotary evaporator to give a viscous light brown liquid. Chromatography (30% ethyl acetate: 70% hexane) gives a pale yellow liquid. Place under near vacuum to give a waxy solid of the title compound (3.80 g, 66%).

EXAMPLE 5E

2'-Isopropoxy-4-methoxy-biphenyl-2-carboxylic acid

Prepare a solution of sodium hydroxide (20%, 60 mL) and methanol (60 mL) and add 2-(2'-isopropoxy-4-methoxy-biphenyl-2-yl)-3,4,4-trimethyl-4-oxazolinium iodide salt (8.30 g, 0.0172 mole). Stir the reaction mixture and heat at reflux temperature for about 20 hours under an argon atmosphere. Allow the reaction to cool to ambient temperature and reduce the reaction volume on a rotary evaporator to to the point where the reaction just becomes turbid. Dilute the reaction mixture with water to 500 mL, then acidify with concentrated hydrochloric acid. A gummy precipitate forms. Extract into methylene chloride (150 mL), and wash the organic phase twice with 100 mL sodium bicarbonate. Separate and wash with brine and dry over magnesium sulfate. Filter through celite to give an off-white solid (4.85 g, 98%).

The compound has the following structure:

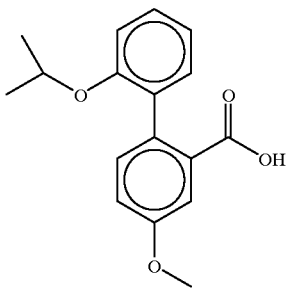

EXAMPLE 5F 2-(2'-isopropoxy-4-methoxy-biphenyl-2-yl)-3,4,4-trimethyl-4-oxazolinium iodide Add iodomethane (22.8 g, 10.00 mL) to a stirred solution of 2-(2'-isopropoxy-4-methoxy-biphenyl-2-yl)-4,4-dimethyl-4-oxazoline (7.40 g, 0.0218 mL) in nitromethane (60 mL) and stir the resulting mixture overnight under argon. Dilute the solution with dry ether (400 mL) and collect the resulting white precipitate by filtration and air dry to give a white solid (8.30 g, 79%).

The structure of the compound is:

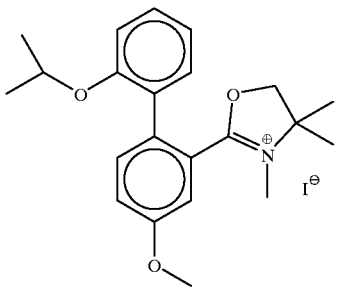

EXAMPLE 5G 2-(2'-isopropoxy-4-methoxy-biphenyl-2-yl)-4,4-dimethyl-4-oxazoline Prepare a Grignard solution of 1-bromo-2-isopropoxy benzene (16.13 g, 0.075 mL) and magnesium (1.82 g, 0.075 mole) in anhydrous THF (150 mL). Carefully add a solution of 2-(2,5-dimethoxyphenyl)-4,4-dimethoxy-4-oxazoline (7.07 g, 0.030 mole) dissolved in THF (30 mL). Allow the reaction temperature to increase to 32° C. during the addition. After the addition is complete, stir the reaction overnight at ambient temperature. Neutralize with NH$_4$Cl (75 mL). Separate the THF layer, wash with brine, separate again, concentrate, dissolve in 5% HCl (300 mL) then make basic to pH 8.0 with solid potassium carbonate (K$_2$CO$_3$), collecting the resulting precipitate and extracting into EtOAc.

Separate the EtOAc mixture, wash with brine, separate, dry over MgSO$_4$, filter and then concentrate the filtrate to a crude yellow oil. Chromatograph the oil by eluting with 20% EtOAc/80% hexane to give 7.40 g (63%) of the title compound.

The structure of the compound is:

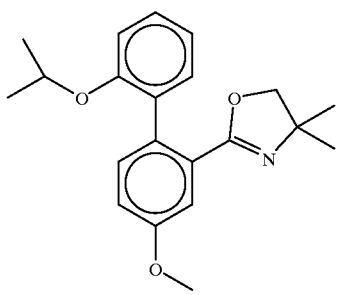

EXAMPLE 5H 2-(2,5-dimethoxy-phenyl)-4,4-dimethyl-4-oxazoline

At ambient temperature and under an argon atmosphere, add thionyl chloride (97.97 g, 60.00 mL, 0.823 mole) dropwise to 2,5-dimethoxybenzoic acid (50.00 g, 0.2745 mol) and stir overnight. Evaporate the excess thionyl chloride on a rotovap, then add toluene (~50 mL) and concentrate on the rotovap. Dissolve the resulting acid chloride in methylene chloride (about 180 mL) and, at 0° C., add to a stirred solution of 2-amino-2-methyl-1-propanol (26.74 g, 28.63 mL, 0.30 mole) in methylene chloride (270 mL), taking care to ensure the temperature does not rise above 20° C. After precipitation, stir for 2 hours at ambient. temperature. Extract twice in 200 mL water, wash with brine, dry over magnesium sulfate, filter and concentrate to give the amide (N-(1-hydroxy-1-methyl-ethyl)-2,5-dimethoxy-benzamide).

Powder the amide and place into a flask with a magnetic stirring bar. While stirring, slowly add additional thionyl chloride (54.00 mL, 88.07 g, 0.7403 mole), observing the resulting exotherm. Continue stirring the solution after addition is complete for about 20 minutes, then dilute with dry ether and stir overnight. Collect the precipitate, wash with anhydrous ethyl acetate and air dry. Dissolve the resulting gummy solid in H$_2$O and neutralize with 20% NaOH. Extract the resulting oil into EtOAc (500 mL). Wash the ethyl acetate layer with brine and dry over MgSO$_4$. Filter and concentrate to give the title compound (50.40 g, 77%).

The compound has the following structure:

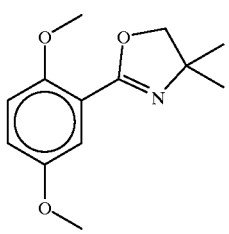

EXAMPLE 6

5-(2-Diethylamino-ethoxy)-2-propoxy-fluoren-9-one

EXAMPLE 6A 5-(2-Diethylamino-ethoxy)-2-propoxy-fluoren-9-one

Dissolve 2-chloroethyldiethylamine hydrochloride (0.60 g, 3.5 mmole) into water (20 mL) and make basic with aqueous NaOH. Extract with chlorobenzene (2×10 mL), and dry the organic layer over MgSO$_4$ and filter. Dissolve 5-hydroxy-2-propoxy-9-fluoren-9-one (0.42 g, 1.6 mmol) into a solution of methanol (2.0 mL) and chlorobenzene (10 mL). To the MeOH/chlorobenzene mixture, add sodium methoxide (0.10 g, 1.8 mmole) and heat the resulting mixture to 130° C. Cool the dark-brown suspension to 100° C. and add dropwise the 2-chloroethyldiethylamine solution. Heat the combined mixtures at reflux overnight. Work-up the reaction as described in Example 2E to give the title compound as the hydrate. (0.28 g, 44%). m.p. 190°–193° C. CI-MS [M+H]$^+$=354. Analysis calculated for: C$_{22}$H$_{27}$NO$_3$.HCl.(2.5)H$_2$O: C, 66.99; H, 7.28; N, 3.55. Found: C, 66.73; H, 7.47; N, 3.56

$^1$H-(CDCl$_3$) δ0.97 (3H, t, CH$_3$), 1.26 (6H, t, CH$_3$), 1.73 (2H, m, CH$_2$), 3.27 (4H, q, CH$_2$), 3.65 (2H, NCH$_2$), 4.00 (2H, t, OCH$_2$), 4.58 (2H, t, OCH$_2$), 7.09 (1H, d, ArH), 7.14 (1H, s, ArH), 7.23 (1H, d, ArH), 7.30 (1H, t, ArH), 7.36 (1H, d, ArH), 7.75 (1H, d, ArH).

The structure of the compound is:

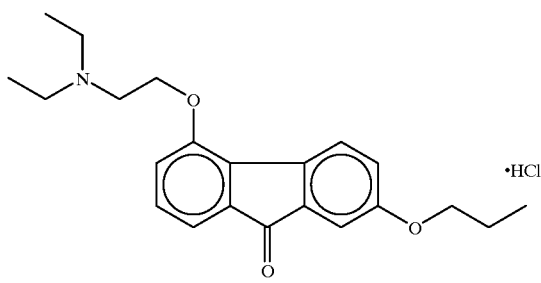

EXAMPLE 6B 5-hydroxy-2-propoxy-fluoren-9-one

Add n-butyl-lithium (4.80 mL, 0.012 mole) in THF (60 mL) dropwise to diphenylphosphine (Ph$_2$PH, 2.34 g, 0.012 mole) at −20° C. Warm to resulting red solution to abient temperature, then stir for 30 minutes. Prepare a solution of 5-methoxy-2-propoxy-fluoren-9-one (0.88 g, 3.3 mmole) in THF (20 mL) and add to the stirred dark-red Ph$_2$PH solution, stirring for an additional hour while the color changes from dark-red to brown, then heating at reflux for 15 minutes. Cool to abient temperature, then quench with a saturated solution of NH$_4$Cl. Separate the THF layer, wash with brine, dry over MgSO$_4$, filter and concentrate the filtrate to an orange oil. Dissolve the oil in CH$_2$Cl$_2$ and extract with 5% aq. NaOH (50 mL) as a purple solid formed in the aqueous layer.

Separate the aqueous layer in a separatory funnel and collect the precipitated solid by filtration. Acidify the solid in aqueous phase to pH 1 with HCl and dissolve into EtOAc (150 mL). Dry the EtOAc solvent over MgSO$_4$, filter and evaporate to give 0.450 g (44%) of the title phenol. m.p. 224–226.

The structure of the compound is:

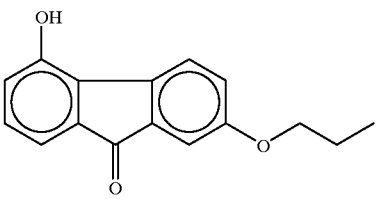

EXAMPLE 6C 5-methoxy-2-propoxy-fluoren-9-one

In a manner similar to Example 1C, second paragraph, react 6-methoxy-4'-propoxy-biphenyl-2-carboxylic acid (2.85 g, 0.0106 mole) in anhydrous methylene chloride (~50 mL) with thionyl chloride (2.10 g, 1.10 mL) and tin chloride (5.21 g, 2.30 mL, 0.030 mole) to form 5-methoxy-2-propoxy-fluoren-9-one. Yield 2.24 g, 83% m.p. 96–97° C.

$^1$H-NMR (CDCl$_3$) δ1.04 (t, 3H, CH$_3$), 1.81 (q, 2H, CH2), 3.94 (m, 5H, OCH, OCH$_3$), 6.91 (d, 1H), 7.21–7.15 (m, 2H), 7.25 (d, 1H), 7.65 (d, 1H).

EXAMPLE 6D 6-methoxy-4'-propoxy-biphenyl-2-yl)-2-carboxylic acid

In a manner similar to Example 5E, react 2-(6-methoxy-4'-propoxy-biphenyl)-3,4,4-trimethyl-4-oxazolinium iodide (5.10 g, 0.0106 mole) in 50 mL 20% sodium hydroxide and 50 mL methanol to give the title compound (2.80 g, 98%). m.p. 118–120° C.

EXAMPLE 6E 2-(6-methoxy-4'-propoxy-biphenyl)-3,4,4-trimethyl-4-oxazolinium iodide In a manner similar to Example 5F, react 2-(6-methoxy-4'-propoxy-biphenyl)-4,4-dimethyl-4-oxazoline (65.10 g, 0.018 mole), methyl iodide (5.00 mL) and nitromethane to give the title compound (7.10 g, 82%). m.p. 222–224° C.

EXAMPLE 6F 2-(6-methoxy-4'-propoxy-biphenyl)-4,4-dimethyl-4-oxazoline

In a manner similar to Example 1A, react 4-bromo-1-n-propoxybenzene (10.75 g, 0.050 mole) and magnesium (1.22 g, 0.050 mole) in diethyl ether (100 mL) along with 1,2-dibromo-ethane (3 drops) and iodine (crystals) as needed in order to initiate the reaction. Add additional diethyl ether (~50 mL), then heat to reflux for about 1 hour. Cool to ambient temperature, and dropwise add 2-(2,3-dimethoxy-phenyl)-4,4-dimethyl-4-oxazoline (4.70 g, 0.020 mole) dissolved in tetrahydrofuran (60 mL). The reaction temperature increases to around 36° C. during the addition. Continue stirring the light brown reaction mixture overnight, then quench with a saturated solution of ammonium chloride. Separate and wash the organic layer with brine, separate again, dry over MgSO$_4$, filter and concentrate. Dissolve the residual oil in ethyl acetate and extract into about 200 mL of 9% hydrochloric, acid. Separate the aqueous layer, then make alkaline with solid potassium carbonate. Extract into EtOAc, separate and dry over MgSO$_4$ and concentrate to give the title compound (4.70 g, 70%).

EXAMPLE 6G 1-bromo-4-propoxy-benzene

Prepare a solution of 4-bromo-phenol (17.30 g, 0.10 mol) and potassium carbonate (13.80 g, 0.1 mole) in isopropanol (175 mL). Heat the resulting mixture at reflux and stir overnight. Cool to ambient temperature, filter and condense the filtrate on a rotary evaporator. Dissolve the residual oil in ethyl acetate (250 mL) and extract twice with 5% sodium hydroxide (100 mL), separate and wash with brine. Kugelrohr distillation at 100°–120°, 0.05 mm, gives the title compound (12.86 g, 60%) as a clear liquid.

EXAMPLE 7

4-(2-diethylamino-ethoxy)-5-methoxy-fluoren-9-one

EXAMPLE 7A 4-(2-diethylamino-ethoxy)-5-methoxy-fluoren-9-one

In a manner similar to Example 2B, prepare the free base of $^2$-chloroethyl-dimethylamine hydrochloride (0.60 g, 3.5 mmole). As before, separately prepare a solution of 4-hydroxy-5-methoxy-fluoren-9-one (0.54 g, 2.4 mmole) in methanol (4 mL) and chlorobenzene (12 mL), heating to 130° C. while stirring for 30 minutes. Cool reaction to 100° C. before adding the free base of 2-chloroethyl-dimethylamine prepared previously in 15 mL chlorobenzene. Proceed as before in Example 2B to obtain the title compound as an orange-yellow powder (0.79 g, 91%). m.p. 188–191° C. (dec.).

Analysis calculated for C$_{20}$H$_{23}$NO$_3$: C, 66.38; H, 6.69; N, 3.87; C, 66.58; H, 6.51; N, 3.79.

The structure of the compound is the following:

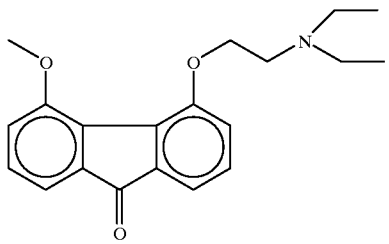

EXAMPLE 7B 4-hydroxy-5-methoxy-fluoren-9-one

Prepare a solution of 4-isopropoxy-5-methoxy-fluoren-9-one (0.78 g, 2.9 mmole) in methylene chloride (15 mL) and stir at 0° C. under an argon atmosphere. Dropwise add 9 mL (9.0 mmole) of boron trichloride (1.0 M in methylene chloride and stir the mixture for 1 hour, observing the color change to dark. Quench the reaction with 20 mL water, observing a mild exothermic reaction and an orange precipitate. Filter and wash the solid twice with 100 mL methylene chloride. Separate the organic layer from the filtrate and wash with brine. Dry over magnesium sulfate, filter and remove the solvent. Recrystalize the solid from chloroform/hexane (20:80; R$_f$=0.2) to give the title compound. Yield; 0.55 g, 84%.

The structure of the compound is the following:

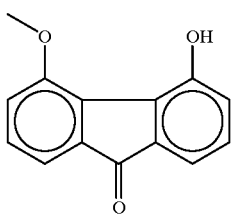

EXAMPLE 7C 4-isopropoxy-5-methoxy-fluoren-9-one

Prepare LDA reagent by combining 4.1 mL n-butyl lithium (2.5 M in hexane) and 1.4 mL diisopropylamine dropwise, under argon in 40 mL tetrahydrofuran (THF) at −50° C. Allow the reaction to warm to 0° C. and dropwise add N,N-diethyl-2'-isopropoxy-6-methoxy-biphenyl-2-carboxamide (1.4 g, 4.1 mmole) dissolved in THF (15 mL) while stirring. Maintain the temperature at 0° C. for 10 minutes, then allow the reaction to obtain room temperature, as the color slowly changes to yellow. Heat the reaction at reflux for about 2 hours and observe the yellow solution darken. Quench the reaction with saturated ammonium chloride, extract with ether and wash the organic layer with water. Recrystalize from ether/methanol to obtain an orange solid of the title compound (0.34 g, 1.3 mmole, 31%). m.p. 118–120° C.

The structure of the compound is the following:

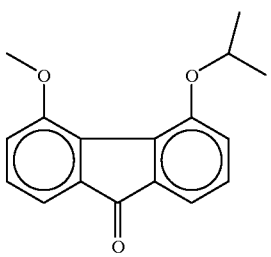

EXAMPLE 7D

N,N-diethyl-2'-isopropoxy-6-methoxy-biphenyl-2-carboxamide

Prepare a stirred solution of 2'-isopropoxy-6-methoxy-biphenyl-2-carboxylic acid (1.432 g, 0.0050 mole) in methylene chloride (50 mL) at −50° C. and under argon. Warm to ambient temperature then add thionyl chloride (0.8415 g, 0.516 mL). Continue stirring for about 45 minutes, observing the color change to light brown. Cool to 0° C. and dropwise add diethylamine (6.00 mL, 4.242 g, 0.058) mole, keeping the temperature of the reaction below 26° C. Continue stirring for about 30 minutes once the addition is complete. Dilute to 150 mL with additional methylene chloride. Wash the methylene chloride layer with water, separate, and extract twice with 100 mL 5% sodium bicarbonate. Separate, wash again with brine , separate and dry over MgSO$_4$. Filter through celite and condense on a rotary evaporator to a light brown, viscous liquid. Elute via chromatography with 30% ethyl acetate/70% hexane to give a clear viscous liquid (1.90 g). Concentrate under high vacuum to give a waxy solid of the title compound. (1.40 g, 82%).

EXAMPLE 7E

2'-isopropoxy-6-methoxy-biphenyl-2-carboxylic acid

Prepare a stirred mixture of 2-(2'-isopropoxy-6-methoxy-biphenyl)-4,4-dimethyl-4-oxazolium methyl iodide (7.10 g, 0.0127 mole) and 20% NaOH (60 mL) in methanol (60 mL) and heat at reflux for 20 hours under argon. The resulting solution is allowed to cool to ambient temperature then the methanol is evaporated on a rotary evaporator until the solution becomes turbid. Dilute this fine suspension to 200 mL with water, then acidify to pH=1 with concentrated HCl to precipitate the title compound. Extract into $CH_2Cl_2$ (200 mL), separate, wash with brine, separate again, dry over $MgSO_4$, filter and concentrate the filtrate to give the purified title compound as an off-white solid. (3.67 g, 87%). m.p. 139° C.–140° C.

The compound has the following structure:

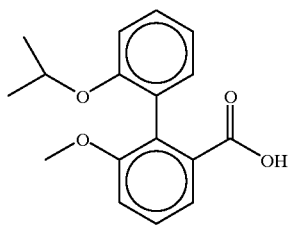

EXAMPLE 7F 2-(2'-isopropoxy-6-methoxy-biphenyl)-4,4-dimethyl-4-oxazolium methyl iodide Prepare a stirred solution of 2-(2'-isopropoxy-6-methoxy-biphenyl)-4,4-dimethyl-4-oxazoline (6.10 g, 0.0180 mole) in nitromethane ($CH_3NO_2$, ~50 mL), and add iodomethane (11.40 g, 0.080 mole) and continue stirring overnight. Dilute with ether (400 mL), and filter to give the title compound (7.10 g, 82%) as an off-white solid. m.p. 222°–224° C.

EXAMPLE 7G 2-(2'-isopropoxy-6-methoxy-biphenyl)-4,4-dimethyl-4-oxazoline

In a manner similar to Example 6F & 1A, dissolve 2-(2,3-dimethoxyphenyl)-4,4-dimethyloxazoline (4.70 g, 0.020 mole) in THF (50 mL) and add this to the Grignard prepared from 1-bromo-2-isopropoxybenzene (10.75 g, 0.050 mole) and Mg (1.22 g, 0.050 mole) in dry ether (75 mL). Work-up as in Example 6F to obtain the title compound as a pale yellow oil (6.30 g, 81%).

The structure of the compound is:

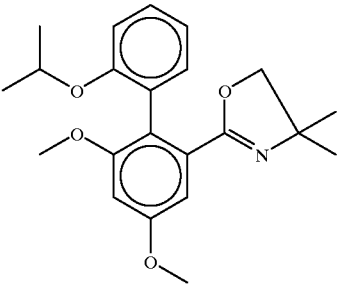

EXAMPLE 7H 1-bromo-2-isopropoxy-benzene

Prepare a stirred mixture of ortho-bromo-phenol (25.951 g, 17.4 mL, 0.15 mole) and potassium carbonate (20.70 g, 0.16 mole) in 175 mL isopropanol at ambient temperature under argon. Slowly add isopropyl iodide (22.2 g, 16.00 mL), heat at reflux and stir the mixture overnight. Cool to ambient temperature then filter, condensing the filtrate on a rotary evaporator. Dissolve the residual oil in diethyl ether (300 mL) and twice extract with 100 mL 50% sodium hyroxide. Separate, wash with brine and concentrate on a rotary evaporator to give a pale yellow liquid. Distill on the Kugelrohr (0.05 mm, 100°–120° C.) to obtain the title compound as an oil. (24.21 g, 75%).

EXAMPLE 8

5-(2-Diethylamino-ethoxy)-2,4-dimethoxy-fluoren-9-one

EXAMPLE 8A 5-(2-Diethylamino-ethoxy)-2,4-dimethoxy-fluoren-9-one

Similar to example 3D1, prepare a solution of 2,4-dimethoxy-5-hydroxy-fluoren-9-one (0.33 g, 1.3 mmol) in methanol (8 mL) and 24 mL chlorobenzene with sodium methoxide (0.11 g, 2.0 mmole), and react the free base of 2-chloro-ethyl-diethyl amine hydrochloride 2.1 g (12 mmole) in order to obtain 0.30 g of the title compound as a reddish-orange powder. m.p. 178° C.–180° C. Analysis calculated for C21H25NO4.HCl: C, 64.36; H, 6.69; N, 3.58. Found: C, 63.99; H, 6.75; N, 3.62.

EXAMPLE 8B 2,4-dimethoxy-5-hydroxy-fluoren-9-one

Prepare a solution of 5-isopropoxy-2,4-dimethoxy-fluoren-9-one (0.48 g, 1.6 mmole) in 25 mL $CH_2Cl_2$ and stir at 0° C. under argon. Dropwise, add boron trichloride (1.0 M in 1.8 mL $CH_2Cl_2$, 1.8 mmole) and stir the reaction for 1 hour. Quench with 20 mL water and stir vigorously. Filter and wash twice the resulting precipitate with 100 mL methylene chloride. Separate the organic layer from the filtrate and wash with brine. Dry with $MgSO_4$, filter and strip off the solvent. Recrystallize the solid from $CH_2Cl_2$/hexane (4:6) to obtain the title compound (0.28 g, 1.1 mmole, 69%). $R_f$=0.3.

51

The structure of the compound is:

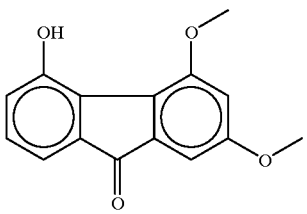

EXAMPLE 8C 5-isopropoxy-2,4-dimethoxy-fluoren-9-one

Similar to Example 7C prepare the LDA reagent by adding dropwise n-butyl lithium (8.2 mL, 21 mmole of 2.5 M) to diisopropyl amine (2.0 g, 2.8 mL/d=0.722, 20.3 mmol) at −50° C. in 50 mL tetrahydrofuran (THF) under argon. Allow reaction to warm to 0° C. then dropwise add N,N-diethyl-6-isopropoxy-2',4'-dimethoxy-biphenyl-2-carboxamide (3.0 g, 8.1 mmole) in 50 mL THF. Allow reaction to further warm to room temperature and stir overnight. Continue procedure from Example 7C to obtain 2.0 g (6.7 mmole, 83%) of the title compound. (EtOAc/hexane 4:6, Rf=0.50)

The structure of the compound is:

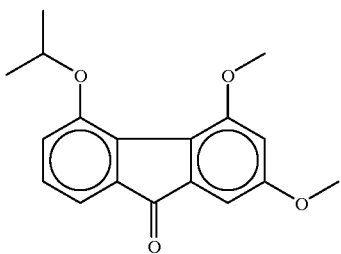

EXAMPLE 8D

N,N-diethyl-6-isopropoxy-2',4'-dimethoxy-biphenyl-2-carboxamide

Prepare a stirred solution of 6-isopropoxy-2',4'-dimethoxy-biphenyl-2-carboxylic acid (8.60 g, 0.0276 mole) in $CH_2Cl_2$ (200 mL) at ambient temperature under argon. Dropwise add thionyl chloride (4.6 g, 54 mmol, 2.8 mL). Continue stirring for about 60 minutes. Cool the reaction to 0° C. and dropwise add diethylamine (19.7 g, 28 mL, 0.27 mole), ensuring the temperature does not rise above 25° C. Continue stirring the reaction for about 30 minutes after addition is complete. Wash the organic layer with water, separate, and wash twice with 100 mL 5% sodium bicarbonate. Separate again, wash with brine (sat'd NaCl) and dry over magnesium sulfate. Filter through celite and condense on a rotovap to give a viscous light brown liquid. Dissolve (partially) in methylene chloride (20 mL) and filter. Flash chromatograph, in 30% ethyl acetate/70% hexane, to remove a solid impurity which is discarded. Continue eluting to obtain a mixture of the discardable and desired product. Further chromatography isolates the title compound as a pale yellow liquid (6.80 g, 68%). (EtOAc/hexane 30:70; $R_f$=0.15).

52

The structure of the compound is:

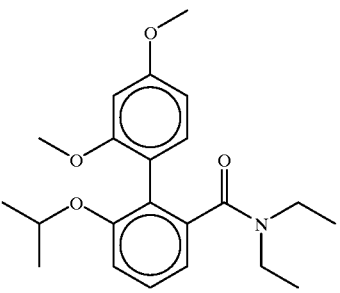

EXAMPLE 8E 2-isopropoxy-2',4'-dimethoxy-biphenyl-2-carboxylic acid

Prepare a mixture of 2-(2-isopropoxy-2',4'-methoxy-biphenyl-2-yl)-2,4,4-trimethyl-4-oxazolinium iodide (14.9 g, 29.1 mmole), 100 mL 20% sodium hydroxide and 100 mL methanol at room temperature, under argon. Heat and stir overnight, then allow to cool to room temperature then evaporate the methanol on a rotary evaporator. Dilute to about 300 mL with water, chill to 0° C. in an ice bath, then acidify to about pH 1.0 with concentrated hydrochloric acid. Extract into $CH_2Cl_2$, wash with brine, separate and dry over $MgSO_4$. Filter and evaporate to give the title compound (8.3 g, 26.3 mmole, 90%) as a brown glass. m.p. 121°–122° C.

EXAMPLE 8F 2-(2-isopropoxy-2',40-dimethoxy-biphenyl-2-yl)-2,4,4-trimethyl-4-oxazolinium iodide Prepare a solution of 2-(2-isopropoxy-2',4'-dimethoxy-biphenyl-2-yl)-2,4,4-trimethyl-4-oxazoline (13.2 g, 30.9 mmole in 40 mL dimethylsulfoxide (DMSO) under argon, at room temperature. Add methyliodide ($CH_3I$, 20.9 g, 0.21 mol), stir overnight, then pour into anhydrous ether (about 1.5 L). Continue stirring until an off-white solid completely precipitates. Filter the solid, then wash with anhydrous diethyl ether, filter and evaporate to give the title compound (14 g, 88%). m.p. 1920°–193° C.

EXAMPLE 8G 2-(2-isopropoxy-2',4'-dimethoxy-biphenyl-2-yl)-2,4,4-trimethyl-4-oxazoline Prepare a solution of magnesium (2.1 g, 86 mmole) in anhydrous diethyl ether (20 mL). Gently heat to initiate the reaction, then add dropwise 1-bromo-2,4-dimethoxy-benzene (18.7 g, 12.4 mL, 86.1 mmole). Once the addition is complete, add 70 mL anhydrous diethyl ether and heat to reflux for about 1 hour. Cool to room temperature and add dropwise 2-(2,3-diisopropoxy-phenyl-2-yl)-4,4-dimethyl oxazoline (9 g, 30.9 mmole) in 50 mL anhydrous tetrahydrofuran. Stir overnight, then quench with saturated aq. $NH_4Cl$ (75 mL). Separate the organic layer, wash with brine, separate and dry over magnesium sulfate. Filter and concentrate on the rotary evaporator. Dissolve the resulting purple liquid in ethyl acetate (250 mL) and extract with 210 mL 5% hydrochloric acid. Separate the aqueous layer, wash with brine, separate and dry over magnesium sulfate. Filter through celite and evaporate on the rotary evaporator to give 13.20 g of the title compound as a green oil.

$^1$H-NMR δ1.11 (6H, d, CH$_3$), 1.21 (3H, s, CH$_3$), 1.22 (3H, s, CH$_3$), 3.63 (1H, d, CH$_2$), 3.70 (3H, s, OCH$_3$), 3.74 (1H, d, CH$_2$), 3.83 (3H, s, OCH$_3$), 4.32 (1H, m, CH), 6.45–6.49 (2H, m, ArH), 7.00–7.05 (2H, m, ArH), 7.26 (1H, t, ArH), 7.33 (1H, d, ArH).

EXAMPLE 8H 2-(2,3-diisopropoxy-phenyl-2-yl)-4,4-dimethyl oxazoline

Prepare a solution of N-(2-Hydroxy-1,1-dimethyl-ethyl)-2,3-diisopropoxy-benzamide (9.30 g, 0.030 mole) in methylene chloride (8.00 mL) at 0° C. under argon, then dropwise add thionyl chloride (6.80 mL/d=1.632, 11.08 g, 0.131 mole) Keep the temperature of the reaction below 5° C. during the addition, then warm to ambient temperature and stir for about 1.5 hours. Dilute with ethyl acetate up to 150 mL and and pour into water chilled to 0° C. Separate the aqueous layer, neutralize it with solid potassium carbonate to pH=9.0 and further extract with ethyl acetate. Wash the ethyl acetate (about 300 mL) with brine, separate and dry over magnesium sulfate. Filter and condense on the rotary evaporator to give 6.7 g (82%) of the title compound. (R$_f$=0.24; (EtOAc/hexane, 3:7).

EXAMPLE 8I

N-(2-hydroxy-1,1-dimethyl-ethyl)-2,3-diisopropoxy-benzamide

Add 60% sodium hydride (9.20 g, 0.23 mole) portion wise to a stirred solution of 2-amino-2-dimethyl-propanol (9.20 g, 0.23 mole) dissolved in THF (200 mL). Stir continuously for 1 hour under argon at ambient temperature then add dropwise 2,3-diisopropoxy-methyl benzoate (25.35 g, 0.100 mole) dissolved in THF (60 mL). Stir the resulting mixture overnight at ambient temperature, then cautiously add water (4.00 mL). Evaporate to a brown pasty oil on the rotary evaporator. Dissolve the residue in ethyl acetate/water mixture and separate the EtOAc phase. Wash with brine, separate and dry over magnesium sulfate. Filter and evaporate to obtain the title amide.

The structure of the compound is:

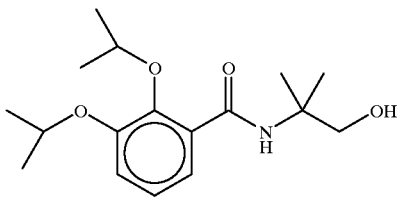

EXAMPLE 8J 2,3-diisopropyl methyl benzoate

Prepare a stirred solution of isopropyl iodide (72.19 g, 0.425 mole) and 2,3-dihydroxy methyl benzoate (23.80 g, 0.1415 mole) in 2-butanone (300 mL) under argon, add potassium carbonate (55.2 g, 0.400 mole) and heat the mixture to reflux under argon. Cool the mixture to ambient temperature and filter. Concentrate the filtrate to obtain a yellow liquid. Extract into a mixture of ether/water (100 mL) and separate the ether phase. Extract with 5% NaOH (2×250 mL), separate, wash with brine, dry over MgSO$_4$, filter and evaporate to give 25.60 g. (72%) of a yellow liquid.

EXAMPLE 8K

Methyl 2,3-dihydroxy-benzoate

Prepare a reaction flask with 300 mL methanol and add 30 mL of acetyl chloride, under argon, in an ice bath. Add 2,3-dihydroxy-benzoic acid (21.70 g, 0.1418 mole) and stir while heating at reflux overnight. Chill in an ice bath and bubble through hydrogen chloride gas for about 10 minutes. Heat the mixture and stir at reflux overnight. Cool to ambient temperature, then concentrate to an off-white solid. Dissolve and separate into diethyl ether and water. Isolating the ether portion and extract twice with 250 mL 5% sodium bicarbonate. Separate, wash with brine and dry over magnesium sulfate. Filter and condense on a rotary evaporator to give the title compound as an off-white solid (21.1 g, 99%). m.p. 79°–81° C.

EXAMPLE 9

1-Amino-5-(2-diethylamino-ethoxy)-2,4-dimethoxy-fluoren-9-one

EXAMPLE 9A

1-Amino-5-(2-diethylamino-ethoxy)-2,4-dimethoxy-fluoren-9-one hydrochloride

Prepare a mixture of 5-(2-diethylamino-ethoxy)-2,4-dimethoxy-1-nitro-fluoren-9-one (0.08 g, 0.18 mmole) and stannous chloride dihydrate (SnCl$_2$.2H$_2$O, 0.80 g, 3.5 mmole) in 20 mL ethanol. Heat at 70° C. under argon overnight. Dilute with about 60 mL water and make slightly basic by addition of 5% sodium bicarbonate. Extract the precipitate with ethyl acetate and dry over magnesium sulfate. Filter and evaporate the solvent. Make acidic (to pH=2) with 5% hydrochloric acid and extract the organics. Make the aqueous phase basic (to pH=8) and extract with methylene chloride. Dry over magnesium sulfate. Filter and evaporate the solvent to obtain a red oil. Chromatron with 7% methanol in methylene choride and condense under high vacuum to obtain the free base of the title compound (0.48 g). m.p. 208°–210° C.

Dissolve the free base obtained above into ether (~20 mL) and acidify with excess ethereal HCl. Collect and dry the precipitated red solid to obtain the title compound. m.p. 208°–210° C.

The structure of the compound is:

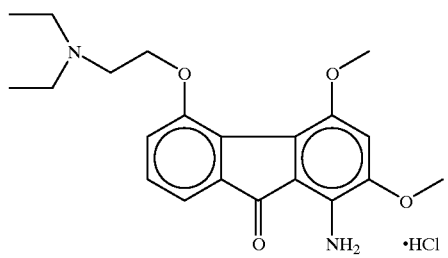

EXAMPLE 9B 5-(2-diethylamino-ethoxy)-2,4-dimethoxy-1-nitro-fluoren-9-one

Prepare a solution of 5-hydroxy-2,4-dimethoxy-1-nitro-fluoren-9-one (0.5 g, 1.6 mmole) in anhydrous methanol 4 mL and 20 mL chlorobenzene. Add sodium methoxide (0.11 g, 2.0 mmole) and heat under argon to evaporate the methanol. When the temperature reaches 130° C., cool to 100° C. and add the free base of 2-chloro-ethyl-diethyl amine in 25 mL chlorobenzene (prepared analogously as in Example 2B). Once the addition is complete, heat to reflux overnight. Cool to room temperature, then pour the reddish mixture into 100 mL of 1% sodium hydroxide. Separate, flash with brine and dry the organic layer with magnesium sulfate. Filter and strip the solvent. Dry under high vacuum then take-up in ether and add ethereal HCl dropwise to precipitate the product. Chromatograph by eluting with methanol/CH$_2$Cl$_2$10:90 to give the title compound. (0.10 g, 16%).
MS CI (M+H)$^+$ 401.

EXAMPLE 9C 5-hydroxy-2,4-dimethoxy-1-nitro-fluoren-9-one

Prepare a solution of 5-isopropoxy-2,4-methoxy-fluoren-9-one (1.5 g, 5.0 mmole) in 70 mL anhydrous methylene chloride at −78° C. under argon, and add nitro-tetrafluoroborane (0.72 g, 5.4 mmole). Stir for about 5 hours, then warm to room temperature and stir overnight. Quench the reaction with water and extract with methylene chloride. Wash with brine and dry the organic layer with magnesium sulfate. Filter and strip the solvent to obtain a black solid in a pasty oil. Triturate with EtOAc and filter off a red solid to obtain the title compound (0.5 g).

EXAMPLE 9D 5-isopropoxy-2,4-methoxy-fluoren-9-one

Prepare LDA reagent by adding dropwise n-butyl-lithium (8.2 mL of 2.5 M, 21 mmole) to diisopropyl amine (2.0 g, 2.8 mL, 20.2 mmole) in 50 mL anhydrous tetrahydrofurn (THF) at −50° C. When the addition is complete, warm to 0° C. while stirring. Cool to −10° C. and add dropwise N,N-diethyl-6-isopropoxy-1',4'-dimethoxy-biphenyl-2-carboxamide (3.0 g, 8.1 mmole) in 20 mL THF. Warm to room temperature and stir overnight. Quench the reaction with saturated ammonium chloride, whereupon the clear orange solution turns dark red. Purify in a chromatotron with 40% ethyl acetate/hexame, and evacuate under a high vacuum to obtain the title compound as a red solid (1.9 g, 6.3 mmole, 79%).

EXAMPLE 9E

N,N-diethyl-6-isopropoxy-1',4'-dimethoxy-biphenyl-2-carboxamide

In a manner similar as described in Example 8D, react together 6-isopropoxy-2',4'-dimethoxy-biphenyl-2-carboxylic acid (8.3 g, 26.2 mmole), and thionyl chloride (4.5 g, 2.7 mL, 52 mmole) in CH$_2$Cl$_2$ (200 mL) and diethylamine (19.0 g, 27 mL, 260 mmol). Continue as in Example 8D to obtain the title compound (7.9 g, 81%).

EXAMPLE 9F 6-isopropoxy-2',4'-dimethoxy-biphenyl-2-carboxylic acid

In a manner similar as described in Example 8E, react together 2-(6-isopropoxy-2',40-dimethoxy-biphenyl-2-yl)-3,4,4-trimethyl-4-oxazolinium iodide (14.9 g, 29.1 mmole), 20% sodium hydroxide (100 mL) and methanol (100 mL). Continue as in Example 8E, except acidify to pH=2 after diluting to 300 mL with water, to obtain the title compound as a brown glass (8.3 g, 90%).

EXAMPLE 9G 2-(6-isopropoxy-2',4'-dimethoxy-biphenyl-2-yl)-3,4,4-trimethyl-4-oxazolinium iodide In a manner similar as described in Example 8F, react together 2-(6-isopropoxy-2',4'-dimethoxy-biphenyl-2-yl)-3,4,4-trimethyl-4-oxazoline (2.73 g, 0.0074 mole) and methyl iodide (9.9887 g, 0.0074 mole) in anhydrous dimethyl sulfoxide to obtain the title compound. Yield=14.2 g, 88%. The structure of the compound is:

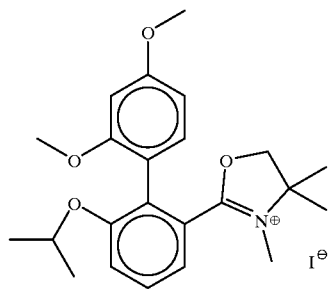

EXAMPLE 9H 2-(6-isopropoxy-2',4'-dimethoxy-biphenyl-2-yl)-3,4,4-trimethyl-4-oxazoline Prepare a mixture of anhydrous diethyl ether (20 mL) and magnesium (2.1 g, 86 mmole). Dropwise add 1-bromo-2,4-dimethoxybenzene (4.1 g, 27.5 mL, 0.22 mole) while stirring. Gently heat to initiate the reaction. Iodine crystals and/or 1,2-bromoethane are added as needed to initiate the reaction. Continue addition of the ether at a rate sufficient to maintain reflux. After the addition is complete, add diethyl ether (100 mL) and heat to reflux for about 1 hour. Cool to room temperature and dropwise add 2-(2,3-diisopropoxy-2-yl)-4,4-dimethyl-4-oxazoline (9 g, 30.9 mmole) in 50 mL anhydrous tetrahydrofuran (THF). Stir overnight, then quench with aqueous ammonium chloride (75 mL of saturated solution). Separate the organic layer and extract the aqueous layer with 100 mL THF. Wash the combined organic layers twice with brine, dry with magnesium sulfate, filter and rotovap. Dissolve the residue in 10% hydrochloric acid (30 mL concentrated diluted to 120 mL) and wash twice with 100 mL diethyl ether to precipitate the chloride salt of the title compound. Prepare the free base by making the aqueous layer basic with 50% sodium hydroxide and extract twice with 250 mL ethyl acetate. Dry the organic layer with magnesium sulfate, filter and rotovap to give 13.2 g of a green oil.

EXAMPLE 10

1-Amino-5-(2-diethylamino-ethoxy)-4-methoxy-2-propoxy-fluoren-9-one

EXAMPLE 10A

1-Amino-5-(2-diethylamino-ethoxy)-4-methoxy-2-propoxy-fluoren-9-one

Prepare a solution, under argon, of 5-(2-diethylamino-ethoxy)-4-methoxy-1-nitro-2-propoxy-fluoren-9-one (0.52 g, 1.2 mmole) and stannous chloride (SnCl$_2$, 1.3 g, 6 mmole) in 60 mL ethanol. Reflux overnight. Reduce volume on a rotovap. Add 200 mL deionized water and make basic with sodium bicarbonate. Extract with methylene chloride. Dry the organic layer with magnesium sulfate. Filter and evaporate on a rotary evaporator to give a red oil. Take up in anhydrous diethyl ether and filter through celite. Precipitate the hydrochloride salt by adding ethereal HCl. Filter the resulting red solid and wash with diethyl ether. Place under a high vacuum overnight at 100° C. to give the purified hydrochloride salt of the title compound. m.p. 163–165° C. Yield 0.338 g, 70%. R$_f$=0.33; 5% methanol/CH$_2$Cl$_2$.

Anal. Calc'd for: C$_{23}$H$_{30}$N$_2$O$_4$.HCl: C, 63.51; H, 7.18; N, 6.44. Found C, 63.42; H, 7.27; N, 6.31.

The structure of the compound is:

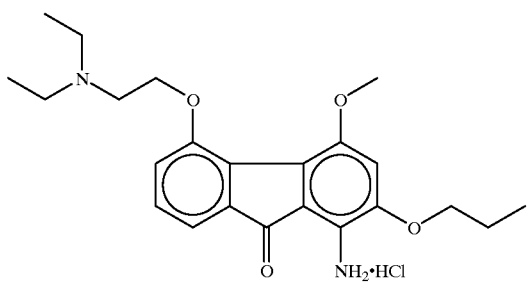

EXAMPLE 10B 5-(2-diethylamino-ethoxy)-4-methoxy-1-nitro-2-propoxy-fluoren-9-one Prepare a solution of 5-(2-diethylamino-ethoxy)-4-methoxy-2-propoxy-fluoren-9-one (1.1 g, 2.9 mmole) in 100 mL anhydrous methylene chloride at −72° C. under argon while stirring. Add nitronium tetrafluoroborate (0.42 g, 3.2 mmole) in one continuous portion. Allow the mixture to warm to room temperature for 3 hours while the solution darkens. Stir an additional 2 hours, then check reaction progress with an aliquot by thin layer chromatography. Quench the reaction with water and transfer to a seperatory funnel. Retain the organic layer and filter off an insoluble red solid from the interface. Wash with water and methylene chloride. Take up the solid into 5% sodium hydroxide and stir vigorously. Extract with methylene chloride and chromatotron the organics, combine the CH$_2$Cl$_2$ fractions and dry over MgSO$_4$, filter and concentrate on the rotary evaporator. Chromatograph the resulting residue, eluting with methanol/CH$_2$Cl$_2$ (5:95) to obtain 0.52 g (52%) of the title compound.

CI-MS [M+H]$^+$=429.

EXAMPLE 10C 5-(2-diethylamino-ethoxy)-4-methoxy-2-propoxy-fluoren-9-one

In a manner analagous to Example 9B, react 5-hydroxy-2-propoxy-4-methoxy-fluoren-9-one (1.75 g, 6.1) in 5 mL methanol and 100 mL chlorobenzene with 2-chloroethyldiethyl amine hydrochloride (4.4 g, 25 mmole) and sodium methoxide (0.51 g, 9.5 mmole) and reflux for 2 hours then continue as in Example 9B to give 1.1 g. of the title compound (2.9 mmole, 47%).

m.p. 127°–129° C.

EXAMPLE 10D

5-Hydroxy-2-propoxy-4-methoxy-fluoren-9-one

Prepare a stirred solution of 5-isopropoxy-2-propoxy-4-methoxy-fluoren-9-one (2.2 g, 6.7 mmole) in 100 mL methylene chloride at 0° under argon. Dropwise add boron trichloride (15.4 mL of 1.0 M in methylene chloride, 15.4 mmole). Monitor the reaction by TLC on aliquots, in 40% ethyl acetate/hexane, quenching with saturated ammonium chloride. After 1 hour, quench the reaction with saturated ammonium chloride. Filter and wash twice with 1.00 mL methylene chloride. Separate the organic layer from the filtrate and wash with brine. Dry with magnesium sulfate, filter and strip the solvent. Chromatograph the crude product dissolving first in methylene chloride, then eluting in 30% ethyl acetate/hexane to give the title compound as a red powder (1.75 g, 6.1 mmole, 92%). R$_f$=0.54 (EtOAc/hex., 40:60).

The compound has the following structure:

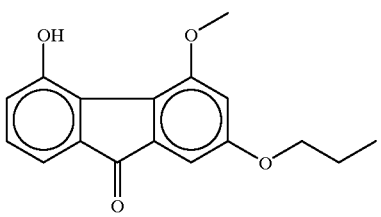

EXAMPLE 10E 5-isopropoxy-2-propoxy-4-methoxy-fluoren-9-one

Prepare LDA reagent by reacting n-butyl lithium and diisopropylamine as in Example 7C to obtain 0.05 mole in THF (50 mL) at 0° C. At 0° C., dropwise add N,N-diethyl-6-isopropyloxy-2'-methoxy-4'-propyloxy-biphenyl-2-carboxamide (4.3 g, 0.011 mole) in THF (20 mL). Warm the mixture to ambient temperature, stir for 1 hour then heat to reflux for 1.5 hours. Workup the mixture as in Example 7C and chromatograph eluting with 50%/50% EtOAc/hexane to give the title compound as a red solid (2.6 g, 63%). m.p. 114°–116° C.

EXAMPLE 10F

N,N-diethyl-6-isopropoxy-2'-methoxy-4'-propoxy-biphenyl-2-carboxamide

Prepare a stirred solution of 6-isopropoxy-1-methoxy-4-propoxy-biphenyl-2-carboxylic acid (5.8 g, 16.8 mmole) in CH$_2$Cl$_2$ (100 mL) at ambient temperature, under argon. Add thionyl chloride (2.8 g, 0.516 mL/d=1.632) and continue stirring for about 60 minutes. Check the reaction progress by TLC. After about 1.3 hours, cool to 0° C. and dropwise add diethylamine (9.9 g, 0.135 mole, 14.00 mL), taking care to ensure the temperature does not exceed 26° C. Stir for an additional 30 minutes after the addition is complete then dilute to 100 mL with methylene chloride. Wash with water, separate and wash twice with 100 mL 5% sodium bicarbonate. Separate, wash with brine, separate and dry with magnesium sulfate. Filter through celite and condense on the rotary evaporator. Chromatograph, eluting with 40% ethyl acetate-60% hexane to give 4.3 g (0.011 mole, 64%) of the title compound. R$_f$=0.33

$^1$H-NMR (CDCl$_3$) δ0.68 (3H, t, CH$_3$), 0.84 (3H, t, CH$_3$), 1.02 (3H, t, CH$_3$), 1.05 (3H, d, CH$_3$), 1.18 (3H, d, CH$_3$), 1.80 (2H, m, CH$_2$), 2.65 (1H, m, CH$_2$), 2.82 (1H, m, CH$_2$), 3.19 (1H, m, CH$_2$), 3.70 (3H, s, OCH$_3$), 3.72 (1H, m, C$_2$), 3.91 (2H, t, OCH$_2$), 4.35 (1H, m, CH), 6.44 (1H, s, ArH), 6.46 (1H, d, ArH), 6.91 (2H, d, ArH), 7.15 (1H, d, ArH), 7.27 (1H, t, ArH).

The structure of the compound is:

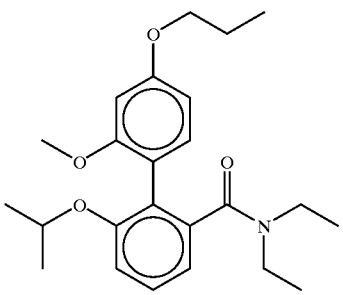

EXAMPLE 10G 6-isopropoxy-1'methoxy-4-propoxy-biphenyl-2-carboxylic acid

In a manner analogous to Example 9F, react 2-(6-isopropoxy-1'methoxy-4'-propoxy-biphenyl-2-yl)-3,4,4-trimethyl-4-oxazolinium iodide (9.2 g, 17 mmole) and 20% aqueous sodium methoxide (50 mL) in methanol (50 mL) to give 5.8 g (16.8 mmole, 99%) of the title compound.

$^1$H-NMR (CDCl$_3$) δ1.10 (3H, t, CH$_3$), 1.11 (3H, d, CH$_3$), 1.19 (3H, d, CH$_3$), 1.87 (2H, m, CH$_2$), 3.68 (3H, s, OCH$_3$), 4.00 (2H, t, OCH$_2$), 4.30 (1H, m, CH), 6.50 (1H, s, ArH), 6.52 (1H, d, ArH), 7.10 (1H, d, ArH), 7.16 (1H, d, ArH), 7.33 (1H, t, ArH), 7.53 (1H, d, ArH).

EXAMPLE 10H 2-(6-isopropoxy-1'-methoxy-4'-propoxy-biphenyl-2'-yl)-3,4,4-trimethyl-4-oxazolinium iodide In a manner analogous to Example 9G, react 2-(6-isopropoxy-1'-methoxy-4'-propoxy-biphenyl-2-yl)-4,4-dimethyl-4-oxazoline (8.1 g, 20 mmole) and methyl iodide (12.8 g, 5.6 mL, 90 mmole) in 20 mL dimethylsulfoxide. After the reaction, dilute with 500 mL anhydrous, diethyl ether, and pour the mixture into an additional 1.5 L diethyl ether and stir about 15 minutes. Filter and wash with diethyl ether. Take up solids into methylene chloride and filter to remove a white precipitate. Strip the solvent under high vacuum to obtain the title compound (9.2 g, 85%). m.p. 198°–201° C.

EXAMPLE 10I 2-(6-isopropoxy-1'-methoxy-4'-propoxy-biphenyl-2-yl)-4,4-dimethyl-4-oxazoline In a manner analogous to Example 9H, react magnesium (0.73 g, 30 mmole), 2-(2,3-diisopropoxy)-4,4-dimethyl-4-oxazoline (8.0 g, 27.5 mmole) with 1-bromo-2-methoxy-4-propoxy-benzene (6.9 g, 28 mmole) in 30 mL diethyl ether and 30 mL tetrahydrofuran to obtain the title compound (8.1 g, 20.4 mmole, 74%). (R$_f$=0.25; EtOAc/hexane 40:60)

The structure of the compound is:

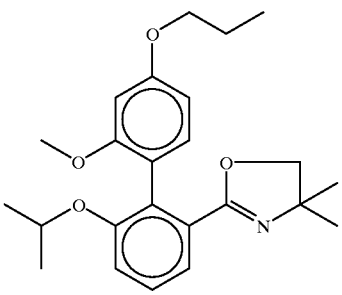

EXAMPLE 10J 1-bromo-2-methoxy-4-propoxy-benzene

Prepare a solution of 4-bromo-3-methoxyphenol (6.5 g, 32 mmole), and potassium carbonate (15 g) in acetone (250 mL) under argon. Add n-propyl iodide (9.0 g, 5.2 mL, 53 mmole) and heat to reflux overnight. Cool to room temperature and filter. Rotovap to condense and evaporate the solvents. Check by thin layer chromatagraphy (25% ethyl aceate/75% hexane). Wash three times with 100 mL 3% potassium hydroxide. Dry the organic layer with magnesium sulfate. Filter and rotovap. Purify by chromatography and place under high vacuum to obtain the title compound (6.9 g, 88%). Rf=0.60 (EtOAc/hexane; 25:75).

EXAMPLE 11

5-(-2-pyrrolidinyl-ethoxy)-1-amino-4-methoxy-2-propyloxy-fluoren-9-one hydrochloride

EXAMPLE 11A 5-(-2-pyrrolidinyl-ethoxy)-1-amino-4-methoxy-2-propyloxy-fluoren-9-one hydrochloride 5-(2-Pyrrolidinyl-ethoxy)-4-methoxy-2-propoxy-1-nitro-fluoren-9-one (0.30 g, 0.7 mmol) and stannous chloride dihydrate (1.0 g, 0.7 mmol) are reacted as described in Example 9A to give the title compound (0.10 g, 33%). m.p. 122°–124° C.

The compound has the following structure:

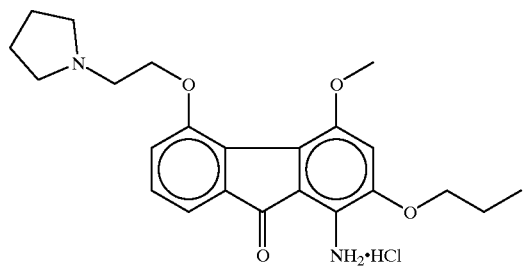

EXAMPLE 11B 5-(-2-pyrrolidinyl-ethoxy)-4-methoxy-2-propyloxy-1-nitro-fluoren-9-one 5-(2-Pyrrolidinyl-ethoxy)-4-methoxy-2-propyloxy-1-nitro-fluoren-9-one (0.35 g, 0.92 mmole) and nitronium tetrafluoroborate (0.13 g, 0.92 mmole) in CH$_2$Cl$_2$ (20 mL) are reacted as described in Example 9C to give the title compound.

EXAMPLE 11C

5-(2-pyrrolidinyl-ethoxy)-4-methoxy-2-propyloxy-fluoren-9-one hydrochloride

5-Hydroxy-4-methoxy-2-propyloxy-fluoren-9-one (0.83 g, 2.9 mmole) and 2-chloroethylpyrrolidine and sodium methoxide (0.20 g, 3.5 mmole) are reacted as described in Example 9B to give a red powder, which when recrystallized from 2-butanone gives the title compound. (0.222 g, 18%). m.p. 147°–149° C. Analysis calculated for $C_{23}H_{27}NO_4 \cdot HCl$; C, 66.10, H, 6.75, N, 3.35. Found: C, 65.82, H, 6.65; N, 3.09. The compound has the following structure:

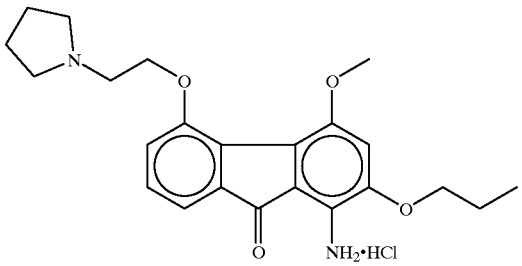

EXAMPLE 12

5-[2-(morpholino-4-yl)-ethoxy]-1-amino-4-methoxy-2-propyloxy-fluoren-9-one hydrochloride

EXAMPLE 12A

5-[2-(morpholino-4-yl)-ethoxy]-1-amino-4-methoxy-2-propyloxy-fluoren-9-one hydrochloride 5-[2-(morpholino-4-yl)-ethoxy]-4-methoxy-2-propyloxy-1-nitro-fluoren-9-one hydrochloride (0.20 g, 0.45 mmole) and stannous chloride dihydrate ($SnCl_2 \cdot H_2O$; 1.0 g, 4.4 mmole) were reacted as described in Example 9A to give the hemihydrate of the title compound (0.765 g, 38%) as a dark-red solid. m.p. 128°–131° C.

Analysis calculated for $C_{23}H_{28}N_2O_5 \cdot HCl \cdot 5H_2O$: C, 60.46; H, 6.40; N, 6.13. Found: C, 60.15; H, 6.37; N, 6.04. The structure corresponds to the following formula:

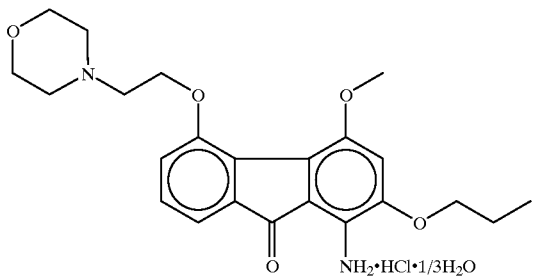

EXAMPLE 12B

5-[2-(morpholino-4-yl)-ethoxy]-4-methoxy-2-propyloxy-1-nitro-fluoren-9-one

5-[2-(Morpholino-4-yl)-ethoxy]-4-methoxy-2-propyloxy-fluoren-9-one (0.18 g, 0.45 mmole) and nitronium tetrafluoroborate (0.5 M in sulfolane; 1.0 mL, 0.5 mmole) in $CH_2Cl_2$ (20 mL) are stirred together at −78° C. for 2 hours, then allowed to warm to ambient temperature and stirred again for about 60 hours. Quench the reaction with saturated $NH_4Cl$, then separate. Extract the organic layer with water 3X, separate, wash with brine and separate. Dilute the $CH_2Cl_2$ layer with additional $CH_2Cl_2$ and dry over $MgSO_4$. Filter and evaporate to give the title compound as a red oil (0.2 g). Rf=0.45 ($MeOH/CH_2Cl_2$; 5:95).

EXAMPLE 12C

5-[2-(morpholino-4-yl)-ethoxy]-4-methoxy-2-propyloxy-fluoren-9-one hydrochloride 5-Hydroxy-4-methoxy-2-propoxy-fluoren-9-one (0.40 g, 1.4 mmole), 2-chloroethyl-morpholine (0.84 g, 5.6 mmole) and sodium methoxide (0.10 g, 1.8 mmole) are reacted as described in Example 9B. Remove the chlorobenzene on the rotovap, mix the residue with water as needed to redissolve the residue, and heat on a steam bath. Remove the insoluble solid by filtration on a sintered glass funnel, wash with water and dry to give 0.187 g of the free base corresponding to the title compound. Convert the free base to the hydrochloride with ethereal HCl and dry to give the title compound as an orange powder. m.p. 184°–186° C. Analysis calculated for $C_{27}H_{27}NO_5 \cdot HCl$: C, 63.66; H, 6.50; N, 3.23. Found: C, 63.48; H, 6.57; N, 2.99.

EXAMPLE 12D 5-hydroxy-4-methoxy-2-propoxy-fluoren-9-one
See Example 11C

III. Bis-basic, alkoxy fluorenones

EXAMPLE 13

1-Amino-2,5-bis-(diethylamino-ethoxy)-4-methoxy-fluoren-9-one

EXAMPLE 13A

1-Amino-2,5-bis-(diethylamino-ethoxy)-4-methoxy-fluoren-9-one hydrochloride 2,5-Bis-(2-diethylamino-ethoxy)-1-nitro-4-methoxy-1-nitro-fluoren-9-one hydrochloride (0.37 g, 0.70 mmol) and stannous chloride dihydrate ($SnCl_2 \cdot 2H_2O$; 1.0 g, 0.7 mmol) are reacted as described in Example 9A to give the title compound which has the following structural formula:

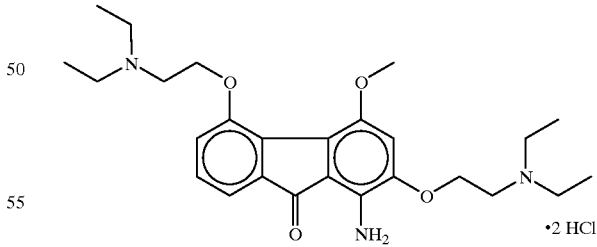

EXAMPLE 13B

2,5-Bis-2-(diethylamino-ethoxy)-4-methoxy-1-nitro-fluoren-9-one 2,5-Bis-2-(diethylamino-ethoxy)-4-methoxy-fluoren-9-one (0.476 g, 0.92 mmo) and nitronium tetrafluoroborate (0.13 g, 0.92 mmol) in $CH_2Cl_2$ (20 mL) are reacted as described in Example 9C to give the title compound.

EXAMPLES 13C–H 2,5-Bis-2-(diethylamino-ethoxy)-4-methoxy-fluoren-9-one

The starting material for Example 13B may be prepared as in Example 4A, which can be synthesized as in Examples 4B to 4F.

For Examples 14 and 15, melting points are uncorrected. 1H-NMR spectra and 13C NMR were obtained at 300 MHz and 75 MHz, respectively. Chemical shifts are reported in d values relative to Me4Si (d=0.00) as an internal standard for 1H spectra.

EXAMPLE 14

Alternative Preparation of 2,5-dihydroxy-4-methoxy-fluoren-9-one (Dengibsin)

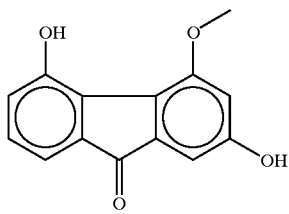

EXAMPLE 14A

1-Bromo-2-methoxy-4-(1-methylethoxy)benzene

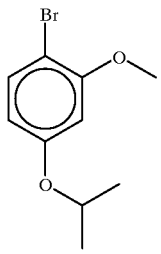

To a stirred suspension of 4-bromo-3-methoxyphenol (2.03 g, 10 mmol) and $K_2CO_3$ (1.38 g, 10 mmol) in 2-butanone (70 mL) at ambient temperature under argon is added dropwise isopropyl iodide (2.21 g, 13.3 mmol). The resulting mixture is heated and stirred under reflux for 17 hours. The mixture is allowed to cool to ambient temperature then is filtered and concentrated by evaporation of the solvent. The residue is partitioned between $Et_2O$ and $H_2O$. The $Et_2O$ layer is extracted with 5% NaOH (2×50 mL), washed with brine, and dried over $MgSO_4$. The solvent is evaporated and the resulting residue is purified by flash chromatography (5% EtOAc/hexane) to afford the desired compound as a pale yellow oil. 2.13 g (87%).

UV (MeOH) 1 max=283 nm, e=9,510; $^1$H NMR (CDCl$_3$) (d, 1H,J=8.6 Hz), 6.47 (1H, d, J=2.7 Hz), 6.38 (1H, dd, J=8.5,2.7 Hz), 4.5 (1H, hept.,J=6.3 Hz), 3.85 (3H, s) 1.33 (6H, d, J=6.3 Hz);

$^{13}$CNMR (CDCl$_3$) d 158.4, 156.6, 133.0, 107.7, 102.0, 101.8, 70.3, 56.0, 21.9; Anal. Calcd for $C_{10}H_{13}BrO_2$; C, 49.00; H,5.35. Found: C, 48.87; H, 5.12.

EXAMPLE 14B 4,5-Dihydro-2-[2,3-bis(1-methylethoxy)-1-phenyl]-4,4-dimethyloxazole

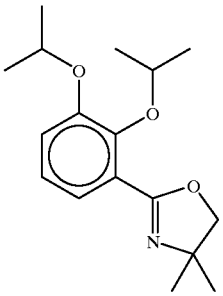

Sodium hydride (8.25 g, 60%, 0.205 mol) is added portionwise to a stirred solution of 2-amino-2-methyl propanol (17.52 g, 0.196 mol) in dry THF (200 ml). The mixture is stirred at ambient temperature for 1 hour. To this solution is added methyl 2,3-di-isopropoxybenzoate (24.82 g, 0.098 mol) dissolved in THF (50 mL). The mixture is stirred overnight under argon, quenched with $H_2O$ (4 mL) and concentrated by evaporation of the solvent. The residue is dissolved in $CH_2Cl_2$ extracted with $H_2O$, washed with brine and dried over $MgSO_4$. Filtration and evaporation of the solvent gives 33.3 g of a yellow liquid. To this crude product dissolved in $CH_2Cl_2$ (30 mL) is added dropwise $SOCl_2$ (19 mL, 0.37 mol) at 0 to 5° C. Following the addition the reaction mixture is allowed to warm to ambient temperature and stirred for 1.5 hours. The mixture is diluted with EtOAc (300 ml), poured into ice water (500 ml) and the aqueous layer is separated and neutralized with solid $K_2CO_3$ to pH=9. The EtOAc is washed with brine, dried with $MgSO_4$ and filtered. The solvent is evaporated and final traces of solvent are removed under high vacuum to give the title compound as a yellow liquid: 23.6 g (83%) overall. $^1$H NMR (CDCl$_3$)d 7.29–7.27 (1H, m), 6.99–6.98 (2H, m), 4.55 (1H, sept., J=6.1 Hz), 4.44 (1H, sept., J=6.1 Hz), 4.09 (2H, s), 1.38 (6H, s), 1.31 (3H, d, J=6.1 Hz), 1.27 (6H, d, J=6.1 Hz).

EXAMPLE 14C 4,5-Dihydro-2-[2'-methoxy-4',6-bis(1-methylethoxy) 1,1'-biphenyl-2-yl]-4,4-dimethyloxazole

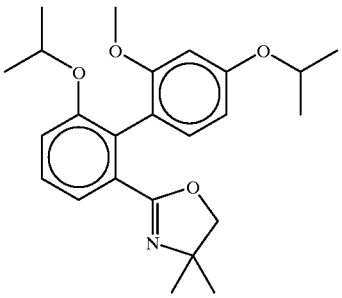

To a stirred suspension of Mg (0.917 g, 37.7 mmol), a crystal of $I_2$, and 3 drops of ethylene dibromide is added dropwise 10 mL of a solution of 1-bromo-2-methoxy-4-(1-methylethoxy)benzene (8.51 g, 34.7 mmol) dissolved in THF (30 mL). The mixture is warmed to 40° C. the 1-bromo-2-methoxy-4-(1-methylethoxy)benzene prepared previously is added. After the reaction moderated, the mixture is heated at 50° C. for 40 min. To this solution is added the oxazoline prepared above (11.27 g, 38.0 mmol) in THF (30 mL) dropwise at ambient temperature. The reaction mixture warms 10° C. during the addition. The reaction mixture is heated and stirred at 50° C. overnight. The mixture is chilled in an ice bath and quenched with saturated NH$_4$Cl. The THF layer is washed with brine, dried over MgSO$_4$ and filtered. The solvent is evaporated and the residue is purified by flash chromatography (40% EtOAc/ hexane) to give the title compound as a pale yellow oil: 11.34 g (81%). $^1$H NMR(CDCl$_3$) d 7.32 (1H, dd, J=7.8, 1.3 Hz), 7.28 (1H, dd, J=8.0, 7.8 Hz), 7.02 (1H, dd, J=8.0, 1.2 Hz) 7.00 (d, 1H, J=8.8, 2.4 Hz), 6.47 (1H, dd, J=7.0, 2.3 Hz), 6.46 (1H, d, J=2.4 Hz), 4.58 (1H, sept., J=6.1 Hz), 4.29 (1H, sept., J=6.2 Hz), 3.74 (1H, d, J=8.0 Hz, 3.69 (3H, s) 3.62 (1H, d, J=8.1 Hz), 1.36–1.35 (6H, m), 1.19–1.18 (6H, m), 1.12–1.11 (6H, m);

$^{13}$C NMR (CDCl$_3$) d 163.6, 158.2, 155.9, 131.2, 131.0, 129.3, 127.7, 122.1, 119.0, 117.6, 105.7, 110.1, 79.3, 71.5, 69.9, 67.0, 55.4, 28.0, 22.1, 22.0, 21.9. Anal. Calc'd for C$_{24}$H$_{31}$NO$_4$: C, 72.52; H, 7.86; N, 3.52. Found: C, 72.82, H, 8.07; N, 3.52.

EXAMPLE 14D 4,5-Dihydro-2-[2'-methoxy-4',6-bis(1-methylethoxy)-1,1'-biphenyl]-2-yl-3,4,4-trimethyloxazolium Iodide

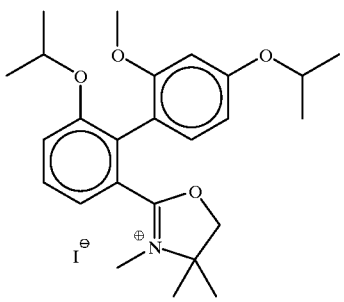

To a stirred solution of 4,5-dihydro-2-[2'-methoxy-4',6-bis(1-methyethoxy) 1,1'-biphenyl)-2'-yl]-4,4-dimethyloxazode (5.80 g, 14.6 mmol) in dry DMSO (30 mL) is added MeI (12.42 g, 87.5 mmol) at ambient temperature. [Pursuant to procedure in H. J. Meyers & J. Slade, J. Org. Chem. 45:2785 (1980)]. The resulting mixture is stirred overnight and diluted with dry Et$_2$O. The precipitate is removed by filtration. The solid is triturated with CHCl$_3$ (400 mL) and filtered. Evaporation of the filtrate followed by recystallization from MeOH/EtOAc gives the title compound as a white solid: 7.40 g (94%); mp 213–214° C.;

$^1$H NMR (CDCl$_3$) d 7.8 (1H, dd, J=8.0, 1.1 Hz), 7.47 (1H, dd, J=8.0, 8.0 Hz), 7.18 (1H, br d, J=8.2 Hz), 6.94 (1H, d, J=8.4 Hz), 6.52 (1H, dd, J=8.4, 2.3 Hz) 6.47 (1H, d, J=2.3 Hz), 5.09 (1H, d, J=9.5 Hz), 4.85 (1H, d, J=9.4 Hz), 4.57 (1H, sept., J=6.2 Hz), 4.44 (1H, sept., J=6.0 Hz), 3.68 (3H, s) 2.87 (3H, s), 1.63 (3H, s) 1.33–1.31 (6H, m), 1.28 (3H, s), 1.16–1.15 (6H, m).

13C (CDCl$_3$) d 172.8, 159.8, 157.6, 155.9, 131.9, 120.5, 128.1, 122.5, 122.4, 118.9, 114.9, 106.4, 100.5, 82.3, 71.2, 70.0, 67.57, 55.7, 30.36, 24.2, 23.4, 21.9, 21.8, 21.7, 21.6. Anal. Calc'd for C$_{25}$H$_{34}$NO$_4$: C,55.66; H, 6.35; N, 2.60. Found: C, 55.82; H, 6.42; N, 2.55.

EXAMPLE 14E

2'-Methoxy-4',6-bis(1-methylethoxy)-1,1'-biphenyl-2-carboxylic acid

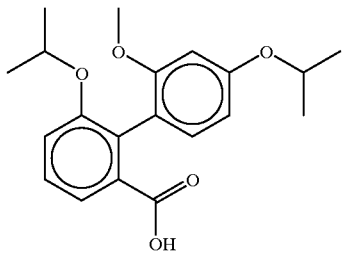

4,5-Dihydro-2-[1'-methoxy-4',6-bis(1-methylethoxy)-(1,1'-biphenyl)-2-yl]-3,4,4-trimethyloxazolium Iodide (13.2 g, 24.5 mmol) is heated and stirred under reflux overnight in a mixture of 20% aqueous NaOH/MeOH (1:1, 280 mL). The reaction is evaporated until turbid and diluted with H$_2$O (300 mL). The solution is acidified with concentrated HCl and the precipitated acid is extracted into CH$_2$Cl$_2$. Evaporation of the solvent gives a glass. Crystallization of the glass from cyclohexane gives the title compound as a white solid: 7.10 g (84%); mp 118–120° C.; IR (KBr) 1697 (C=O).

$^1$H NMR (CDCl$_3$) d 7.52 (1H, dd, J=7.7, 1.2 Hz), 7.30 (1H, dd, J=8.0 Hz), 7.13 (1H, dd, J=8.3, 1.2 Hz), 7.06 (1H, d, J=8.3 Hz), 6.56 (1H, dd, J=8.4, 2.4 Hz), 6.46 (1H, J=2.3 Hz), 4.59 (1H, sept., J=6.1 Hz), 4.26 (1H, sept., J=6.3 Hz), 3.66 (3H, s), 1.37 (6H, J=6.2 Hz), 1.08 (3H, d, J=6.0 Hz).

$^{13}$C NMR (CDCl$_3$) d 171.8, 158.7, 157.7, 156.1, 132.4, 131.6, 129.6, 127.8, 122.6, 119.9, 117.4, 105.9, 100.2, 71.9, 69.9, 55.3, 22.2, 22.1, 21.9, 21.9. Anal. Calc'd for C$_{20}$H$_{24}$O$_5$; C, 69.75; H, 7.02. Found: C, 69.83; H, 6.90.

EXAMPLE 14F

N,N-Diethyl-[2'-methoxy-4',6-bis(1-methylethoxy)-1,1'-biphenyl]-2-carboxamide

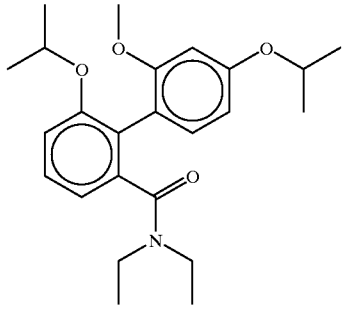

To a mixture of 2'-methoxy-4',6-bis(1-methylethoxy-1,1'-biphenyl-2-carboxylic acid (3.40 g, 9.9 mmol), PyBOP (5.15 g, 9.9 mmol) and Et$_2$NH (0.88 g, 12.1 mmol), in CH$_2$Cl$_2$ (30 mL) is added N,N-diisopropylethyl amine (2.82 g, 21.8 mmol). The resulting mixture is stirred overnight under argon. The solvent is evaporated and the residue is dissolved in EtOAc (250 mL). The EtOAc solution is extracted with 5% HCl (3×70 mL), washed with brine, and extracted with NaHCO$_3$ (3×70 mL) and dried over MgSO$_4$. Filtration and evaporation of solvent gives a light brown oil. The oil is purified by flash chromatography (40% EtOAc/hexane)

affording the desired amide as a solid. The solid is recrystallized from hexane (50 mL) giving the title compound as a white solid: 3.35 g (85%); mp 73–74° C.; IR (neat) 1629 cm$^{-1}$ (C=O).

$^1$H NMR (CDCl$_3$) d 7.28 (1H, dd, J=8.0 Hz), 7.15 (1H, d, J=8.2 Hz), 6.92 (1H, d, J=8.0 Hz), 6.46 (1H, dd J=8.2, 2.3 Hz), 6.43 (1H, d J=2.1 Hz), 4.55 (1H, sept., J=6.1 Hz), 4.32 (1H, sept., J=6.1 Hz), 3.77 (1H, m), 3.68 (3H, s), 3.19 (1H, m), 2.76 (1H, m), 2.63 (1H, m), 1.3–1.31 (6H, m), 1.18 (3H, d, J=6.1 Hz), 1.09 (3H, d, J=6.0 Hz), 0.84 (3H, t, J=7.1 Hz), 0.67 (3H, t J=7.2 Hz).

$^{13}$C NMR (CDCl3) d 170.0, 158.5, 156.0, 139.4, 132.2, 128.4, 126.0, 118.2, 117.5, 114.7, 105.5, 100.0, 71.1, 69.8, 55.1, 41.6, 37.6, 22.2, 22.1, 21.9, 21.7, 13.7, 11.8.

Anal. Calc'd for C$_{24}$H$_{33}$NO$_4$; C, 72.15; H, 8.33; N, 3.51. Found C, 72.20; H, 8.56; N, 3.56.

EXAMPLE 14G

4-Methoxy-2,5-bis(1-methylethoxy)-9H-fluoren-9-one

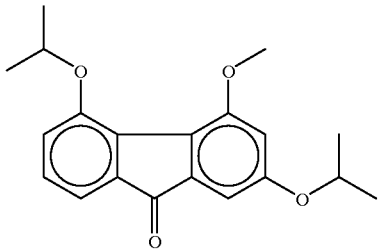

To a stirred solution of LDA (15.0 mmol) in THF (30 mL) is added N,N-[diethyl-2'-methoxy-4',6-bis(1-methylethoxy)-1,1'-biphenyl]-2-carboxamide (1.28 g, 3.2 mmol) in THF (15.0 mL) at 50° C. The resulting yellow solution is allowed to warm to ambient temperature and stirred for 48 hours under argon. During this period the solution turns a brilliant red color. The red solution is quenched with saturated NH$_4$Cl (30 mL). The mixture is diluted with THF (150 mL) and separated. The NH$_4$Cl layer is extracted with THF (50 mL) and the combined organic extracts are dried over MgSO$_4$. The THF is evaporated and the resulting red oil purified by flash chromatography (15% EtOAc/hexane) affording a red solid. Recrystallization from hexane yields the title compound as red flakes: 0.65 g (62%); mp 74–75° C.; IR (KBr) 1712 cm$^{-1}$ (C=O); UV (MeOH) 1 max=476 nm, e=1,570, 1 max=339 nm, e=3,489 1 max=276, e=40,200.

$^1$H NMR (CDCl$_3$) d 7.27 (1H, dd, J=6.9 Hz, J=1.2 Hz), 7.1 (1H, dd, J=8.3, 6.8 Hz), 7.04 (1H, dd, J=8.2, 1.2 Hz) 6.86 (1H, d, J=2.2 Hz), 6.57 (1H, d, J=2.2 Hz), 4.59 (1H, m), 3.88 (3H, s) 1.38 (6H, d, J=6.1 Hz), 1.35 (6H, d, J=6.1 Hz). Anal. Calc'd for C$_{20}$H$_{22}$O$_4$; C, 73.60; H, 6.79. Found: C, 73.46; H, 6.83.

EXAMPLE 14H 2,5-Dihydroxy-4-methoxy-9H-fluoren-9-one (dengibsin)

To a stirred solution of 4-methoxy-2,5-bis-(1-methylethoxy)-9H-fluoren-9-one (0.58 g, 1.8 mmol) in CH$_2$Cl$_2$ (15.0 mL) is added BCl$_3$ (7.2 mL, 7.2 mmol) (1.0M) at 0° C. The green mixture is allowed to warm to ambient temperature and stirred for 2 hours under argon. The mixture is cooled to OC and quenched with H$_2$O (20 mL). The precipitated red solid is removed by filtration and recrystallized from MeOH/H$_2$O affording 0.331 g (76%) of the title compound as a red solid: mp 235–237° C. (lit., 238–240° C.); IR (KBr) 1697, 1614, 1597 cm$^{-1}$; UV (EtOH) 1 max=265, 274 and 338 nm (e=32,576, 36,000 and 3,406 nm.

$^1$H NMR (CD$_3$COCD$_3$) d 9.22 (1H, broad s), 9.92 (1H, s), 7.16–7.09 (2H, m), 6.96 (1H, dd, J=7.02, 2.1 Hz), 6.81 (1H, d, J=2.0 Hz), 6.78 (1H, d, J=2.1 Hz); Anal. Calc'd for C$_{14}$H$_{10}$O$_4$: C,69.42; H, 4.16. Found: C, 69.03; H, 4.26.

EXAMPLE 15A

1-Bromo-2-methoxy-4-allyloxybenzene

To a stirred mixture of K$_2$CO$_3$ (3.45 g, 0.025 mol), and 3-methoxy-4-bromo-phenol (6.09 g, 0.030 mol) at ambient temperature under argon is added allyl bromide (3.60 g, 0.030 mol). The resulting mixture is heated and stirred overnight. The mixture is filtered and the filtrate is concentrated on the rotovap. The residue is partitioned between Et$_2$O and H$_2$O. The Et$_2$O layer is separated and extracted with 2×70 ml 5% NaOH, washed with brine, dried (MgSO$_4$) and filtered. Evaporation on the rotovap followed by flash chromatography (EtOAc-hexane 1:9) gives 5.93 (81%) of the title compound. Rf–0.41 (EtOAc-hexane 25:75) HNMR (CDCl$_3$) d 7.38 (d, 1H), 6.38 (dd, 1H) 6.1–5.9 (m, 1H), 5.41 (d, 1H), 5.29 (d, 1H), 4.51–4.48 (m, 2H), 3.84 (s, 3H).

EXAMPLE 15B 4,5-Dihydro-2-[2'-methoxy-4'-allyloxy-6-(1-methylethoxy)-1,1'-biphenyl-2-yl]-4,4-dimethyl-oxazole To a stirred solution of the Grignard reagent prepared from Mg (0.803 g, 0.033 mol) and 1-bromo-2-methoxy-4-allyloxybenzene (6.83 g, 0.028 mol) in THF (45 ml) is added, 4,5-dihydro-2-[2,3-bis(1-methylethoxy)-phenyl-1-yl]-4,4-dimethyl-oxazole (8.15 g, 0.0280 mol), in THF (30 mL). The temperature rises from 24° to 42° C. during the addition. After the reaction moderates it is stirred at ambient temperature for 72 hours. A saturated solution of NH$_4$Cl (75 mL) is then added and the THF layer is separated, washed with brine, dried (MgSO$_4$) and filtered. The filtrate is evaporated to give 9.2 g of a viscous oil. Flash chromatography (EtOAC-hexane 40:60) gave 6.90 g (62%) of a pale yellow liquid. Anal. Calc'd for C$_{24}$H$_{29}$NO$_4$: C, 72.89; H, 7.39; N, 3.34. Found: C, 72.94; H 7.56; H, 3.55

EXAMPLE 15C

2'-Methoxy-4'-allyloxy-6-(1-methylethoxy)-1,1'-biphenyl-2-carboxylic Acid

Iodomethane (8.56 mL) is added to a stirred solution of 4,5-dihyro-2-[2'methoxy-4'-allyloxy-6-(1-methylethoxy)-1,1'-bipheny]-2-yl-4,4-dimethyl-oxazole (5.70 g, –0.0144 mol) in dry DMSO (19.00 mL) at ambient temperature. The resulting yellow solution is stirred overnight then poured into dry Et$_2$O (400 mL). The resulting white precipitate is collected on a buchner funnel and washed with fresh Et$_2$O then partially dissolved in CHCl$_3$ (300 mL). The mixture is filtered and the filtrate is evaporated to give a white solid. The solid is heated and stirred in 20% NaOH (100 mL) methanol(100 mL) overnight. The resulting clear solution is evaporated on the rotovap until turbid then diluted with H$_2$O (200 mL), then acidified to pH=1 with aqueous HCl and extracted with CH$_2$Cl$_2$ (400 mL). The CH$_2$Cl$_2$ phase is washed with brine and dried (MgSO$_4$). Filtration and evaporation gives 5.77 g (98%) of a tan solid. Recrystallization (cyclohexane) gives the analytical sample, mp 101–103° C. Anal. Calc'd for C$_{20}$H$_{22}$O$_5$; C, 70.46; H, 6.48. Found C, 70.08; H, 6.75.

EXAMPLE 15D

N,N-Diethyl-2'-methoxy-4'allyloxy-6-(1-methylethoxy)-[1,1'-Bipheny]-2-carboxamide (A) Thionyl Chloride Procedure I: To a stirred solution of 2'-methoxy-4'-allyloxy-6-(1-methylethoxy)-1,1'-bipheny)-2-yl-2-carboxylic acid (3.57 g, 0.014 mol) in dry CH$_2$Cl$_2$ (33 mL) is added dropwise SOCl$_2$ (1.30 mol) at ambient temperature. The solution is stirred at ambient temperature for 45 min. then cooled to 0° and diethylamine (10.75 mL, 0.104 mol) is added dropwise. During addition the temperature is kept below 25° C. The resulting mixture is stirred for 2 hours at ambient temperature then diluted with CH$_2$Cl$_2$ (50 mL). The CH$_2$Cl$_2$ is washed with H$_2$O (2×200 mL) extracted with 5% NaHCO$_3$ (200 mL) washed with brine, dried (MgSO$_4$) and filtered. Concentration of the filtrate followed by chromatography (EtOAc hexane 1:1) gives first the lactone [compound 2,3-allyloxy-10-(1-methylethoxy)-benzo-[c]chromen-6-one] (0.082 g) followed by the desired flourenone 1.60 g (39%). [Compound 3,2-allyloxy-4-(1-methylethoxy)-fluoren-9-one].

(B) Thionyl Chloride II: To a stirred solution of 2'-methoxy-4'-allyoxy-6-(1-methyleathoxy)-1,1'-biphenyl-2-yl-2-carboxylic acid (2.53 g; 0.0074 mol) in dry CH$_2$Cl$_2$ (30 moL) is added SOCl$_2$ (0.88 mL, 0.017 mL) and the resulting mixture is stirred for 20 min. then heated at reflux for 15 min. The resulting tan solution is cooled to 0° C. and diethylamine (7.66 mL, 0.074 mol) is added dropwise. Following the addition of diethylamine, the resulting mixture is diluted with CH$_2$Cl$_2$ (15 mL) then treated as described above to give 2.18 g (74%) of a clear oil. HRMS (HRFAB); Calc'd for C$_{24}$H$_{32}$NO$_4$: 398.233134. Found: 398.230815.

(C) PYBOP Procedure: To a stirred solution of of 2'-methoxy-4'-allyoxy-6-(1-methyleathoxy)-1,1'-biphenyl-2-yl-2-carboxylic acid (2.17 g, 0.0063 mol), PyBOP (3.27 g, 0.0063 mol) and diethylamine (0.83 mL, 0.0080 mol) in CH$_2$Cl$_2$ (20 mL) is added diisopropylethylamine (2.43 mL, 0.0140 mol). The solution turns brown and there is an exotherm (temp rose ~10° C.). The mixture is stirred overnight at ambient temperature, diluted with CH$_2$Cl$_2$ (~100 mL) and evaporated on the rotary evaporator. The residue is dissolved in EtOAc (200 mL). The EtOAC is extracted with 5% HCl (3×70 mL) separated, washed with brine then extracted with 5% NaHCO$_3$ (3×70 mL), washed with brine, dried (MgSO$_4$) and evaporated. The residue is chromatographed as described above to give 3.03 g (78%) of the title compound as a clear oil.

IV. Biological Data

Protein Kinase C Purification

Protein kinase C (PKC) was partially purified from the cytosol of rat brains as described by Salama, S. E., *Thromb. Res.* 44:649–660, 1986. After removing the brains, all manipulations were carried out at 4° C. Briefly, the cerebellum was removed from 8–10 rat brains and each brain was then homogenized in 9 ml sucrose/EDTA (0.32 M sucrose, 1 mM EDTA, 5 mM Tris, pH 7.4). The pooled homogenate was then centrifuged at 1000×g for 10 min at 4° C., the pellet resuspended in the same volume of fresh sucrose/EDTA and recentrifuged at 1000×g for 10 min. at 4° C. The supernatants from each of these spins was pooled and centrifuged at 25,700×g for 30 min. at 4° C., and the resulting pellet homogenized in 20 ml of buffer A. (20 mM Tris pH 7.5, 0.1 mM calcium chloride, 0.4 mM leupeptin), at 4° C. Membrane associated PKC was then pelleted by centrifugation at 45,700×g at 4° C. for 15 min. and resuspended in 20 ml of buffer A. This step was repeated for a total of 3 centrifugations, discarding the supernatants and finally resuspending the pellet in 20 ml of buffer B (20 mM Tris pH 7.5, 1 mM EGTA, 1 mM EDTA, and 0.01 mM leupeptin) and stirring on ice for 30 min. Disassociated PKC was then collected by centrifuging at 45,700×g at 4° C. for 15 min. The pellet was discarded and the supernatant centrifuged at 100,000×g at 4° C. for 60 min. The pellet was again discarded and the supernatant was adjusted to remove all EDTA and EGTA by adding sufficient volume of a stock solution containing 100 mM each CaCl$_2$ and MgCl$_2$ to give a final concentration of 1 mM Ca$^{++}$ and 1 mM Mg$^{++}$. The resulting slurry was then applied to a 12 cm×1 cm DE-52 (DEAE cellulose, Whatman®) column previously equilibrated with buffer B. The flow rate for all column chromatography was 0.75 ml/min. After washing the column with 70 ml of buffer B to remove unbound proteins, undesired proteins were eluted with 40 ml of buffer B containing 40 mM NaCl and the PKC containing fraction eluted with 20 ml of buffer B containing 150 mM NaCl. The PKC eluate was then concentrated to about 5 ml using an Amicon® ultrafiltration cell fitted with a PM-10 membrane, and excess NaCl removed by adding back 30 ml 5 mM Tris pH 7.4 and reconcentrating to a final volume of about 5 ml. The concentrated and desalted PKC prep was then adjusted to contain 10% glycerol and 0.5% Triton X-100 before aliquoting and storing 200 µL volumes at −70° C. Frozen preps were stable for at least 3 months at −70°0 C.

Assay Procedures

Protein kinase C was assayed using a semi-automated 96-well plate procedure based upon the procedures of Aftab and Hait, and Parant and Vial (Aftab, D. T. and W. N. Hait., *Anal Biochem.* 187:84–88. 1990.; Parant, M. R. and Vial, H. J., *Anal Biochem.* 184:283–290. 1990). Briefly, each well of a 96 well "u" well microtiter plate received a total of 100 µl assay volume consisting of final concentrations of 30 mM Tris pH 7.4, 10 mM MgSO4, 1 mM EGTA, 200 µg Hl histone (Sigma Type III-S H5505), 50 µM ATP, 0.5 µCi 30 Ci/mmol $^{32}$P-ATP, and 30 µl PKC extract diluted in 5 mM Tris, pH 7.4 containing 1 mg per ml each of leupeptin, pepstatin and chymastatin, and 1 mM phenylmethylsulfonylfluoride. Reactions were started by adding the PKC extract and stopped by the addition of 50 µl 40% trichloroacetic acid, followed by 25 µl of 50 mM unlabelled ATP and 25 µl of 0.5% bovine serum albumin, and then collected on glass fiber filters using a Skatron® automatic micro cell harvester. Samples were washed for 30 seconds with 5% trichloroacetic acid, dried for 5 seconds on the harvester, and then transferred to scintillation vials for counting and subsequent data analysis. Reactions were run for five to seven minutes at room temperature.

Data Analysis Procedures

Data were fit to a competitive binding curve using the ENZFITTER® program (Biosoft). The error estimated for the IC$_{50}$ values was less than 10%. The results are summarized in Table 1.

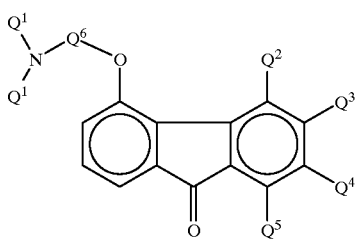

Y is NH2, NHR, NHCOR, wherein R is $C_1$–$C_5$ alkyl or phenyl;

Z is hydrogen, $C_1$–$C_5$ alkyl, fluoro or chloro, with the proviso that,

Z may be present at the 1, 2, 3 or 4 position, and when present at the 1, 2 or 4 position, replaces Y, V or X, respectively;

or a pharmaceutically acceptable salt thereof.

2. The compound according to claim 1, wherein B is O; $R^5$ is ethylene; X is methoxy, ethoxy, n-propoxy or fluoro; R is $C_1$–$C_4$ alkyl or phenyl; and Z is hydrogen.

TABLE 1

| I.D. No. | $Q^1$ | $Q^2$ | $Q^3$ | $Q^4$ | $Q^5$ | $Q^6$ | HCl salt | PKC $IC_{50}$ ($\mu M$) |
|---|---|---|---|---|---|---|---|---|
| 105,509 | —Et | —OCH₃ | —H | —OPr | —NH₂ | —Et— | 1-HCl | 0.079 |
| 105,473 | —Et | —OCH₃ | —H | —OCH₃ | —NH₂ | —Et— | 1-HCl | 0.160 |
| 105,290 | -pyr. | —OCH₃ | —H | —OPr | —H | —Et— | 1-HCl | 0.46 |
| 104,952 | —Et | —OCH₃ | —H | —OPr | —H | —Et— | 1-HCl | 0.576 |
| 105,950 | —Et | —OCH₃ | —H | —OCH₃ | —H | —Et— | 1-HCl | 0.9 |
| 104,652 | —Et | —OCH₃ | —H | —H | —H | —Et— | 1-HCl | 1 |
| 105,711 | —Et | —OCH₃ | —H | —A | —H | —Et— | 2-HCl | 1.1 |
| 104,427 | -mor. | —OCH₃ | —H | —OPr | —NH₂ | —Et— | 1-HCl | 2.3 |
| 11,080 | —Et | —H | —H | —A | —H | —Et— | 2-HCl | 3 |
| 104,004 | —Et | —H | —A | —H | —H | —Et— | 2-HCl | 4 |
| 103,949 | —Et | —H | —H | —OCH₃ | —H | —Et— | 1-HCl | 7 |
| 103,049 | —Et | —H | —H | —OPr | —H | —Et— | 1-HCl | 9 |
| 101,209 | —CH₃ | —H | —H | —A | —H | —Et— | 2-HCl | 11 |
| 104,147 | —Et | —H | —H | —H | —A | —Et— | 2-HCl | 15 |
| 102,352 | —CH₃ | —H | —H | —A | —H | —Pr— | 2-HCl | 50 |
| 103,388 | —Et | —H | —H | —OCH₃ | —H | —Pr— | 1-HCl | 56 |
| 104,488 | —Et | —A | —H | —H | —H | —Et— | 2-HCl | 92 |
| 104,439 | -mor. | —OCH₃ | —H | —OPr | —H | —Et— | 1-HCl | >10 |
| — | -pyr. | —OCH₃ | —H | —OPr | —NH₂ | —Et— | 1-HCl | — |
| — | —Et | —OCH₃ | —H | —A | —NH₂ | —Et— | 2-HCl | — |
| — | —Et | —OCH₃ | —H | —B | —NH₂ | —Et— | 1-HCl | — |

KEY
—Et = ethyl
—Et— = ethylene
—Pr— = propylene
—OPr = propyloxy
—A = —OR⁶N(R¹)₂
—B = —OR⁶OR¹
-mor- = R¹'s combined to form morpholino
-pyr. = R¹'s combined to form pyrrolidinyl

What is claimed is:

1. A compound of the formula:

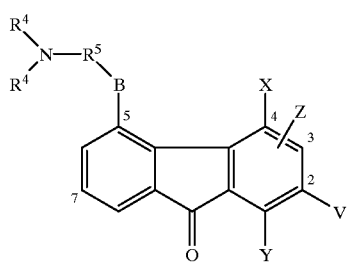

wherein:

B is O or S;

$R^4$ is methyl, ethyl, n-propyl, or both $R^4$'s can be combined to give pyrrolidinyl, piperidinyl or morpholino;

$R^5$ is $C_1$–$C_5$ alkylene;

V is hydrogen, methoxy, ethoxy, n-propoxy, butoxy;

X is hydrogen, methoxy, ethoxy, n-propoxy, fluoro or chloro;

3. The compound according to claim 1 wherein B is O; $R^4$ is methyl or ethyl; $R^5$ is ethylene; V is hydrogen, methoxy, ethoxy, n-propoxy; X is hydrogen or methoxy; Y is NH₂; and Z is hydrogen.

4. The compound, or pharmaceutically acceptable salt thereof, according to claim 1, wherein each $R^4$ is ethyl; $R^5$ is ethylene; B is O; X is methoxy; Z is hydrogen; V is propyloxy; and Y is NH₂.

5. The compound, or pharmaceutically acceptable salt thereof, according to claim 4, wherein the salt is HCl.

6. The compound, or pharmaceutically acceptable salt thereof, according to claim 1, wherein each $R^4$ is ethyl; $R^5$ is ethylene; B is O; X is methoxy; Z is hydrogen; V is methoxy; and Y is NH₂.

7. The compound, or pharmaceutically acceptable salt thereof, according to claim 6, wherein the salt is HCl.

8. The compound, or pharmaceutically acceptable salt thereof, according to claim 1, wherein each $R^4$ is morpholinol; $R^5$ is ethylene; B is O; X is methoxy; Z is hydrogen; V is propyloxy; and Y is NH₂.

9. The compound, or pharmaceutically acceptable salt thereof, according to claim 8, wherein the salt is HCl.

10. The compound, or pharmaceutically acceptable salt thereof, according to claim 1, wherein each $R^4$ is pyrrolidinyl; $R^5$ is ethylene; B is O; X is methoxy; Z is hydrogen; V is propyloxy; and Y is $NH_2$.

11. The compound, or pharmaceutically acceptable salt thereof, according to claim 10, wherein the salt is HCl.

12. A method of inhibiting Protein Kinase C comprising the administration to a patient in need thereof an effective amount of Protein Kinase C inhibitory amount of a compound according to claim 1.

13. A method of inhibiting angiogenesis comprising administering to a patient in need thereof an effective amount of Protein Kinase C inhibitory amount of a compound according to claim 1.

14. A method of treating a condition of abnormal blood flow comprising the administration to a patient in need thereof an effective Protein Kinase C inhibitory amount of a compound according to claim 1.

15. The method according to claim 14 wherein the condition treated is hypertension.

16. The method according to claim 14 wherein the condition treated is ischemia.

17. The method according to claim 14 wherein the condition treated is atherosclerosis.

18. A method of inhibiting platelet aggregation comprising the administration to a patient in need thereof an effective Protein Kinase C inhibitory amount of a compound according to claim 1.

19. A method of inhibiting inflammation comprising the administration to a patient in need thereof an effective Protein Kinase C inhibitory amount of a compound according to claim 1.

20. The method according to claim 19 wherein the condition treated is transplant rejection.

21. The method according to claim 19 wherein the condition treated is psoriasis.

22. The method according to claim 19 wherein the condition treated is asthma.

23. The method according to claim 19 wherein the condition treated is gouty arthritis.

24. The method according to claim 19 wherein the condition treated is lung fibrosis.

25. A method of inhibiting alveolar macrophage activation comprising the administration to a patient in need thereof an effective Protein Kinase C inhibitory amount of a compound according to claim 1.

26. A pharmaceutical composition comprising a compound of claim 1 and a pharmaceutical carrier.

* * * * *